US008442621B2

(12) United States Patent
Gorek et al.

(10) Patent No.: US 8,442,621 B2
(45) Date of Patent: May 14, 2013

(54) SURGICAL TRAJECTORY MONITORING SYSTEM AND RELATED METHODS

(75) Inventors: Josef Gorek, Oakland, CA (US);
Thomas U. Scholl, San Diego, CA (US);
Eric Finley, San Diego, CA (US);
Albert C. Kim, San Diego, CA (US);
Martin Herman, Chicago, IL (US)

(73) Assignee: NuVasive, Inc., San Diego, CA (US)

( * ) Notice: Subject to any disclaimer, the term of this patent is extended or adjusted under 35 U.S.C. 154(b) by 678 days.

(21) Appl. No.: 12/301,233

(22) PCT Filed: May 17, 2007

(86) PCT No.: PCT/US2007/011962
§ 371 (c)(1),
(2), (4) Date: Jun. 3, 2009

(87) PCT Pub. No.: WO2007/136784
PCT Pub. Date: Nov. 29, 2007

(65) Prior Publication Data
US 2010/0036384 A1 Feb. 11, 2010

Related U.S. Application Data

(60) Provisional application No. 60/801,488, filed on May 17, 2006, provisional application No. 60/918,955, filed on Mar. 19, 2007, provisional application No. 60/919,049, filed on Mar. 19, 2007, provisional application No. 60/925,630, filed on Apr. 20, 2007.

(51) Int. Cl.
*A61B 5/05* (2006.01)

(52) U.S. Cl.
USPC ............................ 600/424; 606/97; 606/102

(58) Field of Classification Search .............. 606/80–97; 600/407, 424
See application file for complete search history.

(56) References Cited

U.S. PATENT DOCUMENTS

| | | | |
|---|---|---|---|
| 2,666,430 | A | 1/1954 | Gispert |
| 4,164,871 | A | 8/1979 | Cole et al. |
| 4,257,411 | A | 3/1981 | Cho |
| 4,823,780 | A | 4/1989 | Odensten et al. |
| 5,113,953 | A | 5/1992 | Noble |
| 5,440,492 | A | 8/1995 | Kozah et al. |
| 5,446,548 | A | 8/1995 | Gerig et al. |
| 5,467,532 | A | 11/1995 | Ames |
| 5,481,957 | A | 1/1996 | Paley et al. |

(Continued)

OTHER PUBLICATIONS

"Surgical Trajectory Monitoring System and Related Methods." International Search Report from International Application No. PCT/US07/11962. Aug. 20, 2008, 1 page.

*Primary Examiner* — Tse Chen
*Assistant Examiner* — Joel F Brutus
(74) *Attorney, Agent, or Firm* — Jonathan Spangler; Rory Schermerhorn; Heather Prado

(57) ABSTRACT

Systems and methods for determining a desired trajectory and/or monitoring the trajectory of surgical instruments and/or implants in any number of surgical procedures, such as (but not limited to) spinal surgery, including (but not limited to) ensuring proper placement of pedicle screws during pedicle fixation procedures and ensuring proper trajectory during the establishment of an operative corridor to a spinal target site.

32 Claims, 37 Drawing Sheets

U.S. PATENT DOCUMENTS

| | | | |
|---|---|---|---|
| 5,484,029 A | 1/1996 | Eddison | |
| 5,617,926 A | 4/1997 | Eddison et al. | |
| 5,672,820 A | 9/1997 | Rossi et al. | |
| 5,711,299 A | 1/1998 | Manwaring et al. | |
| 5,799,055 A | 8/1998 | Peshkin et al. | |
| 5,870,832 A | 2/1999 | Slocum | |
| 6,045,508 A | 4/2000 | Hossack et al. | |
| 6,092,928 A * | 7/2000 | Mattson et al. | 378/205 |
| 6,254,572 B1 | 7/2001 | Knipfer et al. | |
| 6,263,984 B1 | 7/2001 | Buckman, Sr. | |
| 6,568,850 B2 | 5/2003 | Vallin et al. | |
| 6,621,460 B2 | 9/2003 | Challoner | |
| 6,697,664 B2 | 2/2004 | Kienzle, III et al. | |
| 6,725,080 B2 | 4/2004 | Melkent et al. | |
| 6,727,704 B2 | 4/2004 | Brune et al. | |
| 6,843,793 B2 | 1/2005 | Brock et al. | |
| 2002/0095159 A1 | 7/2002 | Deloge et al. | |
| 2002/0161280 A1 * | 10/2002 | Chatenever et al. | 600/112 |
| 2003/0199882 A1 * | 10/2003 | Gorek | 606/104 |
| 2005/0075578 A1 * | 4/2005 | Gharib et al. | 600/546 |

* cited by examiner

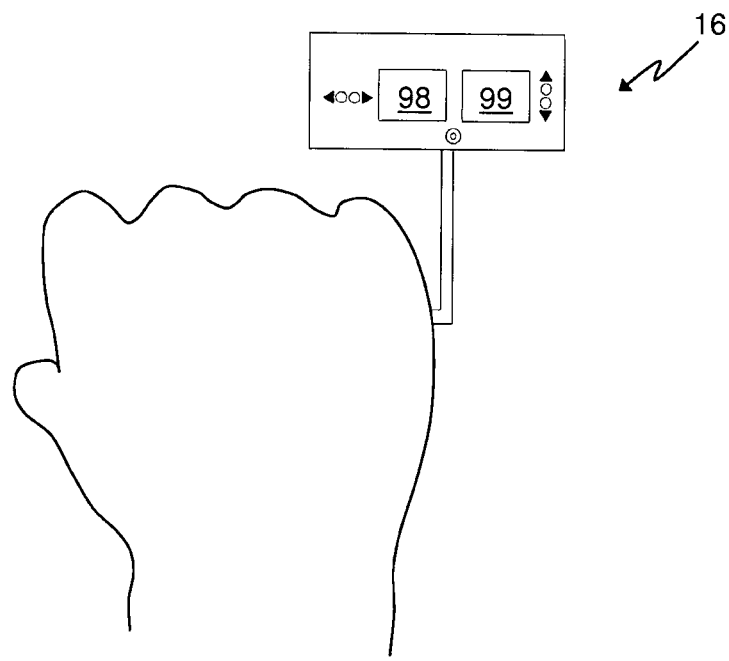
FIG. 17
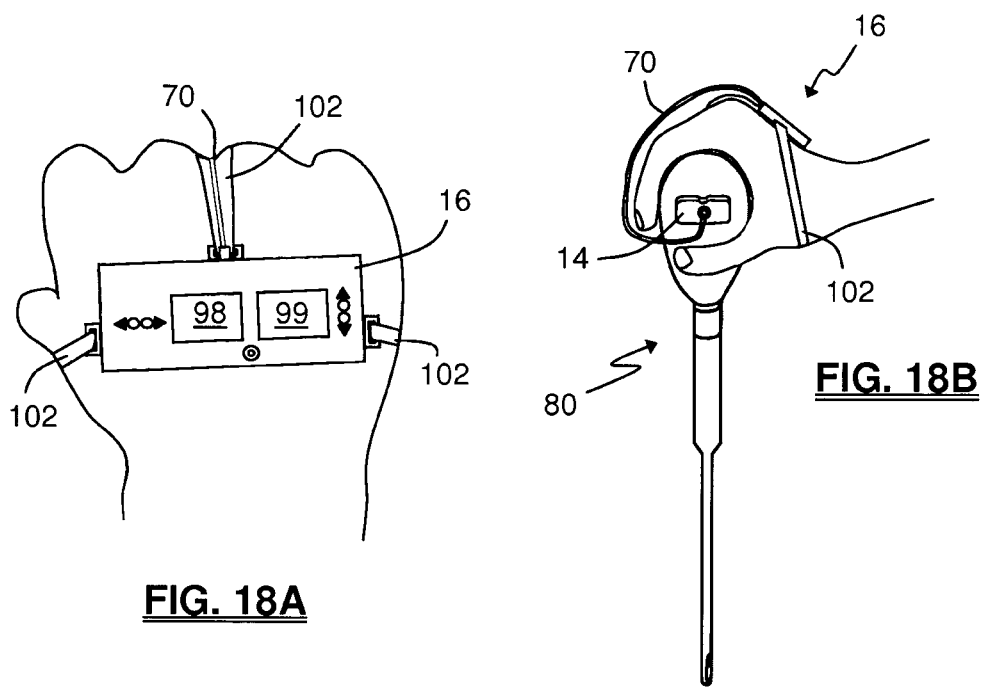
FIG. 18A
FIG. 18B

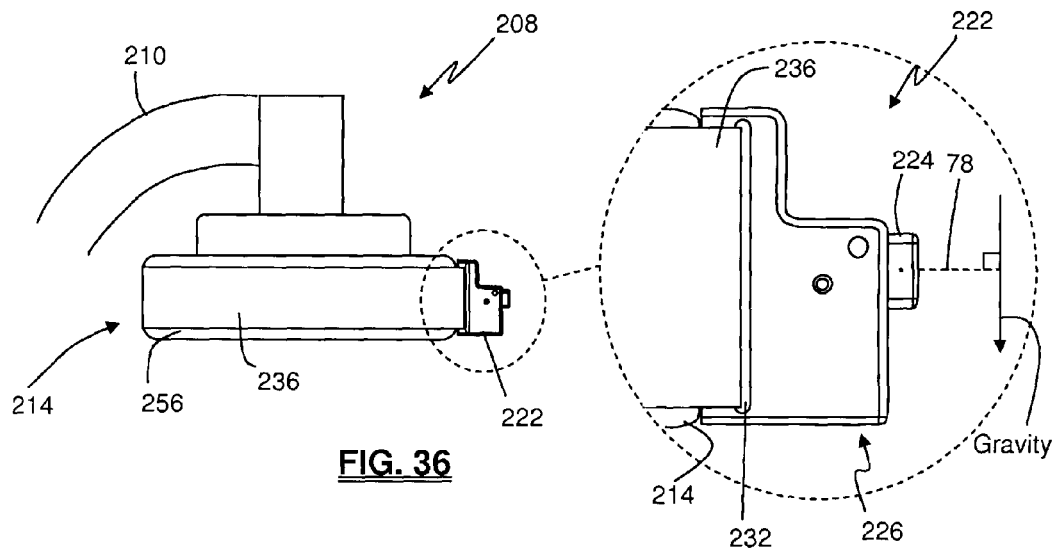
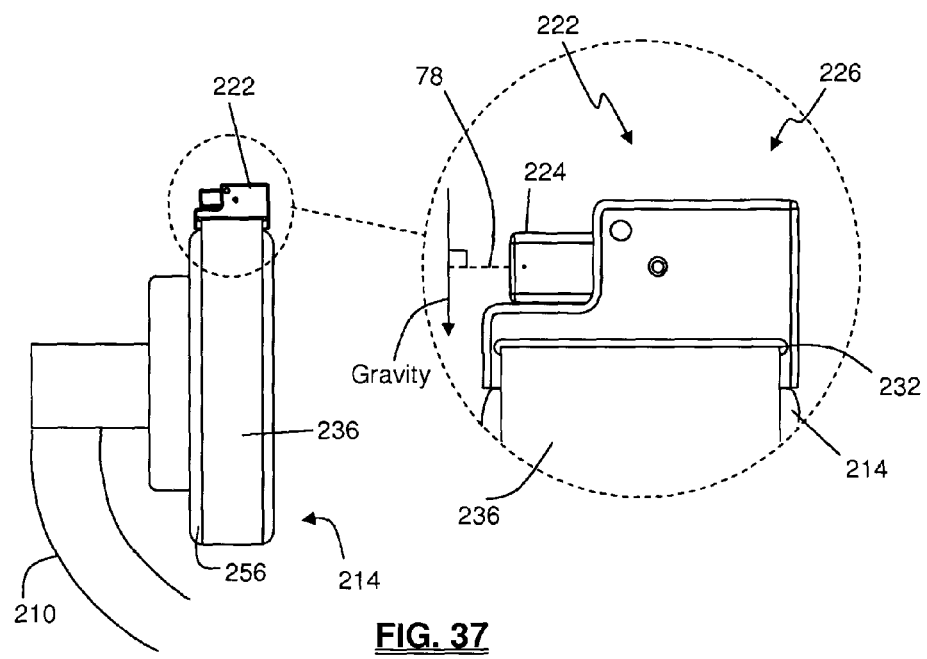

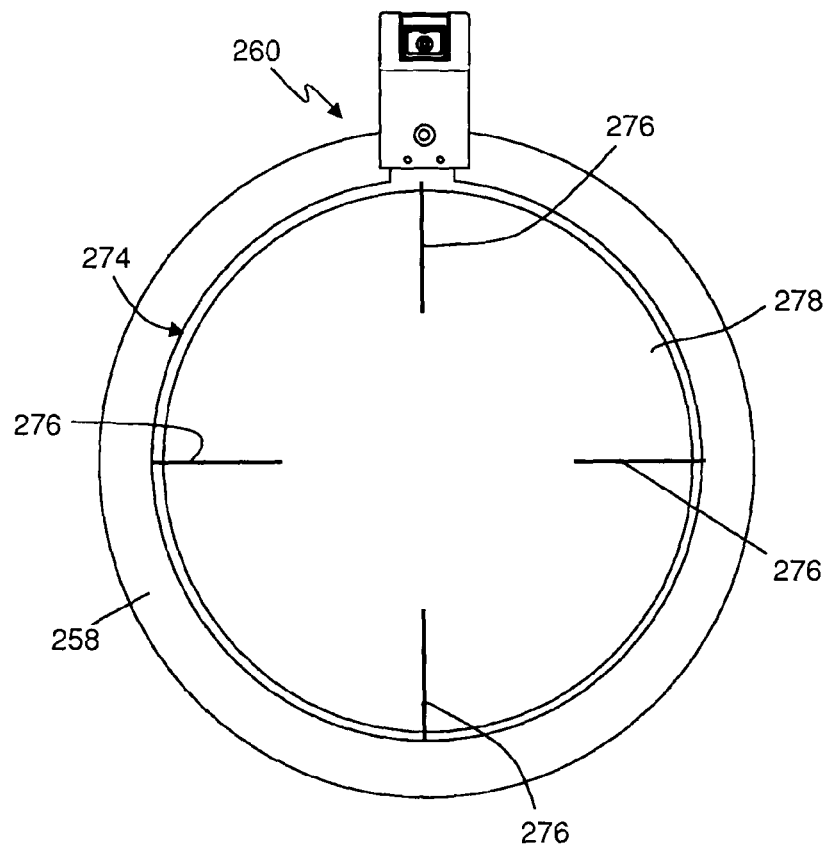
FIG. 46
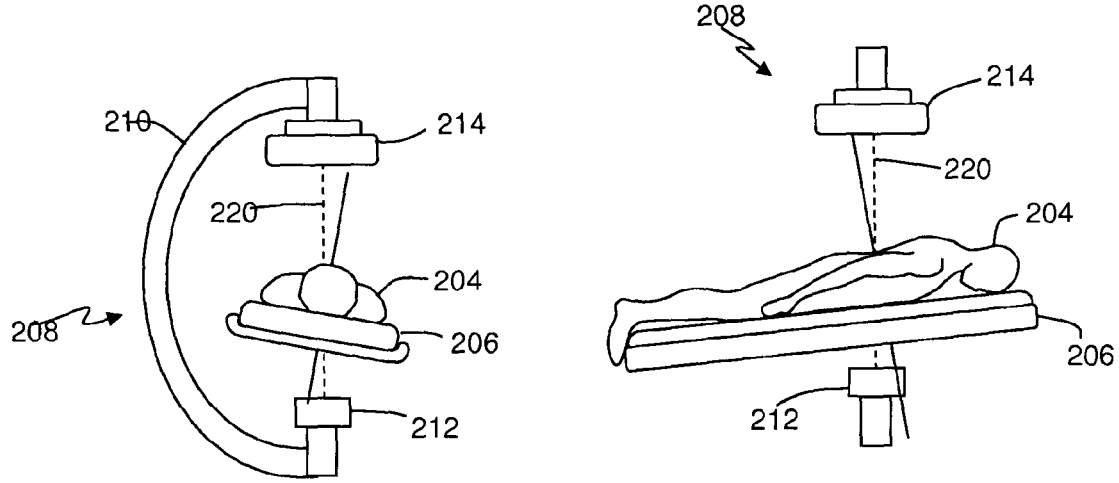
FIG. 47
FIG. 48

Vertical Reference Line

Vertical Reference Line

SURGICAL TRAJECTORY MONITORING SYSTEM AND RELATED METHODS

CROSS-REFERENCE TO RELATED APPLICATIONS

This is an International Patent Application claiming the benefit of priority under 35 U.S.C. §119(e) from the following commonly owned and co-pending applications: U.S. Provisional Patent Application Ser. No. 60/801,488, entitled "Pedicle Access Probe and Related Methods," and filed on May 17, 2006; U.S. Provisional Patent Application Ser. No. 60/918,955, entitled "Trajectory Aligned Pedicle Access," and filed on Mar. 19, 2007; U.S. Provisional Patent Application Ser. No. 60/919,049, entitled "System and Methods for Orienting a Fluoroscope," and filed on Mar. 19, 2007; and U.S. Provisional Patent Application Ser. No. 60/925,630, entitled "Surgical Access System and Methods for Orienting the Same," and filed on Apr. 20, 2007; the entire contents of each of the above noted applications are expressly incorporated by reference into this disclosure as if they were set forth in their entireties herein.

BACKGROUND OF THE INVENTION

I. Field of the Invention

The present invention relates generally to determining a desired trajectory and/or monitoring the trajectory of surgical instruments and implants and, more particularly, doing so during spinal surgery, including but not limited to ensuring proper placement of pedicle screws during pedicle fixation procedures and ensuring proper trajectory during the establishment of an operative corridor to a spinal target site.

II. Discussion of the Art

Determining the optimal or desired trajectory for surgical instruments and/or implants and monitoring the trajectory of surgical instruments and/or implants during surgery have presented challenges to surgeons since the inception of surgery itself. One example is pedicle fixation, which is frequently performed during spinal fusions and other procedures designed to stabilize or support one or more spine segments. Pedicle fixation entails securing bone anchors (e.g. pedicle screws) through the pedicles and into the vertebral bodies of the vertebrae to be fixed or stabilized. Rods or other connectors are used to link adjacent pedicle screws and thus fix or stabilize the vertebrae relative to each other. A major challenge facing the surgeon during pedicle fixation is implanting the pedicle screws without breaching, cracking, or otherwise compromising the pedicle wall, which may easily occur if the screw is not properly aligned with the pedicle axis. If the pedicle (or more specifically, the cortex of the medial wall, lateral wall, superior wall and/or inferior wall) is breached, cracked, or otherwise compromised, the patient may experience pain and/or neurologic deficit due to unwanted contact between the pedicle screw and delicate neural structures, such as the spinal cord or exiting nerve roots, which lie in close proximity to the pedicle. A misplaced pedicle screw often necessitates revision surgery, which is disadvantageously painful for the patient and costly, both in terms of recovery time and hospitalization.

The present invention is aimed primarily at eliminating or at least reducing the challenge associated with determining the optimal or desired trajectory for surgical instruments and/or implants and monitoring the trajectory of surgical instruments and/or implants during surgery.

SUMMARY OF THE INVENTION

The present invention facilitates the safe and reproducible use of surgical instruments and/or implants by providing the ability to determine the optimal or desired trajectory for surgical instruments and/or implants and monitor the trajectory of surgical instruments and/or implants during surgery. By way of example only, the present invention may be used to ensure safe and reproducible pedicle screw placement by monitoring the axial trajectory of surgical instruments used during pilot hole formation and/or screw insertion. Neurophysiologic monitoring may also be carried out during pilot hole formation and/or screw insertion. It is expressly noted that in addition to its uses in pedicle screw placement, the present invention is suitable for use in any number of additional surgical procedures where the angular orientation or trajectory of instrumentation and/or implants and/or instrumentation is important, including but not limited to general (non-spine) orthopedics and non-pedicular based spine procedures It will be appreciated then that while the surgical instruments are generally described below as pedicle access tools, cannulas, retractor assemblies, and imaging systems (e.g. C-arms), various other surgical instruments (e.g. drills, screw drivers, taps, etc. . . . ) may be substituted depending on the surgical procedure being performed and/or the needs of the surgeon.

A surgical trajectory system may include an angle-measuring device (hereafter "tilt sensor") and a feedback device. The tilt sensor measures its angular orientation with respect to a reference axis (such as, for example, "vertical" or "gravity") and the feedback device may display or otherwise communicate the measurements. Because the tilt sensor is attached to a surgical instrument the angular orientation of the instrument, may be determined as well, enabling the surgeon to position and maintain the instrument along a desired trajectory during use.

The tilt sensor may include a sensor package enclosed within a housing. The housing is coupled to or formed as part of a universal clip to attach the tilt sensor to a surgical instrument. The sensor package may comprise a 2-axis accelerometer which measures its angular orientation in each of a sagittal and transverse plane with respect to the acting direction of gravity. The sagittal orientation corresponds to a cranial-caudal angle and the transverse orientation corresponds to a medial-lateral angle. The sensor package is preferably situated such that when the tilt sensor is perpendicular to the direction of gravity, the inclinometer registers a zero angle in both the sagittal and transverse planes. Thus, when the tilt sensor is fixed perpendicularly to the longitudinal axis of the surgical instrument, the angular orientation of the longitudinal axis of the instrument is determined relative to gravity. Alternatively, a 3-axis sensor may be used. The 3-axis sensor may comprise a 2-axis accelerometer to measure sagittal and transverse orientation and either a gyroscope and/or one or more magnetometers (e.g. a single 3-axis magnetometer or a combination of a 1-axis magnetometer and a 2-axis magnetometer) to measure the longitudinal axial rotation of the instrument.

A universal clip may be provided to attach the tilt sensor to the surgical instrument. The universal clip comprises a fastener, which securely holds a surgical instrument to the clip, a sensor bed, which snugly holds the tilt sensor to the clip, a coupler, which connects the sensor bed to the fastener, and a collar, which travels along the coupler to engage the surgical instrument with the fastener.

A surgical instrument for use with the surgical trajectory system may comprise, by way of example only, a pedicle access probe. The instrument may generally comprise a probe member having a longitudinal axis and a handle. The probe member may be embodied in any variety of configurations that can be inserted through an operating corridor to a pedicle target site and bore, pierce, or otherwise dislodge and/or impact bone to form a pilot hole for pedicle screw placement. The probe member may be composed of any material suitable for surgical use and strong enough to impact bone to form a pilot hole. In one embodiment, the material may be capable of conducting an electric current signal to allow for the use of neurophysiologic monitoring.

The handle may be permanently or removably attached to the probe member and may be shaped and dimensioned in any of a number of suitable variations to assist in manipulating the probe member. In some embodiments, the handle includes a cutout region for accommodating attachment of the universal clip. In other embodiments, the handle includes an integral cavity for receiving the tilt sensor directly. In still other embodiments the tilt sensor is permanently integrated into the instrument handle.

A feedback device may be communicatively linked to the tilt sensor via a hard wire or wireless technology. The feedback device may communicate any of numerical, graphical, and audiofeedback corresponding to the orientation of the tilt sensor in the sagittal plane (cranial-caudal angle) and in the transverse plane (medial-lateral angle). The medial-lateral and cranial-caudal angle readouts may be displayed simultaneously and continuously while the tilt sensor is in use, or any other variation thereof (e.g. individually and/or intermittently). The feedback device may be placed next to the patient on the surgical table, or it may be affixed to any number of suitable objects in the operating room. Alternatively, a display may be provided that may be positioned in the practitioner's field of view during surgery. By way of example only, the display may be attached to one of the surgical instrument, the universal clip, and the practitioner's hand.

A bubble level device may be provided with the surgical trajectory system and used to ensure the tilt sensor is functioning correctly. The bubble level device comprises a handle with a bulls-eye level mounted in it. When the handle is placed on a flat surface with the tilt sensor inserted into it, an indicator ring should encircle a bubble captured within the glass. When the bubble is within the indicator ring, the tilt sensor display should read approximately zero-degrees for both the cranial-caudal and medial-lateral angle readouts.

In general, to orient and maintain the surgical instrument along a desired trajectory during pilot hole formation, the surgical instrument is advanced to the pedicle (through any of open, mini-open, or percutaneous access) while oriented in the zero-angle position. The instrument is then angulated in the sagittal plane until the proper cranial-caudal angle is reached. Maintaining the proper cranial-caudal angle, the surgical instrument may then be angulated in the transverse plane until the proper medial-lateral angle is attained. Once the feedback device indicates that both the medial-lateral and cranial caudal angles are matched correctly, the instrument may be advanced into the pedicle to form the pilot hole, monitoring the angular trajectory of the instrument until the hole formation is complete.

Before the pilot hole is formed, the desired angular trajectory (e.g. the cranial-caudal angle and the medial-lateral angle) must first be determined. Preoperative superior view MRI or CAT scan images are used to determine the medial-lateral angle. A reference line is drawn through the center of the vertebral body and a trajectory line is then drawn from a central position in the pedicle to an anterior point of the vertebral body. The resulting angle between the trajectory line and the reference line is the desired medial-lateral angle to be used in forming the pilot hole.

The cranial-caudal angle may be determined using an intraoperative lateral fluoroscopy image incorporating a vertical reference line. Again, a trajectory line is drawn from the pedicle nucleus to an anterior point of the vertebral body. The resulting angle between the trajectory line and the vertical reference line is the desired cranial-caudal angle to be used in forming the pilot hole. A protractor outfitted with a tilt sensor may be provided to assist in determining the cranial-caudal angle in the operating room. Alternatively, the cranial-caudal angle may be calculated preoperatively using imaging techniques that provide a lateral view of the spine. The medial-lateral and cranial-caudal angles should be determined for each pedicle that is to receive a pedicle screw. Alternate and/or additional methods for predetermining the pedicle angles are also contemplated and may be used without deviating from the scope of the present invention.

An alternate feedback device may be provided which can communicatively link multiple tilt sensors at once. Preferably, the alternate feedback device may be linked to three tilt sensors simultaneously, and angle measurement feedback may be provided simultaneously for all attached tilt sensors. In one example, this allows a tilt sensor to be engaged with a surgical instrument, a protractor, and a C-arm fluoroscope without the need for multiple displays and/or connecting and disconnecting the tilt sensor to the various devices during the procedure.

According to one embodiment of the present invention, a coupler may be provided to attach the tilt sensor to a standard C-arm. The coupler comprises a sensor bed which receives and holds the tilt sensor, and a mount which may attach to the C-arm. The sensor bed may be pivotally attached to the mount and may preferably pivot between a horizontal position and a vertical position with respect to the mount. This allows the tilt sensor to be aligned in the same starting orientation with respect the direction of gravity whether the C-arm is in the A/P position or the lateral position. It will be appreciated however that this is not always necessary, as in some instances (such as when determining the cranial-caudal angle using the C-arm) the sensor output is adequate if only one axis of the sensor is perpendicular to gravity.

A coupler may be configured to attach to the C-arm via a belt, strap, Velcro, tape, etc. . . . The coupler may be configured to attach to the sidewall of the C-arm, the face of the C-arm, or any other part of the C-arm. The coupler may also include a reticle/plumb line. The plumb line may comprise a radio-dense marker which will appear on the fluoro-images. The plumb line may be oriented parallel to the direction of gravity to serve as a vertical reference line in the fluoro-images. The radio dense marker may be configured in any number of arrangements to provide additional markings on the fluoro-images. A target may also be provided to augment the plumb line.

In an alternate embodiment of the present invention, it is contemplated that the orientation of C-arm with respect to the patient may be adjusted by moving the patient rather than the C-arm. To accomplish this, by way of example only, a tilt sensor may be attached to the surgical table and the table may be adjusted rather than the C-arm. In still another embodiment, a tilt sensor may be attached directly to the patient and again, the table may be adjusted rather than the C-arm.

In addition to facilitating adjustments to a C-arm orientation, a C-arm equipped with the orientation system of the present invention may have other uses as well. By way of example only, the C-arm may be used to determine a pedicle axis and/or a starting point for pedicle penetration.

The cranial-caudal angle may be determined intraoperatively with a C-arm fluoroscope equipped with the orientation system of the present invention. The C-arm is oriented in a lateral position and then radially rotated until a vertical reference line is parallel to the pedicle axis, this is the trajectory lateral position. The angle measured by the tilt sensor is the cranial-caudal angle of the pedicle axis.

To select a starting point for pedicle penetration, the C-arm may be placed in the trajectory lateral position. From the trajectory lateral position the C-arm may be rotated back to the A/P position while maintaining the radial rotation imparted to achieve the trajectory lateral position. A surgical instrument may be advanced to the target site and positioned on the lateral margin of the pedicle, the preferred starting point according to this example. The depth of penetration of the surgical instrument may be checked during advancement by rotating the C-arm back to a trajectory lateral view.

Alternatively, the starting point may be determined using an "owls eye" view. The C-arm may be oriented such that it is aligned with both the medial-lateral and cranial-caudal angles as discussed above. The tip of the pedicle access instrument is placed on the skin so that the tip is located in the center of the pedicle of interest on the fluoro-image; and thereafter the instrument is advanced to the pedicle. Another fluoro-image is taken to verify that the tip of the instrument is still aligned in the center of the pedicle.

Using the "owls eye" view, a standard surgical instrument may be guided along a pedicle axis without the use of an additional tilt sensor on the surgical instrument. In the "owls eye" image, a surgical instrument properly aligned with the pedicle axis will appear as a black dot. Once aligned, the surgical instrument may be advanced through the pedicle while ensuring that it continues to appear as only a dot on the fluoroscopy image. The depth of penetration may again be checked with a trajectory lateral image.

The surgical trajectory system may also be utilized a surgical access system. Using the surgical trajectory system can aid in both the insertion and positioning of the access instruments themselves, as well as, aiding in the later insertion of instruments and/or implants through the surgical access instruments. One significant advantage is the ability to later visually align surgical instruments and/or implants along the same trajectory by visually comparing the alignment of the instrument to that of the access instrument The Neurophysiologic monitoring may be carried out in conjunction with the trajectory monitoring performed by the surgical trajectory system. The surgical trajectory system may be used in combination with neurophysiologic monitoring systems to conduct pedicle integrity assessments before, during, and after pilot hole formation, as well as to detect the proximity of nerves while advancing and withdrawing the surgical instrument from the pedicle target site. By way of example only, a neurophysiology system is described which may be used in conjunction with the surgical trajectory system.

The neurophysiology system includes a display, a control unit, a patient module, an EMG harness, including eight pairs of EMG electrodes and a return electrode coupled to the patient module, and a host of surgical accessories (including an electric coupling device) capable of being coupled to the patient module via one or more accessory cables.

To perform the neurophysiologic monitoring, the surgical instrument is configured to transmit a stimulation signal from the neurophysiology system to the target body tissue (e.g. the pedicle). As previously mentioned, the surgical instrument probe members may be formed of material capable of conducting the electric signal. To prevent shunting of the stimulation signal, the probe members may be insulated, with an electrode region near the distal end of the probe member for delivering the electric signal and a coupling region near the proximal end of the probe member for coupling to the neurophysiology system.

The neurophysiology system performs nerve monitoring during surgery by measuring the degree of communication between a stimulation signal and nerves or nerve roots situated near the stimulation site. To do this, the surgical instrument is communicatively linked to the neurophysiology monitoring system and stimulation signals are emitted from an electrode region on the surgical instrument. EMG electrodes positioned over the appropriate muscles measure EMG responses corresponding to the stimulation signals. The relationship between the EMG responses and the stimulation signals are then analyzed and the results are conveyed to the practitioner (e.g. audibly and/or visually on the neurophysiology display). More specifically, the system determines a threshold current level at which an evoked muscle response is generated (i.e. the lowest stimulation current that elicits a predetermined muscle response). Generally the closer the electrode is to a nerve, the lower the stimulation threshold. Thus, as the probe member moves closer to a nerve, the stimulation threshold will decrease, which may be communicated to the practitioner to alert him or her to the presence of a nerve. The pedicle integrity test, meanwhile, works on the underlying theory that given the insulating character of bone, a higher stimulation current is required to evoke an EMG response when the stimulation signal is applied to an intact pedicle, as opposed to a breached pedicle. Thus, if EMG responses are evoked by stimulation currents lower than a predetermined safe level, the surgeon may be alerted to a possible breach.

In one embodiment, the tilt sensor may be communicatively linked directly to the control unit of the neurophysiology monitoring system and data from the tilt sensor may audibly communicated and/or visually communicated alone and/or jointly with the neurophysiologic data.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 17 illustrates the position of the display unit of FIG. 16 relative to the manipulating hand of the practitioner, according to one embodiment of the present invention;

FIGS. 18A-18B are front and side views, respectively, of the display unit of FIG. 15 attached directly to the practitioner's manipulating hand, according to another embodiment of the present invention;

FIG. 36 is a side view of the coupler/tilt sensor combination of FIG. 35 attached to a signal receiver of the C-arm of FIG. 26 in the A/P position, according to one embodiment of the present invention;

FIG. 37 is a side view of the coupler/tilt sensor combination of FIG. 35 attached to a signal receiver of the C-arm of FIG. 26 in the lateral position, according to one embodiment of the present invention;

FIG. 46 is a front view of the coupler of a coupler for coupling the surgical trajectory system of FIG. 1 to the C-arm of FIG. 6, the coupler including 4 radio-dense markers positionable over the signal receiver, according to another embodiment of the present invention;

FIG. 47 is a front view showing a surgical table rotated laterally to adjust the orientation of the C-arm of FIG. 26 with respect to the patient, according to another embodiment of the present invention;

FIG. 48 is a side view showing a surgical table rotated in the sagittal plane to adjust the orientation of the C-arm of FIG. 26 with respect to the patient, according to another embodiment of the present invention;

DESCRIPTION OF THE PREFERRED EMBODIMENT

Figure 1:
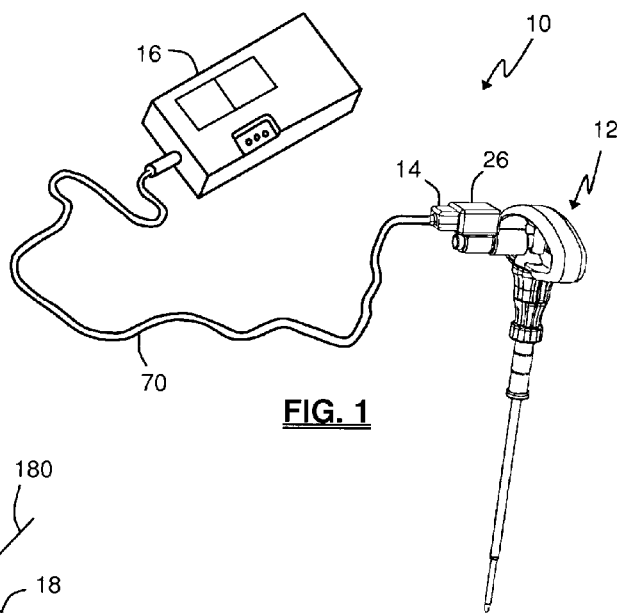
FIG. 1 is an exemplary view of a surgical trajectory system, including a tilt sensor and an LCD feedback device, connected to a surgical instrument, according to one embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Various embodiments are described of a trajectory monitoring system and surgical uses thereof for enhancing the safety and efficiency of surgical procedures. In one example, set forth by way of example only, the present invention may facilitate safe and reproducible pedicle screw placement by monitoring the axial trajectory of various surgical instruments used during pilot hole formation and/or screw insertion. In another example, set forth by way of example only, intraoperative imaging performance may be improved and radiation exposure minimized by monitoring the precise orientation of the imaging device. In yet another example, monitoring the orientation of surgical access instruments can aid in both the insertion and positioning of the access instruments themselves, as well as, aiding in the later insertion of instruments and/or implants through the surgical access instruments. While the above examples are described in more detail below, it is expressly noted that they are set forth by way of example and that the present invention may be suitable for use in any number of additional surgical actions where the angular orientation or trajectory of instrumentation and/or implants is important. By way of example only, the present invention may be useful in directing, among other things, the formation of tunnels for ligament or tendon repair and the placement of facet screws. Accordingly, it will be appreciated then that while the surgical trajectory system is generally discussed herein as being attached to instruments such as pedicle access tools, C-arms, dilating cannulas, and tissue retractors, other instruments (e.g. drills, screw drivers, taps, inserters, etc. . . . ) may be substituted depending on the surgical procedure being performed and/or the needs of the surgeon. In a further aspect of the present invention, the trajectory monitoring system may be used in conjunction with, or integrated into, a neurophysiology system for assessing one or more of pedicle integrity and nerve proximity, among others functions, as will be described below.

Details of the surgical trajectory system are discussed in conjunction with a first exemplary use thereof for monitoring pilot hole formation (and/or screw insertion) during pedicle screw placement. As used herein, pilot hole formation is meant to encompass any of, or any combination of, creating a hole in bone (such as, for example only, by awling, boring, drilling, etc. . . . ) and preparing a previously formed hole (such as, for example only, by tapping the hole).

With reference now to FIG. 1, there is shown, by way of example only, one embodiment of a surgical trajectory system 10 engaged with a surgical instrument 12 for accessing a pedicle. The surgical trajectory system 10 comprises an angle-measuring device (hereafter "tilt sensor") 14 and a feedback device 16. The tilt sensor 14 measures its own angular orientation with respect to a reference axis, such as vertical or gravity. The feedback device 16 displays the angle measurements obtained by the tilt sensor 14 for reference by a practitioner. By attaching the tilt sensor 14 to a surgical instrument in a known positional relationship, the angular orientation of the instrument may be determined with respect to the same reference axis. This enables the surgeon to position and maintain the instrument 12 along a desired trajectory path during use. For example, during pilot hole formation, surgical instrument 12 may be aligned and advanced along a pre-determined pedicle axis, thereby decreasing the risk of breaching the pedicle wall.

Figure 2:
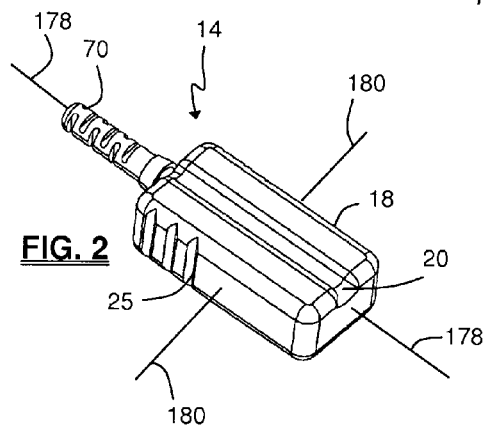
FIG. 2 is a perspective view of a tilt sensor of the surgical trajectory system of FIG. 1, according to one embodiment of the present invention.
Figure 3:
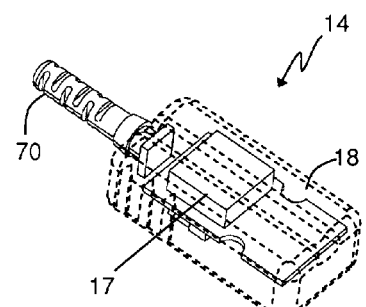
FIG. 3 is a perspective view of a tilt sensor, the outer housing shown in dashed lines to make visible the inclinometer situated within the housing, according to one embodiment of the present invention.
Figure 4:
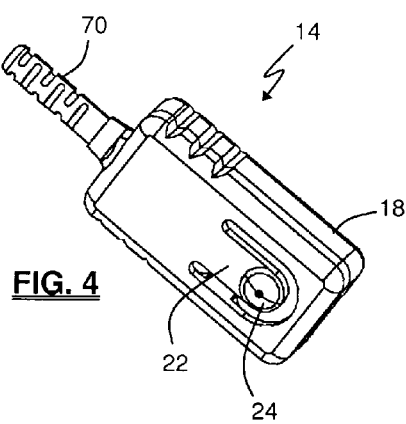
FIG. 4 is a perspective view depicting the bottom of the tilt sensor, according to one embodiment of the present invention.
Figure 5:
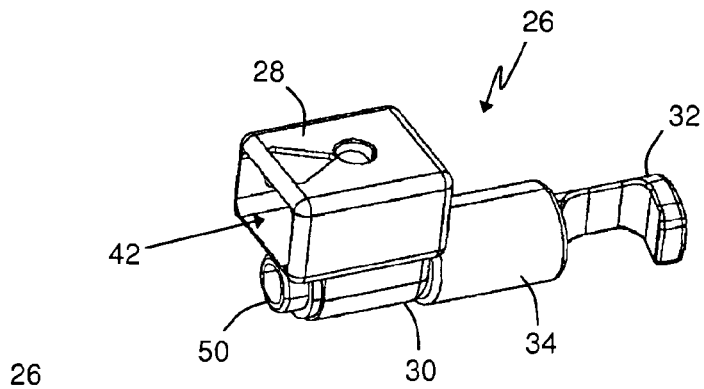
FIGS. 5-7 illustrate a universal clip connector used to attach the tilt sensor of FIG. 2 to a surgical instrument, according to one embodiment of the present invention.
Figure 6:
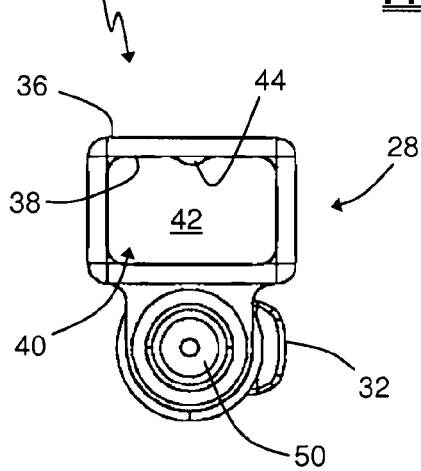
Figure 7:
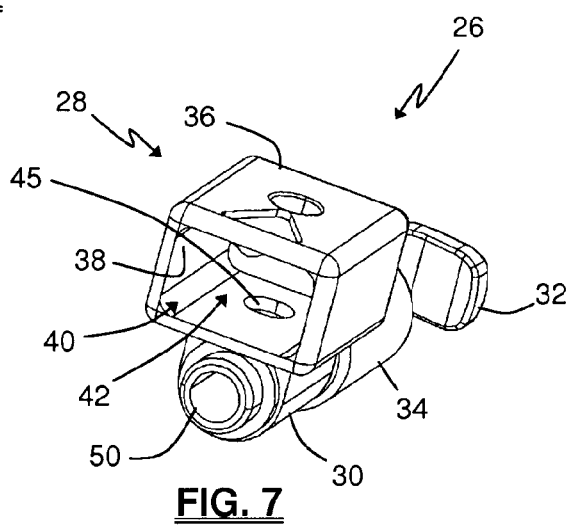
Figure 8:
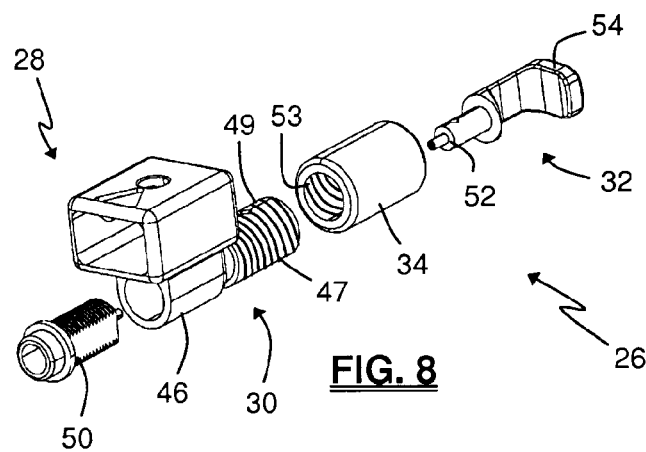
FIG. 8 is an exploded view of the universal clip connector of FIGS. 5-7, according to one embodiment of the present invention.
Figure 9:
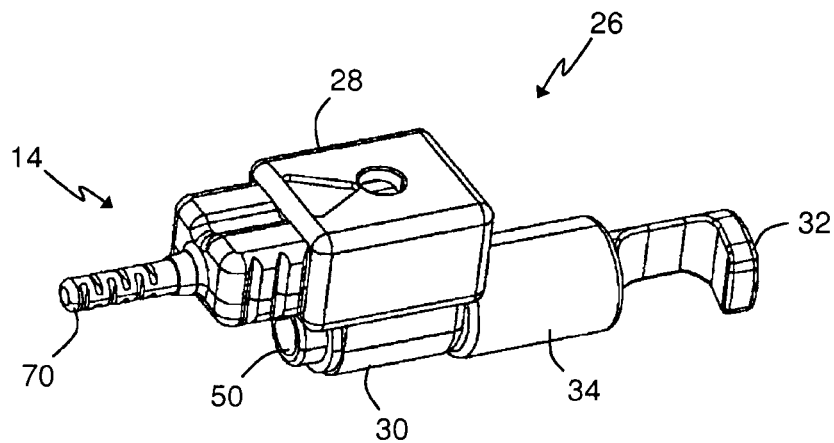
FIG. 9 is a perspective view of the tilt sensor mated with the universal clip, according to one embodiment of the present invention.

Tilt sensor 14, illustrated in FIGS. 2-4, includes a sensor package 17 (FIG. 3) enclosed within a housing 18. The housing 18 may be made from a surgical grade plastic, metal, or any material suitable for use in the surgical field. Housing 18 may be dimensioned to snugly mate with a universal clip 26, described below, for attaching tilt sensor 14 to surgical instrument 12. As shown herein, housing 18 has a generally rectangular box shape. However, it should be understood that housing 18 may be provided in any suitable shape having any suitable cross-section (e.g. generally ellipsoidal, triangular, or other polygonal shape), provided that the sensor package 17 inside the housing may be positioned such that it is oriented orthogonally relative to the direction of gravity, without deviating from the scope of the invention. An alignment groove 20, shown by way of example only on the top of housing 18 in FIG. 2, may be provided to assist in properly positioning tilt sensor 14 relative to the instrument 12. Specifically, groove 20 cooperates with a complementary structure, such as alignment ridge 44 on the universal clip 26 (FIG. 6) such that the tilt sensor 14 may only attach to the clip in a single, known orientation. An engagement tab 22, shown by way of example only on the bottom of housing 18 in FIG. 4, may be included to assist in securing tilt sensor 14 to universal clip 26, thereby preventing movement and/or dislodgment of the tilt sensor 14. One or more additional grooves 25 may be included on housing 18 to provide increased grip during handling (e.g. during insertion and removal of the tilt sensor 14). In another embodiment, (not shown) the tilt sensor 14 may be permanently attached to the instrument 12. In still another embodiment (not shown) the tilt sensor may be integrated within the instrument.

In one embodiment, sensor package 17 comprises a 2-axis accelerometer that measures angular orientation with respect to the acting direction of gravity. The angular orientation of tilt sensor 14 is measured in a sagittal plane and a transverse plane. By way of example, the orientation of the tilt sensor 14 in the sagittal plane represents a cranial-caudal angle $A2(i)$ with respect to the direction of gravity and the patient. Orientation in the transverse plane represents a medial-lateral angle $A1(i)$ with respect to a patient and the direction of gravity. Sensor package 17 is preferably situated within housing 18 such that when housing 18 is perpendicular to the direction of gravity, the accelerometer registers zero angle in both the sagittal and transverse planes (i.e. the zero-angle position or $A1(i)=0$ and $A2(i)=0$). In other words, both the cranial-caudal angle and medial-lateral angle are equal to zero. Thus, when tilt sensor 14 is fixed perpendicular to the longitudinal axis of the surgical instrument 12, the angular orientation of the instruments longitudinal axis may be determined relative to gravity.

Utilizing only a 2-axis accelerometer, the accuracy of the tilt sensor 14 may be adversely affected by movement around the third, rotational axis. To counter this, measurements should preferably be taken only when at least one of the longitudinal axis 178 and transverse axis 180 tilt sensor 14 are aligned with a selected reference frame, such as for example, the longitudinal axis of the patient's spine (i.e. the tilt sensor 14 should be in approximately the same rotational alignment for every measurement). In one embodiment, this may be accomplished effectively using visual aids to help keep the tilt sensor 14 in line with the reference frame and/or ensure measurements may be taken only when the tilt sensor 14 appears to be in this correct rotational position. In the event the surgical instrument 12 is inadvertently or purposely rotated during use, the practitioner need only continue, or reverse rotation until the tilt sensor 14 again appears to be perpendicular to the long axis of the spine. Alternatively (or in addition to), various markings or other indicia (not shown) may be included on one or more of the tilt sensor 14, the surgical instrument 12, and the universal clip 26, to ensure proper alignment prior to obtaining measurements.

In an alternative embodiment, the sensor package 17 may be configured such that it may account for, or at least measure, rotation (e.g. a "3-axis sensor"). In one embodiment, the sensor package 17 includes a 2-axis accelerometer augmented by a gyroscope (not shown), which may comprise any number of commercially available gyroscopes. While the accelerometer again measures the angular orientation of the tilt sensor 14 with respect to gravity, the gyroscope detects movement about the rotational or z-axis. By monitoring the rate of rotation and time, the system 10 may determine the degrees of rotation imparted on the surgical instrument (and tilt sensor 14). The feedback device 16 may indicate to the user that the sensor 14 is not aligned in the correct reference frame such that the user may take steps to correct the alignment prior to taking measurements. The feedback device 16 may display feedback according to any number of suitable methods. By way of example, the feedback may utilize numeric indicia to indicate the degree of misalignment, color indicia, such as red or green indicating the rotational status (e.g. aligned or misaligned), audible alert tones (e.g. low frequency tones for non-alignment and high frequency tones for proper alignment or visa versa or any combination thereof), etc. . . . Alternatively, the system 10 may be configured to correct the angle data output based on the degree of rotation detected. In this manner, angle data from the tilt sensor may be acquired from any rotational position. A button (not shown) may be provided on the tilt sensor 14 and/or feedback device 16 to initially zero the sensor package 17 when it is aligned with the reference frame.

In another embodiment, the sensor package 17 accounts for rotational movement by utilizing magnetometers (not shown) in conjunction with the 2-axis accelerometers, where the magnetometer may comprise any number of commercially available magnetometers. The sensor package 17 includes a triplet of magnetic sensors oriented perpendicular to each other, one pointing in the x-axis, one in the y-axis, and third pointing in the z-axis. The magnetic sensors in the x and y axis act as a compass and calculate a heading of tilt sensor 14 relative to magnetic north. The third magnetometer in the z-axis and the x and y axis accelerometers monitor the tilt permitting the "compass" to work when it is not level to the ground. Since the sensor package 17 monitors for angular orientation in the x-axis and y-axis and maintains a constant heading reference, the system 10 may calculate the amount of axial rotation relative to an established reference frame (i.e. the patient). The feedback device 16 may again be configured to indicate the rotational status of the tilt sensor 14 to the user, allowing them to realign the sensor 17 with the proper reference frame prior to establishing a reading. The feedback device 16 may again utilize numeric indicia to indicate the degree of misalignment, color indicia, such as red or green indicating the rotational status (e.g. aligned or misaligned), audible alert tones (e.g. low frequency and/or volume tones for non-alignment and high frequency and/or volume tones for proper alignment or visa versa or any combination thereof), etc. . . .

With reference to FIGS. 5-10, there is shown one example of a universal clip 26 for mating tilt sensor 14 to the surgical instrument 12. Universal clip 26 comprises a sensor bed 28, a coupler 30, a fastener 32, and a collar 34. Sensor bed 28 has an exterior surface 36, an interior surface 38, and an opening 40. Interior surface 36 and opening 40 collectively form cavity 42. Sensor bed 28 is generally rectangular in shape, however, it should be understood that sensor bed 28 may be provided in any suitable shape having any suitable cross-section (e.g. generally ellipsoidal, triangular, or other polygonal shape) to receive the tilt sensor 14 therein in a known orientation. Cavity 42 is dimensioned to snugly receive at least a portion of tilt sensor 14. An alignment ridge 44 may be provided along an upper region of interior surface 38 of cavity 42, shown by way of example only along the top, to ensure tilt sensor 14 is positioned properly within the cavity 42 (e.g. with the top surface of housing 18 adjacent to the upper region of the interior surface 38). Alignment ridge 44 is complementary to alignment groove 20 on the tilt sensor housing 18. In order to insert the tilt sensor 14 in cavity 42, the alignment ridge 44 and alignment groove 20 must be aligned. Thus, tilt sensor 14 may preferably only fit together with the sensor bed 28 in a single, known orientation. To secure the tilt sensor 14, a hole 45 is provided within a lower region of the interior surface 38 (FIG. 7), which receives a complementary protrusion 24 situated on engagement tab 22 of sensor housing 18. When the tilt sensor 14 is fully inserted into cavity 42, protrusion 24 becomes seated in hole 45, thereby preventing the unintentional disengagement of tilt sensor 14 from the sensor bed 28. It should be understood that various other retaining mechanisms (not shown) may be used in place of, or in addition to, the protrusion/hole engagement described above. Other retaining mechanisms may include, but are not necessarily limited to, a ball-spring mechanism and a clasp.

Sensor bed 28 is attached to coupler 30. For stability, sensor bed 28 and coupler 30 may preferably be formed of a single member. Coupler 30 comprises a generally tubular member including a first hollow portion 46 and a second hollow portion 47. First hollow portion 46 attaches to sensor bed 28 and retains a receptacle 50. Second hollow portion 48 retains an engagement end 52 of fastener 32. The receptacle 50 and engagement end 52 may be communicatively linked within coupler 30. The second portion 48 preferably has external threading 49 that is complementary to internal threading 53 on collar 34, allowing the collar 34 to move laterally along the second portion by twisting the collar 34. The free end 54 of fastener 32 is configured to tightly grasp instrument 12. By way of example only, the free end may comprise a hook. If neurophysiology monitoring is to be used, as described below, receptacle 50 can be employed to couple the universal clip 26 to a neurophysiology monitoring system. Because the receptacle 50 and fastener 32 are communicatively linked within coupler 30, stimulation signals may be passed from the neurophysiology monitoring system to the instrument 12.

Figure 10A:
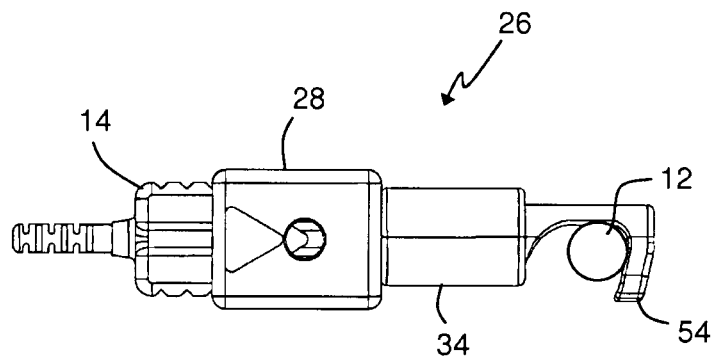
FIGS. 10A-10B illustrate a way in which the universal clip may securely couple a surgical instrument, according to one embodiment of the present invention.
Figure 10B:
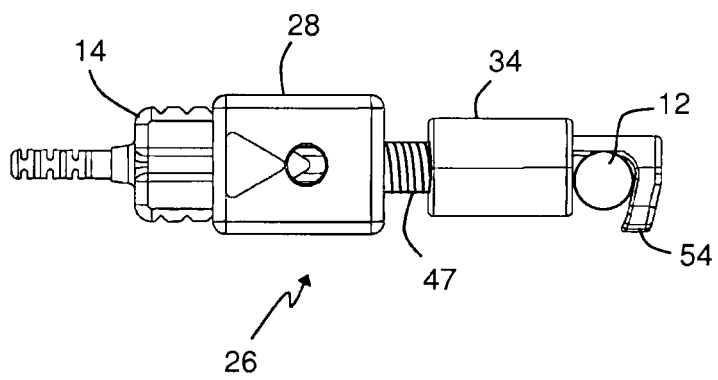

With reference to FIGS. 10A-10B, to secure a surgical instrument 12 to universal clip 26, a portion of surgical instrument 12 (shown in cross-section) is positioned within the hook of free end 54 (FIG. 10A). Collar 34 may then be twisted in a first direction to laterally displaced collar 34 toward the free end 54 so as to capture surgical instrument 12 between the collar 34 and free end 54 (FIG. 10B). When fully tightened, universal clip 26 is securely fastened to instrument 12 and extends perpendicular to the longitudinal axis of surgical instrument 12. When tilt sensor 14 is engaged with clip 26, tilt sensor 14 also extends perpendicular to the longitudinal axis of instrument 12. To release the surgical instrument 12, collar 34 may be twisted in the opposite direction (FIG. 10A).

Figure 11:
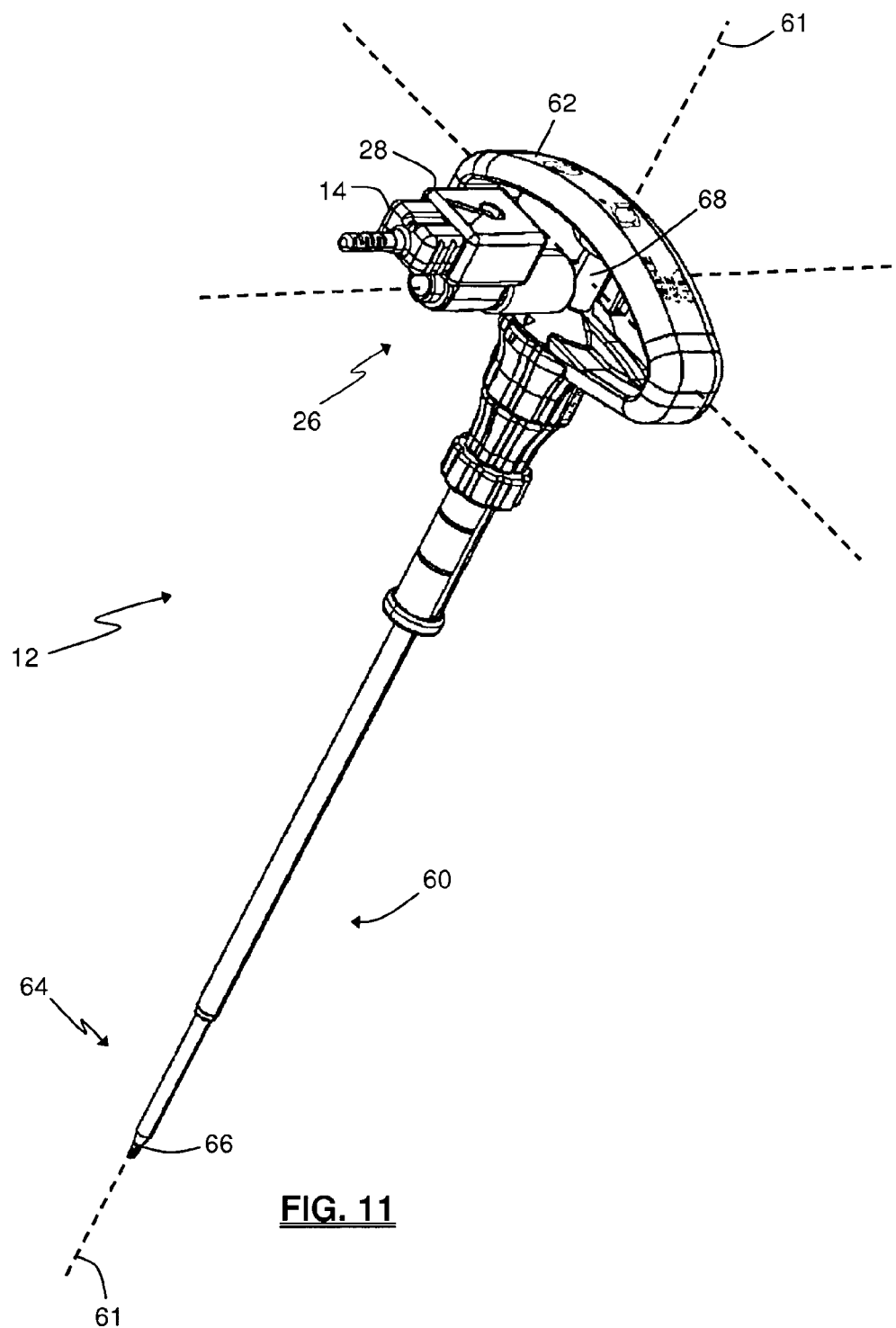
FIG. 11 is a perspective view of a surgical instrument (e.g. jamsheedi needle) for penetrating pedicle bone to form a pilot hole, which is linked to the surgical trajectory system of FIG. 1, according to one embodiment of the present invention.

A surgical instrument 12, according to one embodiment, is illustrated in FIG. 11. Surgical instrument 12 may comprise a pedicle access probe. By way of example only, instrument 12 may be any of the insulated pedicle access probes described in detail in the commonly owned and co-pending U.S. patent application Ser. No. 11/448,237, entitled "Insulated Pedicle Access System and Related Methods," and filed on Jun. 6, 2006, the entire contents of which is incorporated by reference as if set forth herein in its entirety. Instrument 12 comprises generally a probe member 60, having a longitudinal axis 61, and a handle 62. Probe member 60 may be embodied in any variety of configurations that can be inserted through an operating corridor to a pedicle target site and bore, pierce, or otherwise dislodge and/or impact bone to form a pilot hole for pedicle screw placement. Probe member 60 may be generally cylindrical in shape, however, probe member 60 may be provided in any suitable shape having any suitable cross-section (e.g. generally oval, polygonal, etc. . . . ). A distal region 64 of probe member 60 may have a shaped tip 66 formed of any number of shapes generally suited to effect pilot hole formation, such as, by way of example only, a beveled point, double diamond, drill bit, tap, and a generally tapered awl. A proximal region 68 of probe member 60 may be configured to couple with universal clip 26. Probe member 60 may be composed of any material suitable for surgical use and strong enough to impact bone to form a pilot hole. In one embodiment, the material may also be capable of conducting an electric current signal to allow for the use of neurophysiologic monitoring. By way of example only, probe member 60 may be composed of titanium, stainless steel, or other surgical grade alloy.

Handle 62 may be permanently or removably attached to probe member 60 along the proximal region 68. Handle 62 may be shaped and dimensioned in any of a number of suitable variations to assist in manipulating probe member 60. By way of example only, the handle 62 may be generally T-shaped such as the handle pictured in FIG. 11. Other suitable shapes for handle 62 may include, but are not necessarily limited to, generally spherical, ellipsoidal, and egg-shaped. Universal clip 26 may preferably grasp the proximal end 68 of probe member 60 through a cutout in the handle 62. If the handle does not have a cutout the universal clip 26 may attach to the probe member 60 below the handle 62. Universal clip 26 forms a sturdy connection with probe member 60 such that the tilt sensor 14 is maintained in a position perpendicular to the longitudinal axis 61 of probe member 60. When the longitudinal axis 61 of probe member 60 is parallel to the direction of gravity, the tilt sensor 14 is perpendicular to the direction of gravity (i.e. the zero-angle position). In other words, when the longitudinal axis 61 of probe member 60 is parallel to the acting direction of gravity, both the cranial-caudal angle and the medial-lateral angle will be zero-degrees.

Figure 12:
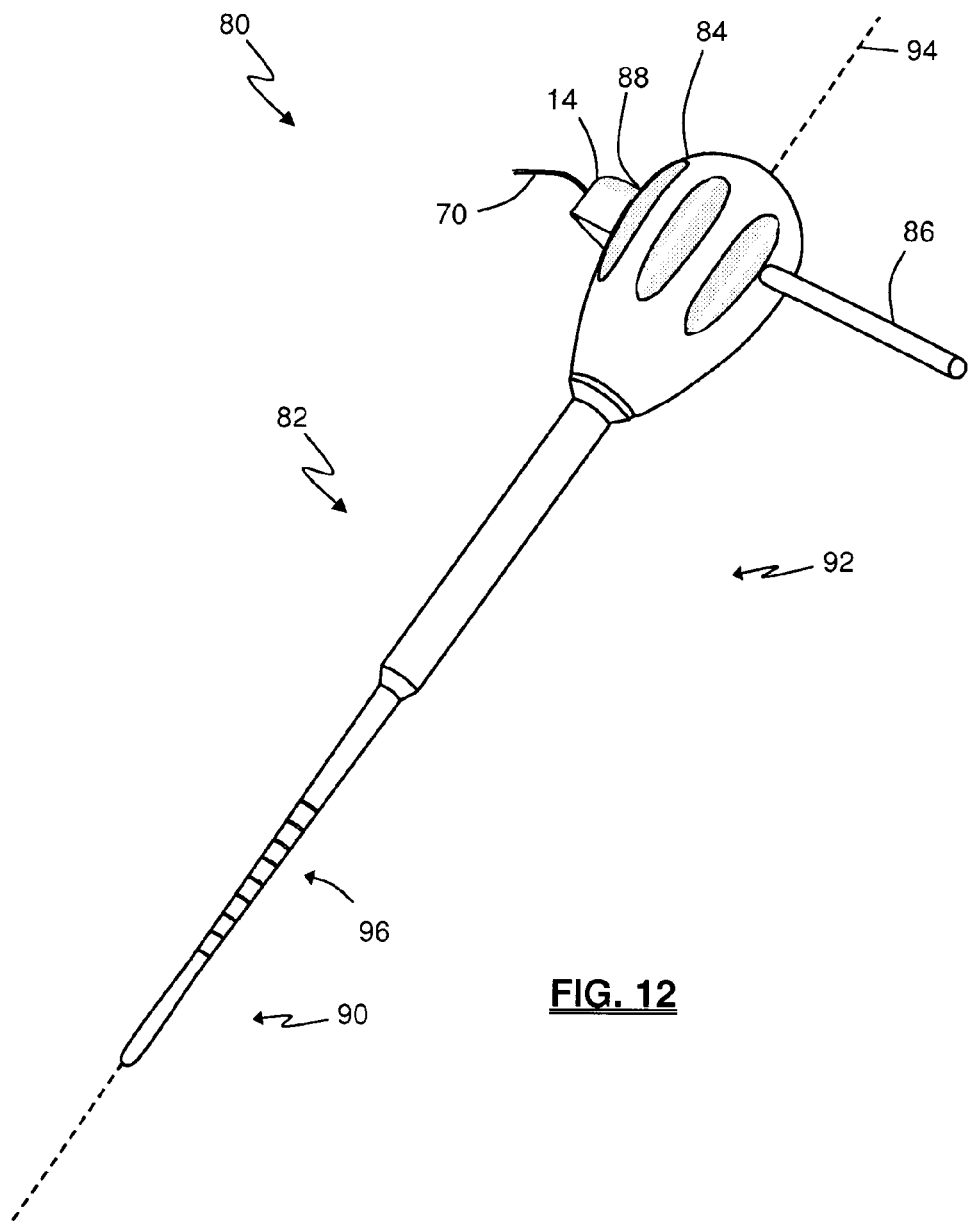
FIG. 12 is a perspective view of a surgical instrument (e.g. gear shift probe) for penetrating pedicle bone to form a pilot hole, which is linked to the surgical trajectory system of FIG. 1, according to another embodiment of the present invention.

With reference to FIG. 12, there is shown another example of a pedicle access instrument that may be used with the surgical trajectory system 10. Surgical instrument 80 is similar to a standard gearshift probe, which are commonly used to create holes in pedicle bone, modified for direct engagement with the tilt sensor 14. Surgical instrument 80 comprises a probe member 82, a handle 84, an orientation shaft 86, and a sensor cavity 88 for receiving and holding a tilt sensor 14. Probe member 82 may be generally cylindrical in shape and include a distal end 90, a proximal end 92, and a longitudinal axis 94 extending through distal and proximal ends 90, 92, respectively. However, it should be understood that probe member 82 may be provided in any suitable shape having any suitable cross-section (e.g. generally oval, polygonal, etc. . . . ). The distal end 90 may have a shaped end comprising any of a number of forms generally suited to effect pilot hole formation such as (by way of example only) a beveled point, drill bit, or as shown in FIG. 12, an awl with a generally tapered shape. Probe member 82 may be composed of, by way of example only, titanium, stainless steel, or other material strong enough to impact bone to form a pilot. In one embodiment the material of probe member 82 is capable of conducting an electric signal for employing neurophysiologic monitoring, as described below. Probe member 82 may include one or more markings 96 about the exterior surface that can be viewed to indicate the depth of penetration in a pedicle target site.

Handle 84 may be permanently or removably attached to probe member 82 at the proximal end 92. Handle 84 may be shaped and dimensioned in any of a number of suitable variations to assist in manipulating probe member 82. By way of example only, the handle 84 may be generally spherical shaped, T-shaped, or egg shaped, to name a few. With further reference to FIG. 12, an orientation shaft 86 may be positioned on handle 84. Orientation shaft 86 extends from handle 84 perpendicularly to the longitudinal axis 94 of the probe member 82. The handle 84 also includes a sensor cavity 88. The sensor cavity 88 functions to receive and hold the tilt sensor 14 in proper position relative to the probe member 82. The sensor cavity 88 may preferably be dimensioned to snugly receive at least a portion of the tilt sensor 14, thereby preventing movement of the tilt sensor 28 within the cavity 88. One or more mechanisms may be provided on the tilt sensor 14 and/or on or within the sensor cavity 88 to secure the tilt sensor 14 in position. Preferably, sensor cavity 88 may include a hole or recess (not shown) for capturing the protrusion 24 on tilt sensor 14, described above. Other such mechanisms may include, but are not necessarily limited to, a ball-spring mechanism and a clasp mechanism Orientation shaft 86 may be provided as a visual marker to assist in aligning the tilt sensor 14 and surgical instrument 80 with the proper reference frame (as described above) when obtaining angle measurements. Similar to that described above with reference to the universal clip 26, the orientation shaft 86 may be aligned, by way of example only, perpendicular to the longitudinal axis of the spine when a measurement is read. Again this eliminates the risk of inaccurate angle measurements due to rotational movement of the surgical instrument when a t-axis accelerometer is utilized.

Figure 13:
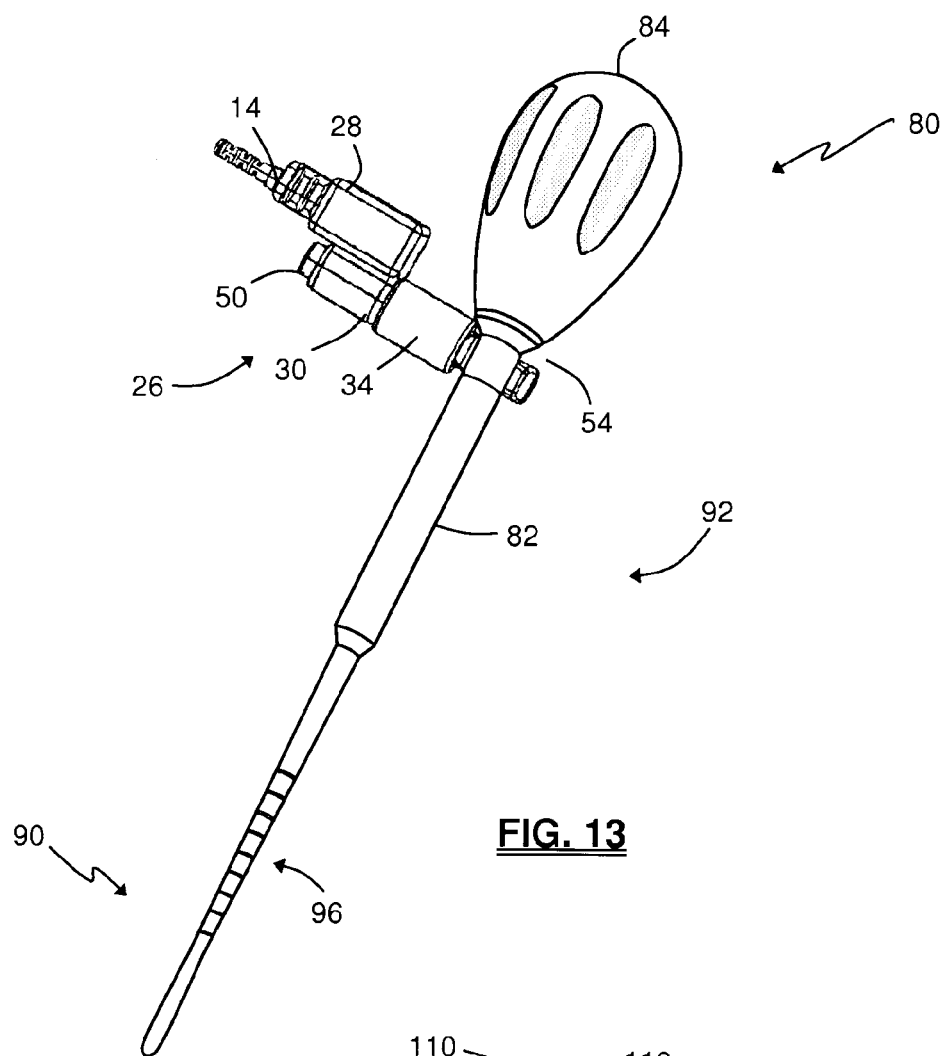
FIG. 13 is a perspective view of the surgical instrument of FIG. 12 coupled to the surgical trajectory system by a universal clip as opposed to the direct coupling seen in FIG. 12, according to yet another embodiment of the present invention.

In an alternate embodiment, the surgical instrument 80 may be provided without sensor cavity 88. Instead, the universal clip 26 may attach to probe member 82, as illustrated in FIG. 13. In another alternate embodiment, (not shown) the tilt sensor 14 may be permanently attached to the handle 80. In still another embodiment (not shown) the tilt sensor may be integrated within the instrument 80.

Figure 14:
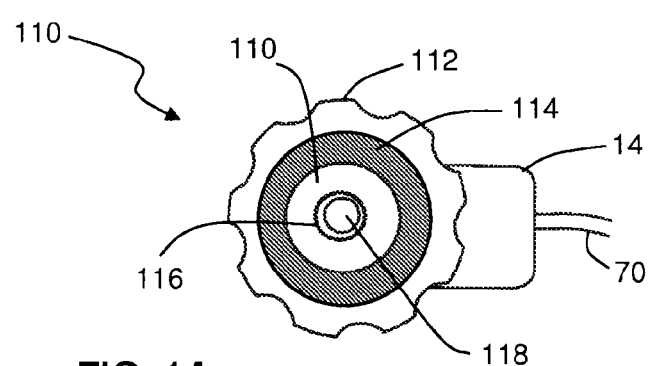
FIG. 14 is a top view of a bubble level device optionally provided with the tilt sensor, according to one embodiment of the present invention.

With reference to FIG. 14, a bubble level device 110 may be used to ensure the tilt sensor 14 is functioning correctly. The bubble level device 110 includes a handle 112 with a level 114 mounted in it. The tilt sensor 14 is inserted into the handle 112, which then is placed on a flat surface so that an indicator ring 116 on the domed transparent surface 117 of level 114 encircles the bubble 118 captured within the domed surface 117. When the bubble 118 is within the indicator ring 116, the tilt sensor display should read approximately zero-degrees for both the cranial-caudal readout 99 and medial-lateral readout 98.

Figure 15:
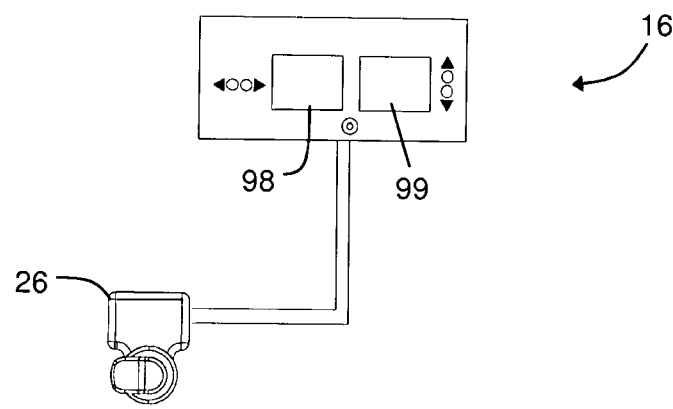
FIG. 15 is an exemplary display unit, releasably or permanently coupled to the universal clip, such that the display feedback may be viewed in the surgical field, according to one embodiment of the present invention.

Regardless of the manner of coupling the tilt sensor 14 to the respective instrument (e.g. probe 12, gear shift 80, or any other instrument), the feedback device 16 is communicatively linked to tilt sensor 14 to provide feedback to the surgeon regarding angle of the tilt sensor 14 and instrument relative to the desired angles (medial-lateral and cranial-caudal). This communication link may be accomplished via hard-wire (e.g. data cable 70 of FIG. 1) and/or via wireless technology, in which case the tilt sensor 14 and feedback device 16 may include additional hardware commonly used for enabling such wireless communication. The feedback device 16 may be a computer or similar type processing unit (not shown). User input may be directed to the trajectory system 10 through feedback device 16. In one embodiment, shown in FIG. 15, feedback device 16 includes an LCD display with at least one numerical readout 98 for presenting the medial-lateral angle determined by the tilt sensor 14 and at least one numerical readout 99 for presenting the cranial-caudal angle determined by the tilt sensor. Readouts 98 and 99 may be displayed in a single window or on separate windows designated for each readout. In one embodiment, the medial-lateral and cranial-caudal readouts 98, 99 are displayed simultaneously and continuously while the tilt sensor 14 is in use. If only one window is provided, a switch or button for toggling between the two angle measurements may be utilized (not shown). The feedback device 16 may be placed next to the patient on the surgical table, or it may be affixed to any number of suitable objects in the operating room, including, but not necessarily limited to, an IV pole, surgical table, prep table, fluoroscope, neurophysiologic monitoring system, etc. . . . If communicatively linked to the feedback device 16 via hard-wire, the position of the feedback device 16 should be such that the tilt sensor 14 may move freely without tensioning the data cable 70.

Figure 16:
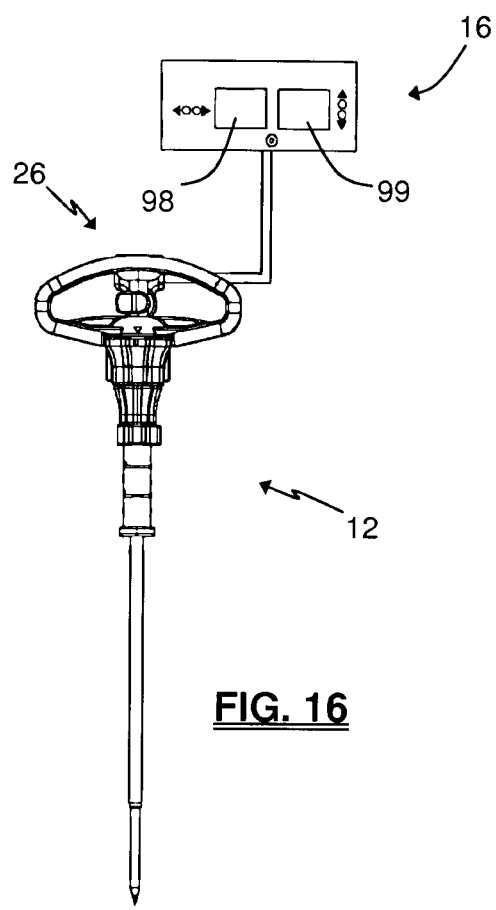
FIG. 16 is a front view of the display unit of FIG. 15, engaged to a surgical instrument, according to one embodiment of the present invention.

At times it may not be convenient for the surgeon to look away from the surgical field to view the angle measurements displayed by the surgical trajectory system 10. According to one embodiment, shown in FIGS. 15-16, this may be accomplished by providing the feedback device 16 having a smaller, thinner and/or miniaturized size relative to that shown in FIG. 1. By providing the feedback device in the manner shown in FIGS. 15-16, the practitioner may be able position the feedback device 16 close to his or her hand so as have the displays 98, 99 both in their general field of view while using the surgical trajectory system 10. For example, with reference to FIG. 17, the feedback device 16 may be coupled to the instrument 12 via a universal clip 26 such that it rests above and slightly offset from the practitioner's hand, thus maintaining the feedback device 16 in the surgical field without obstructing the surgeon's view of the operative site. By way of another example, with reference to FIGS. 18A-18B, feedback device 16 may be positioned on the back of the hand of the practitioner, which may be augmented via a strap 102. Again, this advantageously positions the feedback device 16 in the surgical field without obstructing the surgeon's view of the operative site.

It is further contemplated that feedback device 16 may be configured to provide feedback based on indicia other than numerical readouts 98, 99. By way of example, feedback device 16 may utilize a code based on the expression of color to indicate the angular orientation of the tilt sensor 14 and also thus, the orientation of the instrument to which it is attached. One such color code scheme will display the color red when the angles of the tilt sensor 14 fall outside an acceptable range from the correct orientation, the color yellow when the angles of the sensor 14 are close to the correct range but not yet within an optimal orientation range, and the color green when the angles of the tilt sensor 14 are aligned within an optimal orientation range. The correct orientation of the tilt sensor 14 (i.e. whether it is in the "green zone", "yellow zone", or "red zone") may be measured against predetermined angle measurements previously inputted into the system 10 or, against a separate reference marker which is known to be positioned in the correct orientation and is communicatively linked to the trajectory system 10 (e.g. a C-arm as will be described below). A single color display could be used to indicate the overall orientation of the tilt sensor 14, or, individual and independently operated color display could be used to indicate the orientation in the cranial-caudal direction and medial-lateral directions, respectively. Various implementation methods may be utilized to accomplish the display of the color code. By way of example only, the LCD displays could be configured to output a color and change the color according to the code based on input data from the sensor 14. Alternatively, dedicated color displays comprising one of each color in the code may be arranged such that a single color is displayed based upon the input from the sensor 14. Two displays for each color may be utilized in order to show the orientation status of both the cranial-caudal and medial-lateral angles independently. LED lights may be used instead of LCD displays and arranged according to any of the above configurations. Feedback based on color indicia may be used alone or in combination with the numerical data previously described.

By way of another example, the feedback device 16 may utilize a code based on the emission of audio tones to indicate the angular orientation of the tilt sensor 14 relative to predetermined reference angles corresponding to the pedicle axis. One method for implementing an audio code involves varying one or more of the volume, pitch, frequency, pulse rate, and length of the audio tone based on the determined orientation of the sensor 14 relative to the predetermined orientation ranges. Audio feedback may be used alone, or in combination with one or both of the numerical data and color indicia previously described. In one embodiment, a first audible signal may be indicative of an optimal variance between the trajectory of the instrument and at least one of the first and second determined angular relationships between the sensor 14 and said reference direction. A second audible signal may be indicative of an unacceptable variance between the trajectory of the instrument and at least one of the first and second determined angular relationships between the sensor 14 and the reference direction. A third audible signal may be indicative of an acceptable yet not optimal variance between the trajectory of the instrument and at least one of the first and second determined angular relationships between the sensor 14 and the reference direction.

Figure 67:
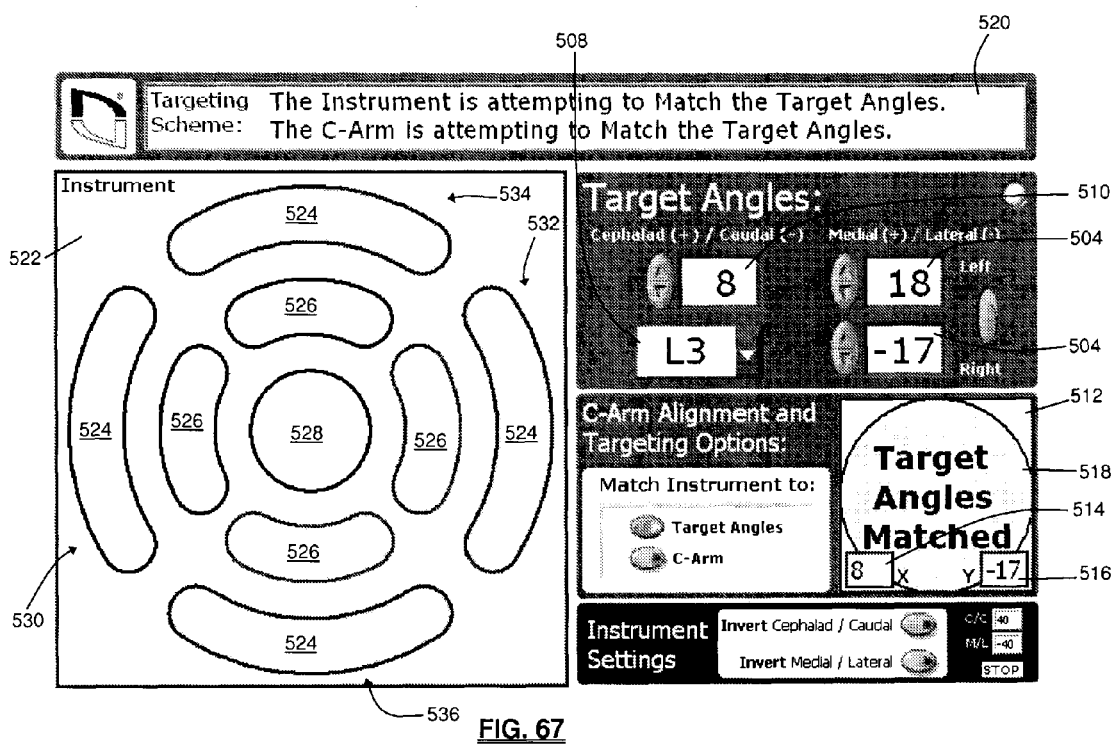
FIG. 67 is an exemplary screen display of the surgical trajectory system 10 incorporating both alpha-numeric and graphical indicia, according to one embodiment of the present invention.
Figure 68:
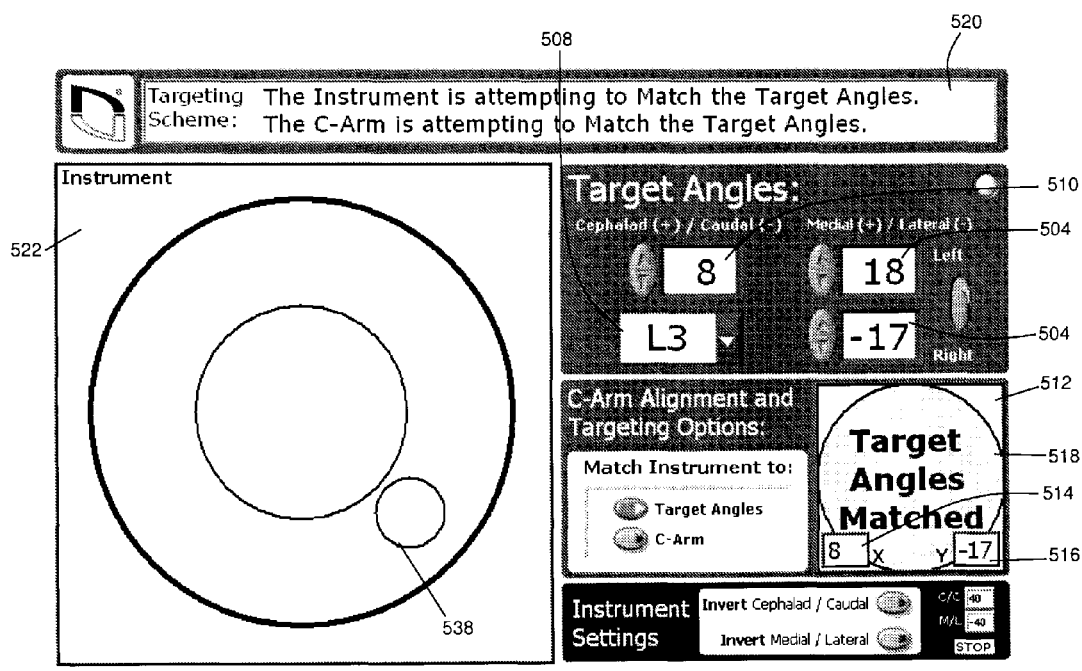
FIG. 68 is an exemplary screen display of the surgical trajectory system 10 incorporating both alpha-numeric and graphical indicia, according to another embodiment of the present invention.

FIGS. 67-68 illustrate, by way of an example only, embodiments of a screen display 500 capable of receiving input from a user in addition to communicating feedback to the user. The screen display 500 incorporates both alpha-numeric and color indicia as described above. In this example (though it is not a necessity) a graphical user interface is utilized to enter data directly from the screen display. By way of example, measurements obtained for the medial-lateral angle A1 may be entered into input boxes 504 and 506 for (for left and right pedicles, respectively). The data may be entered for each spinal level of interest by selecting the appropriate level from a menu 506 and then entering the correct values into boxes 504 and 506. The entered values may be saved by the system such that during the procedure selecting the spinal level from menu 510 automatically recalls the inputted values. A box 508 is provided for inputting the cranial-caudle angle A2 determined for each level. A C-arm window 512 contains data pertaining to a second tilt sensor 14 positioned on a fluoroscopic imager, as is described in more detail below. By way of example numeral boxes 514 and 516 display the numeric values determined by the C-arm tilt sensor 14. When the numeric values corresponding to the C-arm sensor matches within an accepted range the predetermined target angles the C-arm window 512, or a portion there of (such as the circle 518) may be saturated with the color green. Alphanumeric characters may also visually indicate that the target angles have been matched by the C-arm. If the c-arm is aligned with the pedicle axis (placed in the owls' eye view) as is later described, the C-arm values A1($c$) and A2($c$) should approximate the pedicle axis angles A1 and A2. The user may have the option to base feedback from the instrument 12, 80 mounted tilt sensor 14 (e.g. red, yellow, green indicia, etc. . . . ) on matching the C-arm sensor values, rather than the predetermined target values. This option may be exercised, by way of example only, by selecting the appropriate button in the C-arm window 512. A status bar 520 may be provided to indicate the relative status of both the instrument 12, 80 and C-arm tilt sensors. By way of example only, the status bar 520 depicted in FIGS. 67 and 68 indicate that both the instrument 12, 80 and the C-arm sensors are attempting to match the targeted angles. Other messages (not shown) may indicate for example, that the instrument 12, 80 is trying to target the C-arm angles, that the target angles are matched, or that a sensor is not in use. FIGS. 67-68 depict varying embodiments of an instrument window.

The instrument window embodied in FIG. 67, employs a color coded target. The outer rings 524 of the target may be red. The middle rings 526 of the target may be yellow, and the inner circle 528 may be green. When the instrument is aligned with the target angles center circle may be saturated green, indicating that both the medial-lateral angle A1 and cranial-caudal angles have been matched, or A1=A1($i$) and A2=A2($i$). Similarly if the instrument 12, 80 is matched to the C-arm (A1($c$)=A1($i$) and A2($c$)=A2($i$)) the center circle may be saturated green. The middle 526 and outer 524 rings may be divided into quadrants 530, 532, 534, and 536 corresponding to right, left, cranial, and caudal, respectively. By way of example, if the instrument is aligned to far left of the target, the outer 524 or middle 526 ring in the left quadrant 530 will be saturated depending upon how misaligned the instrument is (i.e. whether it falls into the yellow or red range). Similarly, if the instrument 12, 80 is aligned to far cranially, the outer 524 or middle 526 ring in the upper quadrant 534 will be saturated depending upon how misaligned the instrument is. If the instrument 12, 80 has matched one of the targeted angles but not the other, only the quadrant corresponding to the misaligned angle will be saturated. The instrument window embodied in FIG. 68, employs a color coded display approximating the look of a bubble level. A free floating ring 538 moves relative to the movement of the instrument. The closer the bubble is to the center, the closer the instrument is to matching the target angle (or C-arm angle). When the instrument is within the range indicating proper alignment the ring 538 may be saturated green.

In general, to orient and maintain the surgical instrument 12, 80 along a desired trajectory during pilot hole formation, the distal end of surgical instrument 12, 80 may first be placed on the pedicle target site in the zero-angle position. The universal clip 26 or orientation shaft 86 should be set in the desired reference position, preferably perpendicular to the longitudinal axis of the spine. The surgical instrument 12, 80 may then be angulated in the sagittal plane until the desired cranial-caudal angle is reached. Maintaining the proper cranial-caudal angle, the surgical instrument 12, 80 may then be angulated in the transverse plane until the proper medial-lateral angle is attained. Once the feedback device 16 shows that both angles are correct, the instrument 12, 80 may be advanced into the pedicle to form the pilot hole. The instrument 12, 80 may be rotated back and forth to assist in the formation of the pilot hole. To keep the proper trajectory throughout formation, the instrument 12, 80 may occasionally be realigned so that the universal clip 26 or orientation shaft 86 is again perpendicular to the long axis of the spine and the angle measurements rechecked. This may be repeated until the pilot hole is complete.

To form a pilot hole in a vertebral pedicle with the aid of the surgical trajectory system 10, the surgical instrument 12, 80 is advanced to the pedicle target site where the pilot hole is to be formed. This may be done through any of open, mini-open, or percutaneous access. The precise starting point for pilot hole formation may be chosen by the practitioner based upon their individual skill, preferences, and experience. One method which may be employed to select the starting point is described further below, in conjunction with methods for utilizing the tilt sensor 14 to orient a fluoroscope. In brief, a C-arm (used for fluoroscopic imaging) may be equipped with the tilt sensor 14. The C-arm may then be oriented so that the fluoroscope's x-ray beam is parallel to the axis of the pedicle in one or both axes. A pedicle cross-section may be seen in the resulting images and a starting point may be selected.

Figure 19:
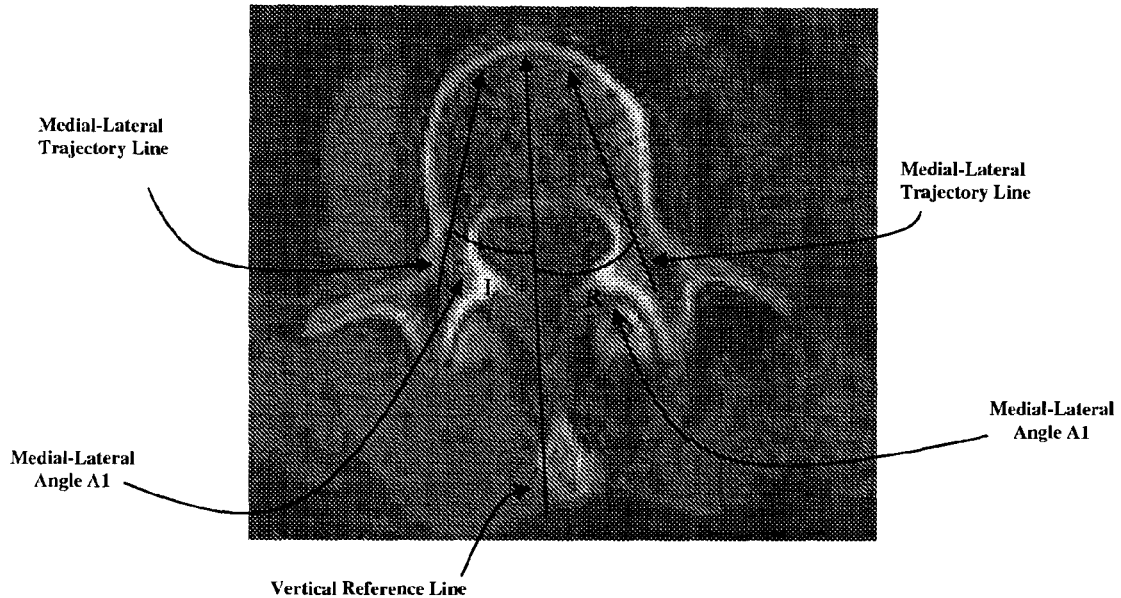
FIG. 19 illustrates a superior view preoperative MRI image used to determine the proper medial-lateral angle for hole formation, according to one embodiment of the present invention.
Figure 20:
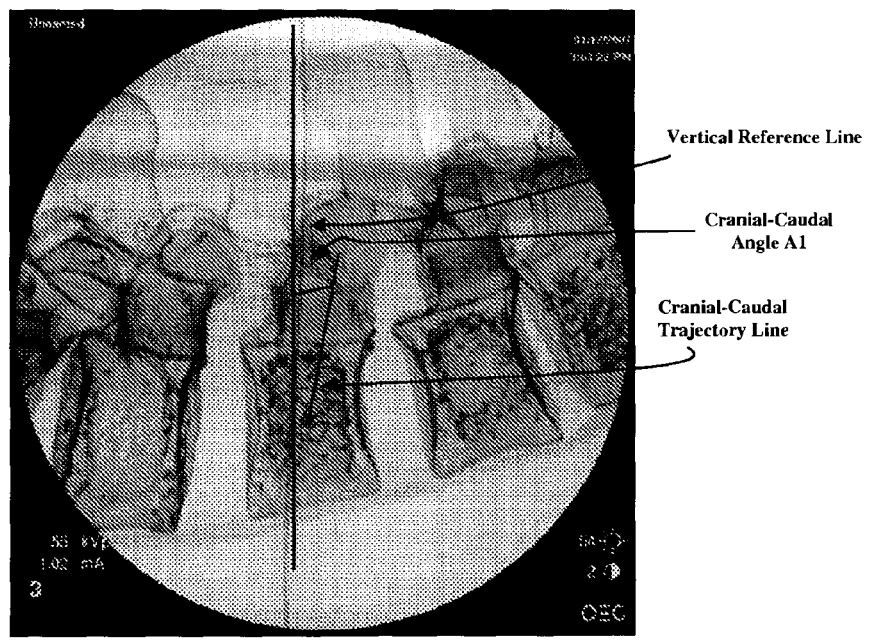
FIG. 20 illustrates an intraoperative lateral fluoroscopy image used to determine the proper cranial-caudal angle for hole formation, according to one embodiment of the present invention.

Upon safely reaching the pedicle target site, the surgical instrument 12, 80 is manipulated into the desired angular trajectory. FIGS. 19-20 illustrate one exemplary method for determining the desired trajectory angles, wherein a series of measurements are used to determine the pedicle axis of the pedicle (or more likely, pedicles) which will receive a pedicle screw. As shown in FIG. 19, preoperative superior view MRI or CAT scan images are obtained and used to determine the medial-lateral angle A1. A vertical reference line is drawn through the center of the vertebral body (in the A-P plane). A medial-lateral trajectory line is then drawn from a central position in the pedicle (e.g. a position within the soft cancellous bone, as opposed to the harder cortical bone forming the outer perimeter of the pedicle) to an anterior point of the vertebral body for the target pedicle. The resulting angle between the medial-lateral trajectory line and the reference line is measured and the result correlates to the medial-lateral angle A1 of the pedicle axis of the target pedicle, and thus also the medial-lateral angle to be used in forming the pilot hole. The measurement is repeated for each pedicle and the results may be noted and brought to the operating room for reference during the surgery. As previously mentioned, in some embodiments the feedback device 16 includes and/or is communicatively linked to a processor having memory such that the predetermined measurements may be input into the system prior to surgery for easy retrieval and application later.

As shown in FIG. 20, the cranial-caudal angle A2 may be determined using an intraoperative lateral fluoroscopy image. A vertical reference line is preferably captured in the lateral fluoroscopy image to ensure measurements are performed with respect to the direction of gravity. Fluoroscopy image outputs can generally be rotated 360° such that the image can appear on the monitor in any orientation and a vertical reference line prevents measurements from inadvertently being calculated from an incorrect reference position. One method for generating an accurate vertical reference line includes inserting a straight K-wire or needle into the spinous process at the desired vertebral level. The K-wire or needle may be oriented parallel to the acting direction of gravity, using the tilt sensor 14 and/or a bubble needle 140. of the type shown, by way of example, in FIGS. 21-22

Figure 21:
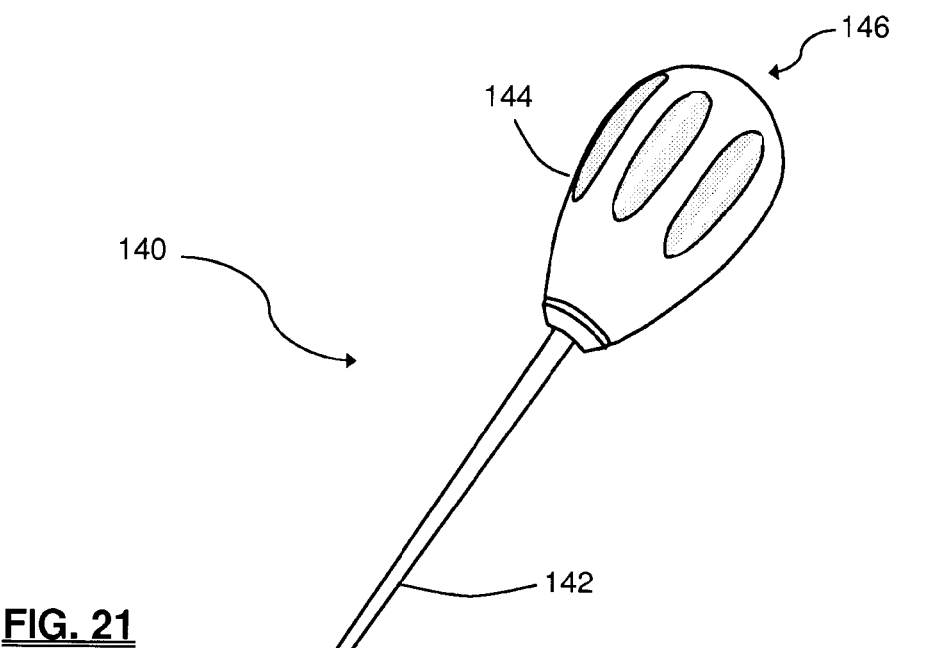
FIG. 21 is a perspective view of a bubble needle for ensuring a true vertical reference line in fluoroscopy images, according to one embodiment of the present invention.
Figure 22:
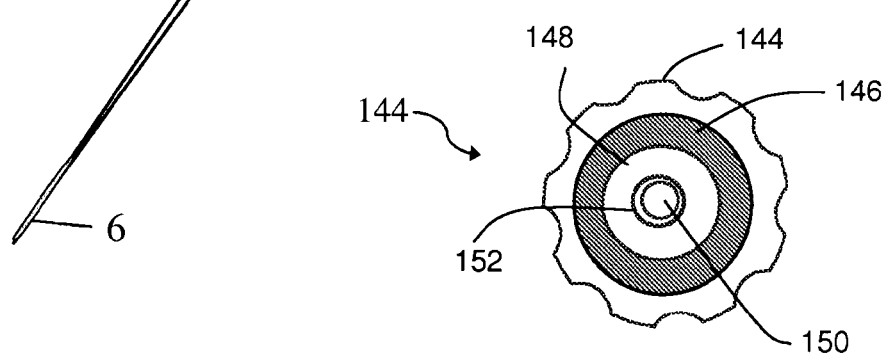
FIG. 22 is a top view of a handle portion of the bubble needle of FIG. 21 illustrating the level device used to orient the needle vertically.

The bubble needle 140 demonstrated in FIGS. 21-22 comprises a needle or probe portion 142 and a handle 144. The needle portion 142 is composes of a biocompatible radio-dense material such that it will show up in fluoroscopic images. The handle 144 may be removably or permanently attached to the needle portion 142. Like the handle of bubble level device 110, the handle of bubble needle 140 is outfitted with a level 146 mounted in it. The level 146 comprises a volume of fluid (e.g. water, oil, saline, etc. . . . ) contained within at least partially translucent enclosure 148 with a gas bubble 150 (e.g. oxygen, air, $CO_2$, etc. . . . ) disposed within the domed closure 148. The bubble 150, when the instrument is positioned vertically, will move to the approximate center of the domed enclosure 148. In this fashion, the bubble needle 140 may be employed to generate a true vertical reference line during imaging by first positioning the needle portion 142 on a desired target site within the site to be imaged, such as, for example only, docked on the spinous process and then using the level 146 to align the needle 142 vertically by holding the handle 144 with the bubble 150 at the center of the domed enclosure 148. In one optional embodiment, the domed enclosure 148 may include one or more concentric circles 152 forming a "bulls-eye" on the domed enclosure 148 to aid in the positioning of the gas bubble 150 within the domed enclosure 148. Although described herein as a "gas bubble" it will be appreciated that this "targeting" substance may be another liquid having a lighter molecular weight than the base fluid.

As an alternative, the vertical reference line may be generated by positioning a radio dense marker on the C-arm rather than the patient. Exemplary embodiments of such radio dense markers and methods for positioning them on the C-arm are described below in more detail. The lateral fluoroscopy image of FIG. 20 is shown with the vertical reference line visible in the center of the image. A cranial-caudal trajectory line is drawn from the pedicle nucleus to an anterior point of the vertebral body for the target pedicle. The resulting angle calculated between the cranial-caudal trajectory line and the vertical reference line is the cranial-caudal angle A2 of the pedicle axis and is the angle measurement to be used in forming the pilot hole. These steps should be repeated for each pedicle that is to receive a pedicle screw. It will be appreciated that while the cranial-caudal angle A2 is generally described herein as being determine intraoperatively, it is also contemplated that angle A2 may be determined preoperatively as well by combining various medical imaging and computer processing techniques to recreate the vertebra of interest and allowing the pedicle axis. to be calculated prior to surgery.

Figure 23:
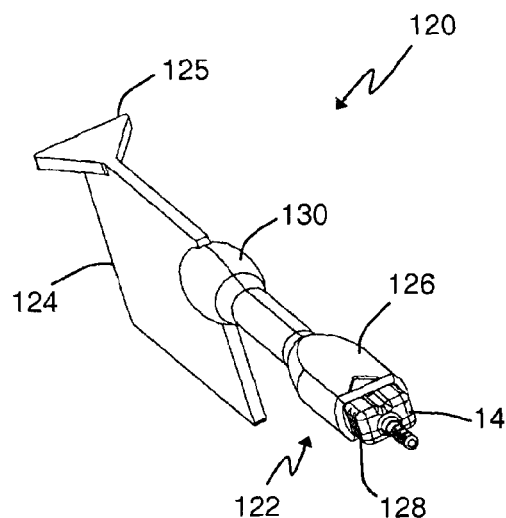
FIG. 23 is a perspective view of a digital protractor device configured for use with the surgical trajectory system of FIG. 1 to determine angle measurements, according to one embodiment of the present invention.
Figure 24A:
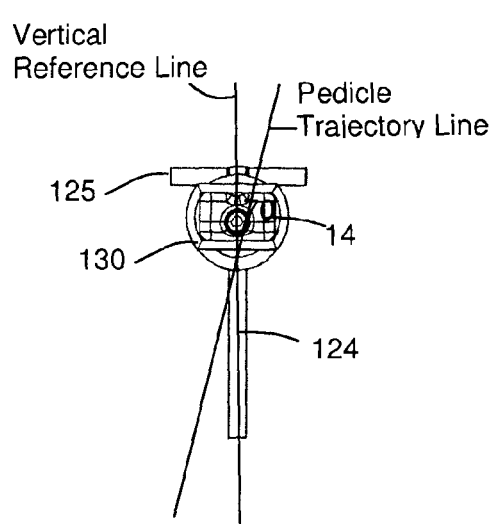
FIG. 24A is a back view illustrating the protractor device of FIG. 23 in a first position aligned with a vertical reference line in the intraoperative lateral fluoroscopy image of FIG. 20, according to one embodiment of the present invention.
Figure 24B:
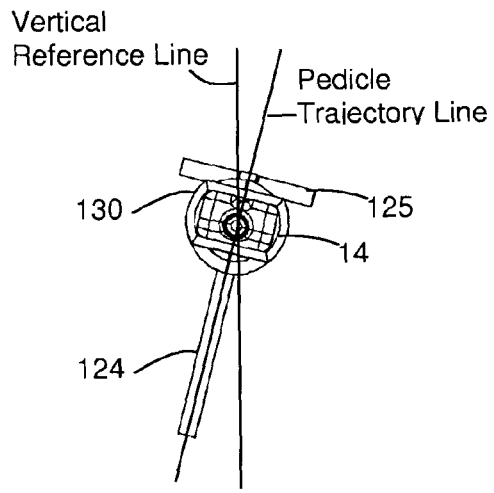
FIG. 24B is a back view illustrating the protractor device of FIG. 23 in a second position aligned with the desired pedicle trajectory on the intraoperative lateral fluoroscopy image of FIG. 20, according to one embodiment of the present invention.

According to one embodiment, shown in FIGS. 23-24, a protractor 120 may be provided with system 10 to assist in determining the cranial-caudal angle from the intraoperative image. The protractor 120 includes a handle 122 and a blade 124. A proximal end 126 of handle 122 comprises a sensor bed 128. Sensor bed 128 is similar to sensor bed 28 described above with reference to universal clip 26, and preferably engages tilt sensor 14 in the same manner. In other embodiments (not shown) the tilt sensor 14 may be permanently attached to or integrated within the handle 122 Blade 124 is generally flat and rectangular in shape with generally flat and triangular buttress element 125 extending generally perpendicularly from the top and distal region of the blade 124. The distal edge of the blade 124 is coplanar with the distal edge of the buttress element 125 such that each may be disposed against a flat surface (e.g. fluoroscope monitor) at the same time. The blade 124 attaches at its proximal end to a distal end 130 of handle 122. After taking the intraoperative lateral fluoroscopy image, the protractor 120 is used at the C-arm screen to measure the desired cranial-caudal angle. The blade 124 is lined up with the vertical reference line (FIG. 24A). Because the fluoroscopy image may not be aligned properly on the fluoroscope imaging monitor, the tilt sensor 14 may be set to zero when it is lined up with the vertical reference line. A button (not shown) may be provided on one of the tilt sensor 14 and feedback device 16 to selectively zero out of the sensor 14. The protractor 120 is then rotated about its longitudinal axis until the blade 124 lines up with the pedicle trajectory line (FIG. 24B). Feedback device 16 will display the numerical readout 99 for the angle between the vertical reference line and the pedicle trajectory line (i.e. the cranial-caudal angle) as measured by the tilt sensor 14.

Figure 25:
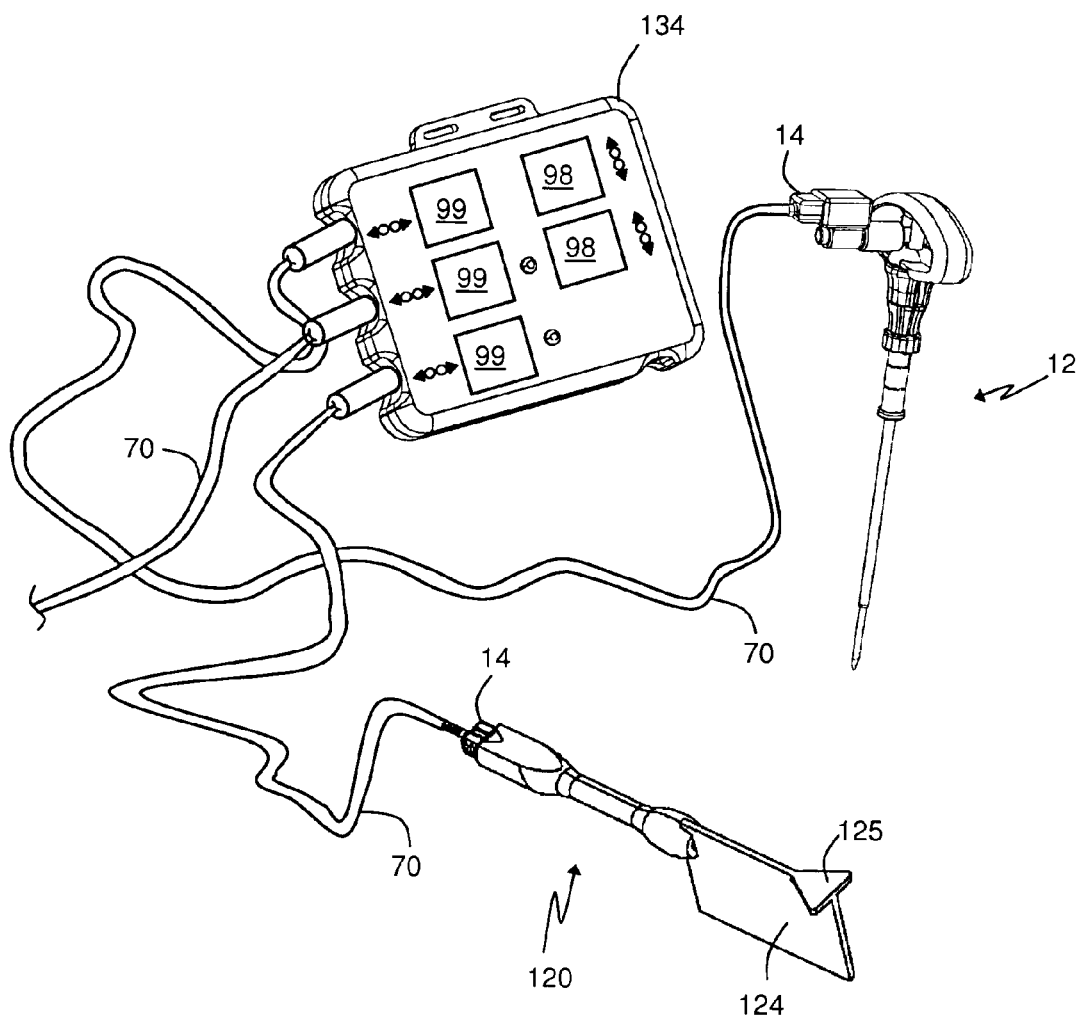
FIG. 25 is a display unit for providing feedback from multiple tilt sensors, according to one embodiment of the present invention.

With reference to FIG. 25, there is shown an alternate embodiment of a feedback device 134 which is configured to communicatively link multiple tilt sensors 14 at once. Feedback device 134 may be linked to three tilt sensors 14 individually or simultaneously and angle measurements may be provided individually or simultaneously for all attached tilt sensors 14. In one example, this allows a tilt sensor 14 to be engaged with an instrument such as pedicle access probe 12, the protractor 120, and (not shown) a C-arm without the need for multiple displays and/or connecting and disconnecting the tilt sensor 14 to the various devices during the procedure.

Once the desired trajectory angles are determined for the necessary pedicles, pilot holes may be formed and screws inserted using the tilt sensor 14 to ensure the instruments and implants are aligned with the determined angles. As mentioned above, the safety and reproducibility of pilot hole formation may be further enhanced by employing neurophysiologic monitoring, as will be described in detail below, in conjunction with the trajectory monitoring performed by the surgical trajectory system 10.

The surgical trajectory system 10 of the present invention may provide additional advantages during surgery when used to enhance intraoperative imaging commonly performed during many surgical procedures. C-arm fluoroscopes are used extensively during many surgical procedures. During spinal surgery for example, the C-arm is used frequently to help locate specific structures of the spine, to direct the positioning of surgical instruments and/or instrumentation, and to verify the proper alignment and height of vertebra, among other uses. As will be clear from the description herein, augmenting C-arm usage with the surgical trajectory system 10 may increase efficiency and reduce radiation exposure associate with using the C-arm by eliminating much of the guess work and trial and error that is often required to achieve the desired fluoroscopic image.

Figure 26:
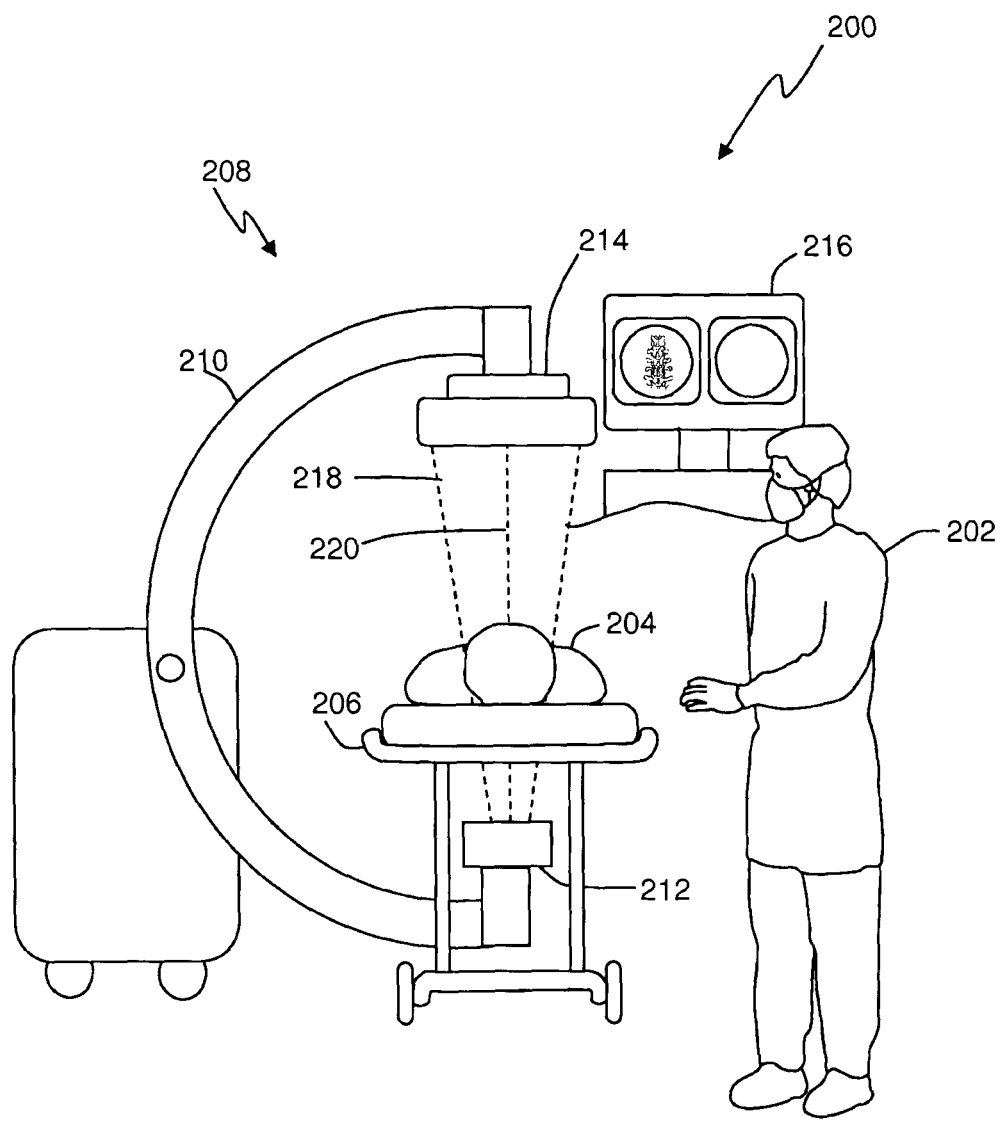
FIG. 26 is an illustration of an operating theater equipped with a surgical table, C-arm fluoroscope, fluoroscope monitor, practitioner, and patient.

With reference to FIG. 26, there is shown a typical operating theatre 200 in which a practitioner 202 may perform surgical procedures on a patient 204. The patient 204 is positioned on a radio-opaque operating table 206. Arrayed around the table 206 are a standard C-arm 208, comprising a frame 210, a signal transmitter 212, and a signal receiver/image intensifier 214, and a flour-monitor 216. In use, an x-ray beam 218, having a central axis 220, may be directed from the signal transmitter 212 through a desired area of patient 204 and picked up by the signal receiver 214. An image of the patient's 204 body tissue located in the path of beam 218 is generated and displayed on fluoroscope imaging monitor 216. It should be appreciated that while the C-arm 208 is discussed herein generally for use during spine surgery to capture images of the spine, such discussion is for exemplary purposes only. It will be understood that the C-arm 208 may be utilized for imaging in a wide variety of surgical procedures. The devices and methods for orienting the C-arm described herein may apply equally well to those other such procedures, and as such, fall within the scope of the present invention.

Figure 27:
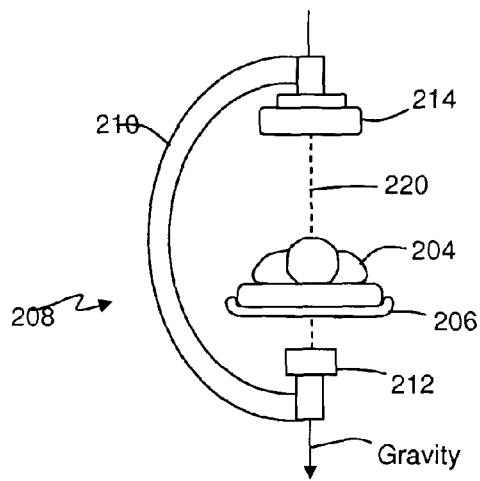
FIG. 27 is a front view of the C-arm of FIG. 26 oriented in an A/P position for generating an A/P fluoroscopic image.
Figure 28:
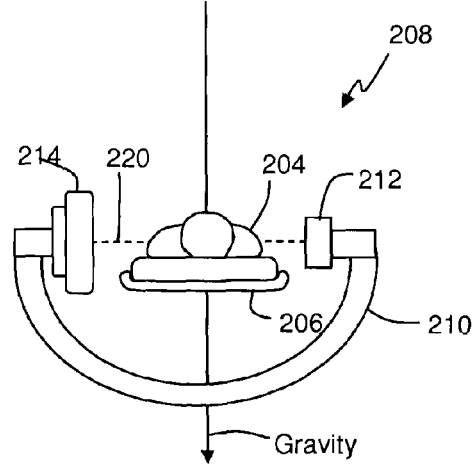
FIG. 28 is front view of the C-arm of FIG. 26 oriented in a lateral position for generating a lateral fluoroscopic image.
Figure 29A:
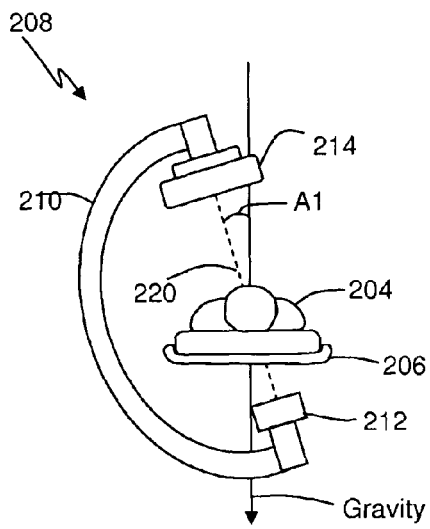
FIGS. 29A-29B are front views of the C-arm of FIG. 26 oriented according to desired medial-lateral angles between the A/P position of FIG. 27 and the lateral position of FIG. 28.
Figure 29B:
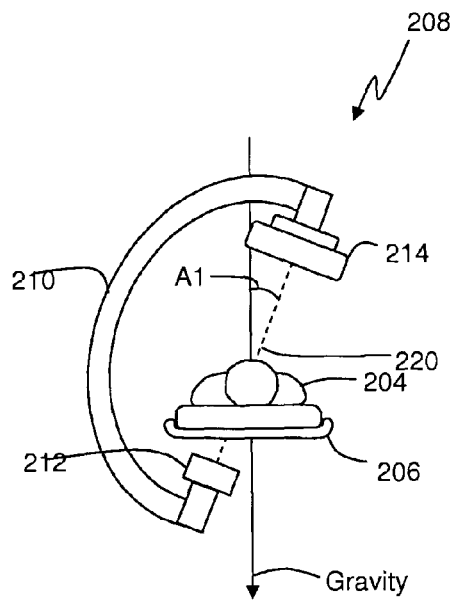
Figure 30A:
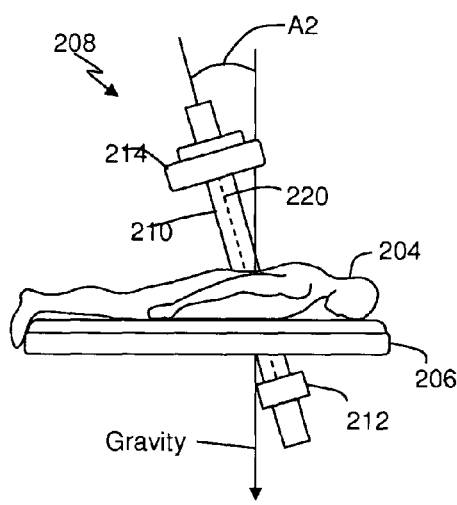
FIGS. 30A-30B are side views of the C-arm of FIG. 26 oriented according to various cranial-caudal angles.
Figure 30B:
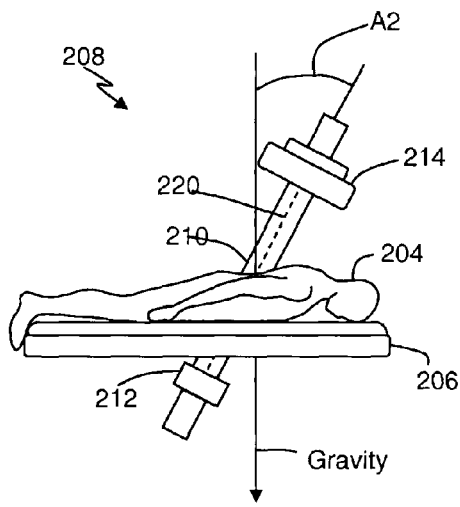
Figure 31:
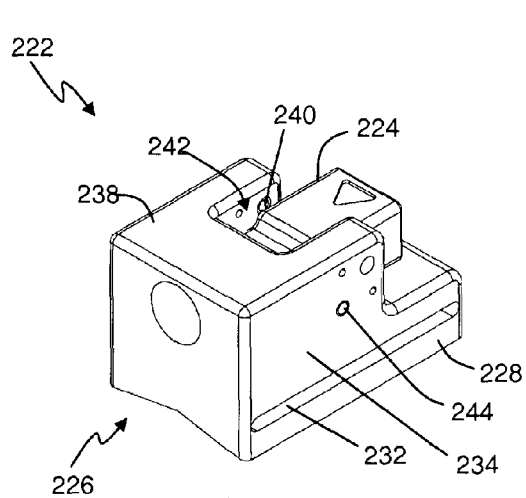
FIG. 31 is a perspective view of a coupler for coupling the surgical trajectory system of FIG. 1 to the C-arm of FIG. 26, according to one embodiment of the present invention.
Figure 32:
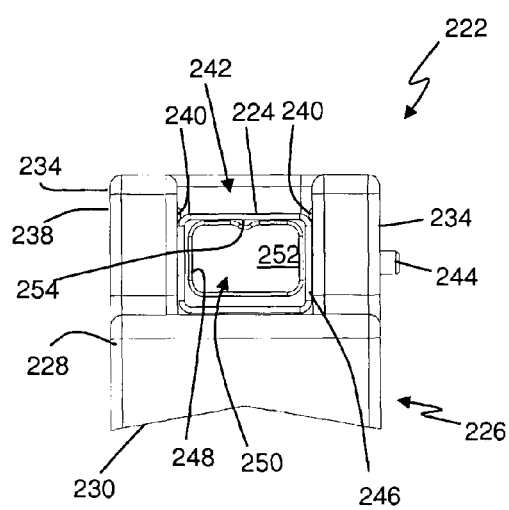
FIG. 32 is a front view of the coupler of FIG. 31, according to one embodiment of the present invention.

As illustrated in FIGS. 27-30, the C-arm frame 210 may be adjusted to alter the path of the beam 218, and thus the image that is generated. In FIG. 27 the frame 210 is oriented such that beam 220 travels parallel to the direction of gravity. With the patient in the prone position, as shown herein, this position of frame 210 generates an anterior-posterior (A/P) image. This position of C-arm 208 is referred to hereafter as the A/P position. Rotating the frame 90° in a medial-lateral direction (through a transverse plane), as depicted in FIG. 28, directs the beam 220 perpendicular to the direction of gravity and generates a lateral image. This position of the C-arm 208 is referred to as the lateral position. A/P and lateral images may both be useful during a spinal procedure and the C-arm may be adjusted between the A/P and lateral positions numerous times during the procedure. As illustrated in FIGS. 29A-29B, the frame 210 may also be oriented in any position within the transverse plane between the A/P and lateral positions, such that the beam 220 forms an angle $A1(c)$ (the medial-lateral angle) between zero and 90° with respect the direction of gravity. Furthermore, as illustrated in FIGS. 30A-30B, the frame 210 may also be rotated in a cranial-caudal direction (within a sagittal plane) such that the beam 220 forms another angle $A2(c)$ (the cranial-caudal angle) with respect to the direction of gravity. By way of example only, the C-arm may be oriented such that one or both of angles $A1(c)$ and $A2(c)$ correspond to the desired axis of trajectory of a pedicle bone, i.e. angles A1 and A2, as will be discussed in more detail below.

By attaching the tilt sensor 14 to the C-arm 208 in a known positional relationship, the angular orientation of the C-arm with respect to the reference axis (gravity) may be determined. This enables the practitioner to quickly position the C-arm 208 in a known orientation, such as, by way of example only, the precise orientation in which a previous image was acquired. Doing so may eliminate the time and extra radiation exposure which is often endured while acquiring numerous images while "hunting" for the right image. Attaching the tilt sensor 14 to the C-arm may further enable the practitioner to determine the angular orientation of anatomical structures within the patient (e.g. vertebral pedicles), as will be described below. This may be advantageous, for example only, when the practitioner is performing pedicle fixation and preoperative images (such as the MRI or CAT images which may be used to determine the pedicle axis angle A1) are not available for preoperative planning, as described above.

FIGS. 31-34 depict a coupler 222 for attaching the tilt sensor 14 to a standard C-arm 208 according to one embodiment of the invention. Coupler 222 comprises a sensor bed 224 configured to receive tilt sensor 14, and a mount 226 configured to attach to the C-arm 208. Mount 226 includes a base region 228 equipped with a slot 232 spanning the distance between the sides 234. In use, a strap or belt 236 (FIG. 36) may be passed through slot 232 and fastened around C-arm 208 to secure the coupler 222, and thus the tilt sensor 14, to the C-arm 208. An upper region 238 of coupler 222 contains a cutout 242 in which sensor bed 224 is pivotally attached to coupler 222 via a pin 244. Sensor bed 224 may preferably pivot between a horizontal position (with respect to base region 228), illustrated in FIG. 33, and a vertical position (with respect to base region 228), illustrated in FIG. 34. As will be described below, pivoting the sensor bed 224 between the vertical position and the horizontal position allows the tilt sensor 14 to be aligned in the same starting orientation (with respect the direction of gravity) whether the C-arm is in the A/P position or the lateral position. Ball-springs 240, or any of a number of other suitable mechanisms, may be positioned within cutout 242 to prevent unintentional movement of sensor bed 224 and maintain it in either of the desired horizontal or vertical positions.

Sensor bed 224 is similar to sensor bed 28 of the universal clip 26 as both are designed to receive and secure tilt sensor 14. Bed 224 has an exterior surface 246, an interior surface 248, and an opening 250. Together, interior surface 248 and opening 250 form cavity 252. Sensor bed 224 is generally rectangular in shape, however, it should be understood that sensor bed 224 may be provided in any suitable shape having any suitable cross-section (e.g. generally ellipsoidal, triangular, or other polygonal shape) without deviating from the scope of the invention. Cavity 252 is dimensioned to snugly receive at least a portion of tilt sensor 14. An alignment ridge 254, configured to engage tilt sensor 14 as described below, may be provided along the interior surface 248 (shown by way of example only along the top of sensor 14) to ensure tilt sensor 14 is positioned properly (e.g. right side up) within the cavity 252. Additional engagement features, such as for example, a hole or indentation (not shown) may be provided to cooperate with protrusion 24 on tab 22 help secure the tilt sensor 14 within cavity 252.

Figures 33, 34:
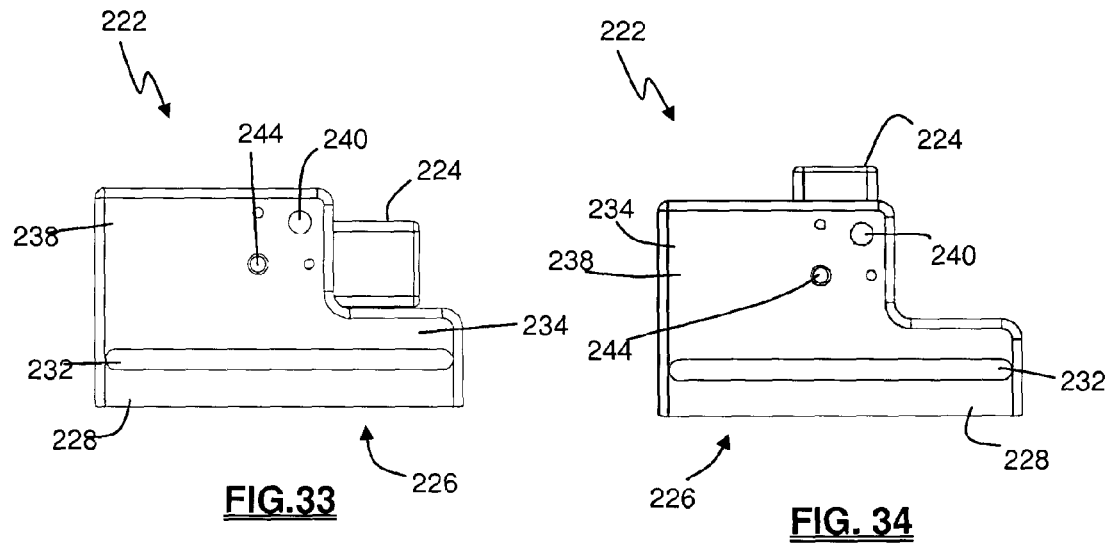
FIG. 33 is a side view of the coupler of FIG. 31 with a sensor bed aligned in a horizontal position, according to one embodiment of the present invention.
FIG. 34 is a side view of the coupler of FIG. 31 with a sensor bed aligned in a vertical position, according to one embodiment of the present invention.
Figure 35:
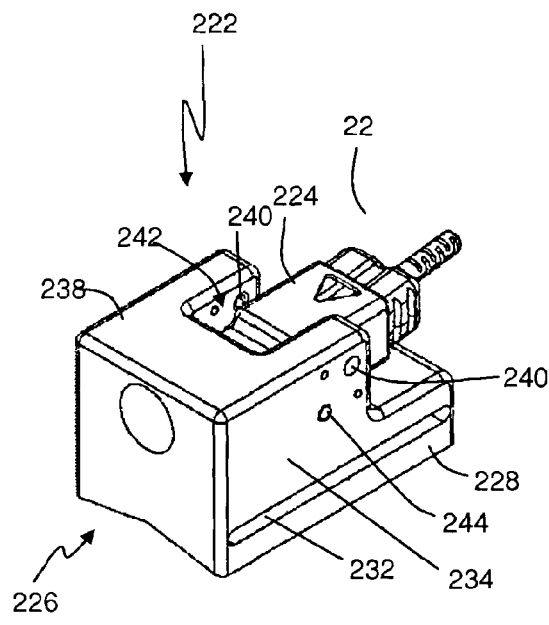
FIG. 35 is a perspective view of the coupler of FIG. 31 with the tilt sensor of FIG. 2 engaged in the sensor bed, according to one embodiment of the present invention.

To attach tilt sensor 14 to the coupler 222, the practitioner 202 or other user may grasp tilt sensor 14 and align the groove 20 of housing 18 with the alignment ridge 254 of cavity 252. The tilt sensor 14 may then be slid into the cavity until the protrusion 24 engages the hole or indentation in cavity 252. In other embodiments (not shown) the tilt sensor 14 may be permanently attached to or integrated within coupler 222. FIG. 35 illustrates the tilt sensor 14 fully engaged within the sensor bed 224 of the coupler 222 and in the horizontal position referenced with regard to FIG. 33. Thereafter, sensor bed 224 and tilt sensor 14 may be pivoted into one or the other of the horizontal and vertical positions as needed during the procedure. FIG. 36 shows the coupler 222 attached to the C-arm 208 oriented in the A/P position, while FIG. 37 shows the coupler 222 attached to the C-arm 208 oriented in the lateral position. In either case, the belt 236 is fastened around signal receiver 214 and the base region 228 of coupler 222 rests square and secure against a sidewall 256 of receiver 214. The bottom surface 230 of mount 226 may be contoured or shaped to match the contour of the side wall 256. For example, the bottom surface 230 may have a generally upside down "V" shape (best viewed in FIG. 32) to securely rest against the rounded surface of side wall 256. To orient the tilt sensor 14 in the zero-angle position with the C-arm 208 oriented in the A/P position of FIG. 36, the sensor bed 224 is positioned in the "vertical" position relative to the coupler 222 as shown in FIG. 34. To orient the tilt sensor 14 in the zero-angle position with the C-arm 208 in the lateral position of FIG. 37, the sensor bed 224 is arranged in the "horizontal" position relative to the coupler 222 as shown in FIGS. 33 and 35. In either case, this positions the tilt sensor 14 perpendicular to gravity.

Figure 38:
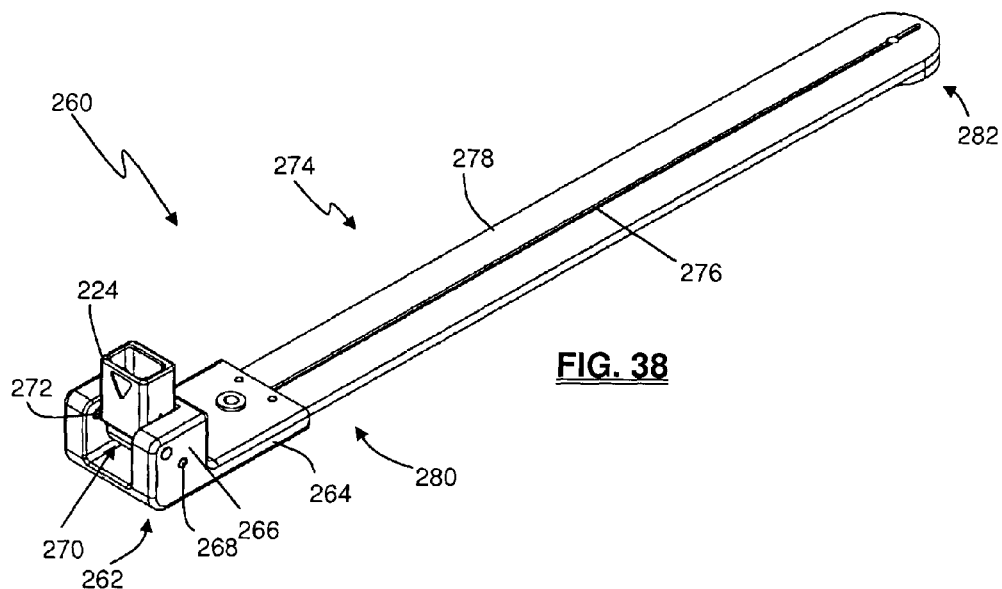
FIG. 38 is a perspective view of a coupler for coupling the surgical trajectory system of FIG. 1 to the C-arm of FIG. 26, according to another embodiment of the present invention.
Figure 39:
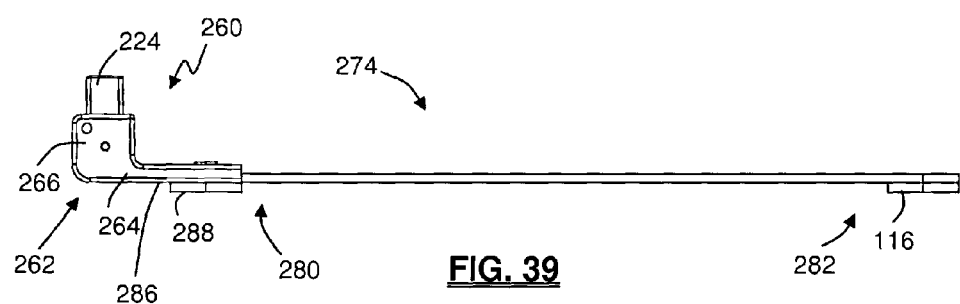
FIG. 39 is a side view of the coupler of FIG. 38, according to one embodiment of the present invention.
Figure 40:
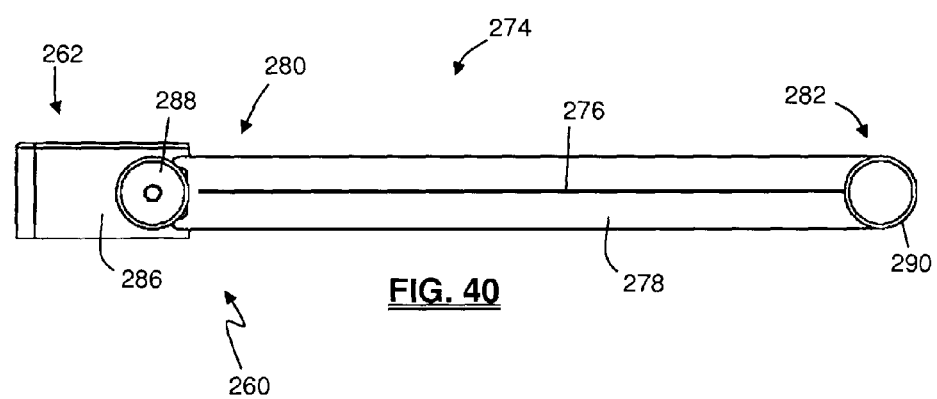
FIG. 40 is bottom view of the coupler of FIG. 38, according to one embodiment of the present invention.

FIGS. 38-40 depict a coupler 260 for attaching tilt sensor 14 to a standard C-arm 208 according to another example embodiment of the preset invention. Coupler 260 includes sensor bed 224 and a mount 262 having a base region 264 for attaching to the C-arm 208 and an upper region 266 for pivotally attaching sensor bed 224 to the mount 262. In other embodiments (not shown) the tilt sensor 14 may be permanently attached to or integrated within coupler 260. Sensor bed 224 is pivotally attached, via a pin 268, within a cutout 270 in upper region 266. Sensor bed 224 may preferably pivot between a horizontal position (with respect to base region 264) and a vertical position (with respect to base region 264) as described above with reference to coupler 222 in FIGS. 33-35. Ball-springs 272, or any other suitable mechanism, may be positioned within cutout 270 to prevent unintentional movement of sensor bed 224 and maintain it in either of the desired horizontal and vertical positions.

Figure 41:
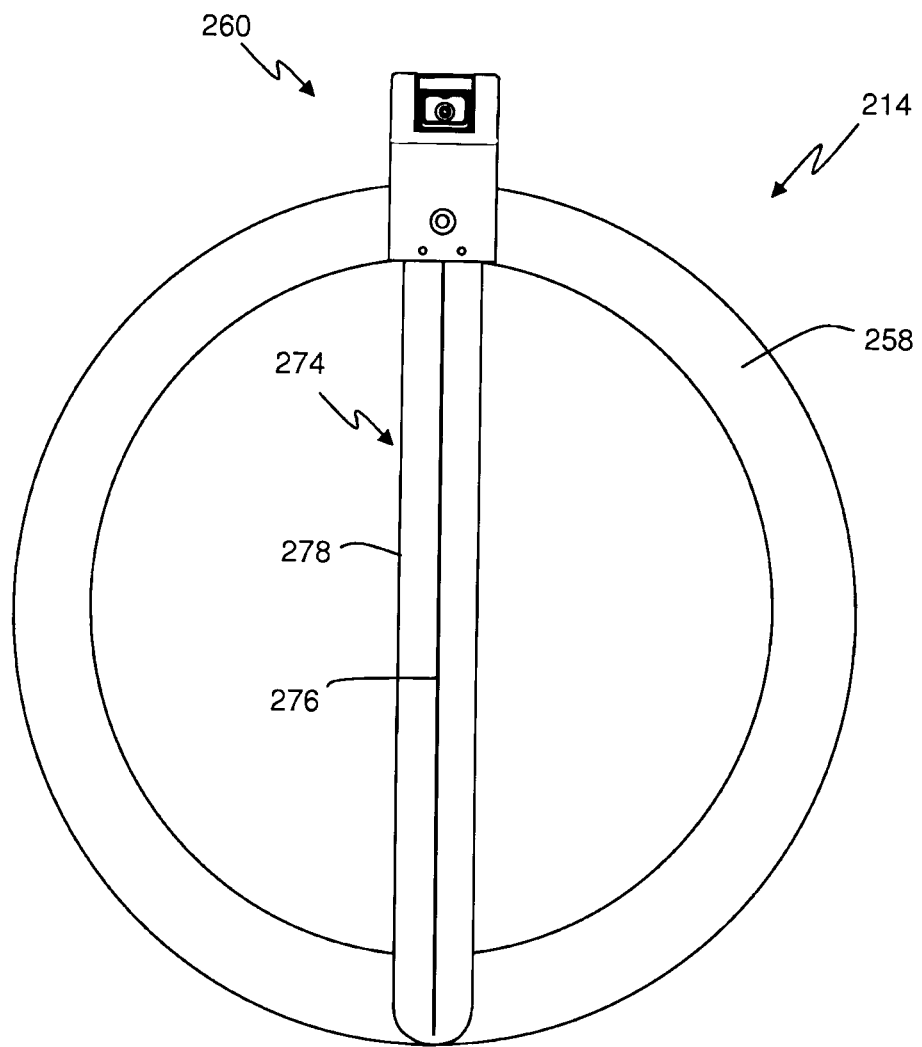
FIG. 41 is a front view of the coupler of FIG. 38 and tilt sensor of FIG. 1 attached to the signal receiver face of the C-arm of FIG. 26, according to one embodiment of the present invention.
Figure 42:
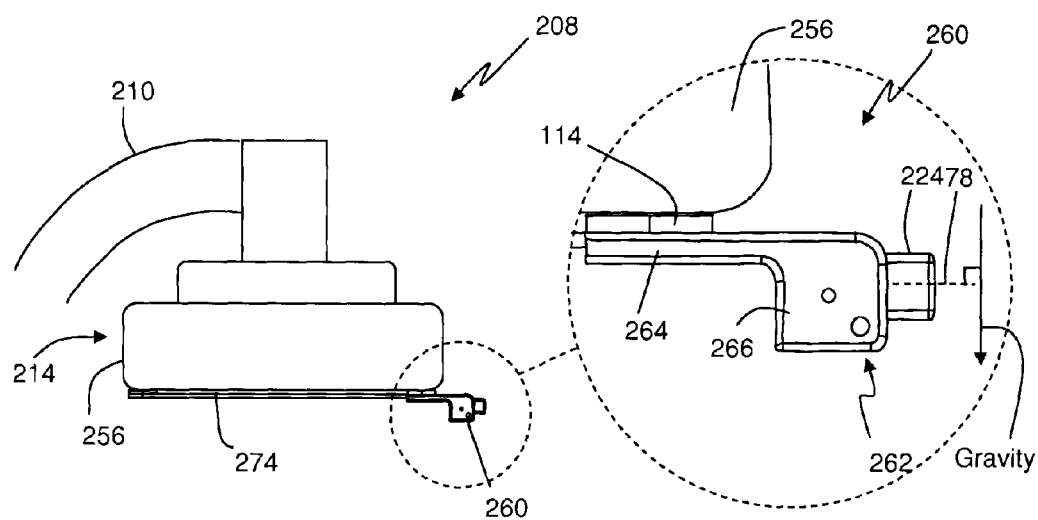
FIG. 42 is a side view of the coupler/tilt sensor combination of FIG. 41 attached to a signal receiver of the C-arm of FIG. 26 in the A/P position, according to one embodiment of the present invention.
Figure 43:
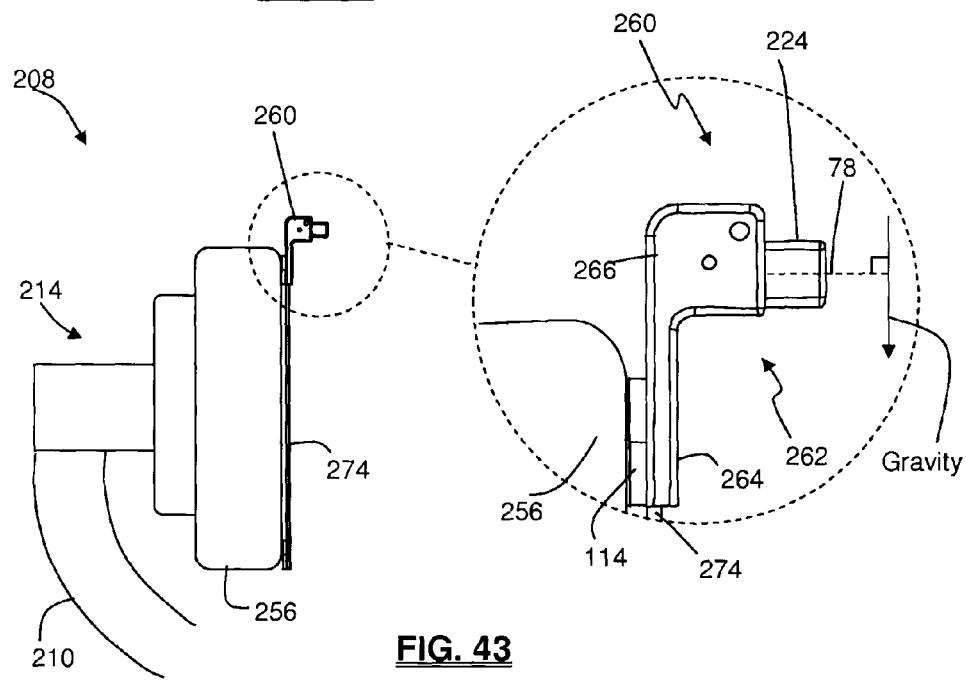
FIG. 43 is a side view of the coupler/tilt sensor combination of FIG. 41 attached to a signal receiver of the C-arm of FIG. 26 in the lateral position, according to one embodiment of the present invention.

Whereas mount 226 of coupler 222 was configured to preferably attach to the sidewall 256 of signal receiver 214, mount 262 is configured to preferably mount to the face 258 of signal receiver 214, as illustrated in FIGS. 41-43. In one embodiment, Velcro® may be used to releasably fix mount 262 to face 258. Other attachment means, including, but not necessarily limited to, adhesive gel and adhesive tape may be used instead of Velcro®. As illustrated in FIGS. 42-43, since the orientation of coupler 260 varies from that of coupler 222 by 90° when fixed to the C-arm (because coupler 222 attaches to the sidewall 256 and coupler 260 attaches to the face 258), the roles of the horizontal and vertical positions of the sensor bed 224 are reversed. When C-arm 208 is in the A/P position as in FIG. 42, the sensor bed 224 is pivoted to the horizontal position such that the length and width of the tilt sensor 14 are perpendicular to the direction of gravity. Conversely, when C-arm 208 is in the lateral position, as in FIG. 43, the sensor bed 224 is pivoted to the vertical position such that the length and width of tilt sensor 14 are again perpendicular to gravity.

Coupler 260 may also include an integrated plumb line 274, which may generate a reference line viewable in fluoroscopic images generated by C-arm 208. Preferably, coupler 260 and plumb line 274 may be fixed to the C-arm such that the plumb line 274 forms a vertical reference line in lateral fluoroscopic images. Plumb line 274 comprises an elongated radio-dense marker 276 situated in a radio-opaque case 278. Case 278 is fixed to coupler 222 at a first end 280. A free end 282 may be attached to C-arm face 258, via Velcro® or other suitable attachment means, to help prevent any movement of the plumb line 274 once it is positioned.

Coupler 260 is preferably fixed to the C-arm face 258 with the C-arm in the lateral position, which allows gravity to help correctly position the plumb line 274. To attach coupler 260 to the signal receiver face 258 according to a preferred embodiment, a Velcro® pad may be adhered to the face 258 in a position 284 adjacent to the outer edge and centered along the vertical diameter of face 258. A complementary Velcro® pad may be adhered to button 288 pivotally coupled to the bottom surface 286 of coupler 260 and the Velcro® pads stuck together. If it is not already in place, tilt sensor 14 is positioned in sensor bed 224, which should be oriented in the vertical position (if C-arm is in the lateral position). The free end 282 of plumb line 274 may then be moved (e.g. via gravity of the user) such that plumb line 274 and coupler 260 pivot around button 288 until the tilt sensor is in the zero angle position. Once the zero-angle position is achieved, Velcro® pads may be used to attach another button 290, situated on the free end 282 of plumb line 274, to the face 258.

Figure 44:
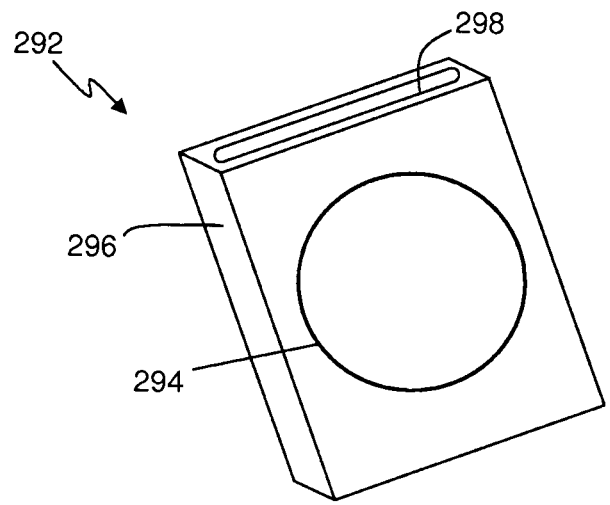
FIG. 44 is a perspective view of a target containing a radio-dense marker for augmenting a radio-dense marker included with the coupler of FIG. 38, according to one embodiment of the present invention.
Figure 45:
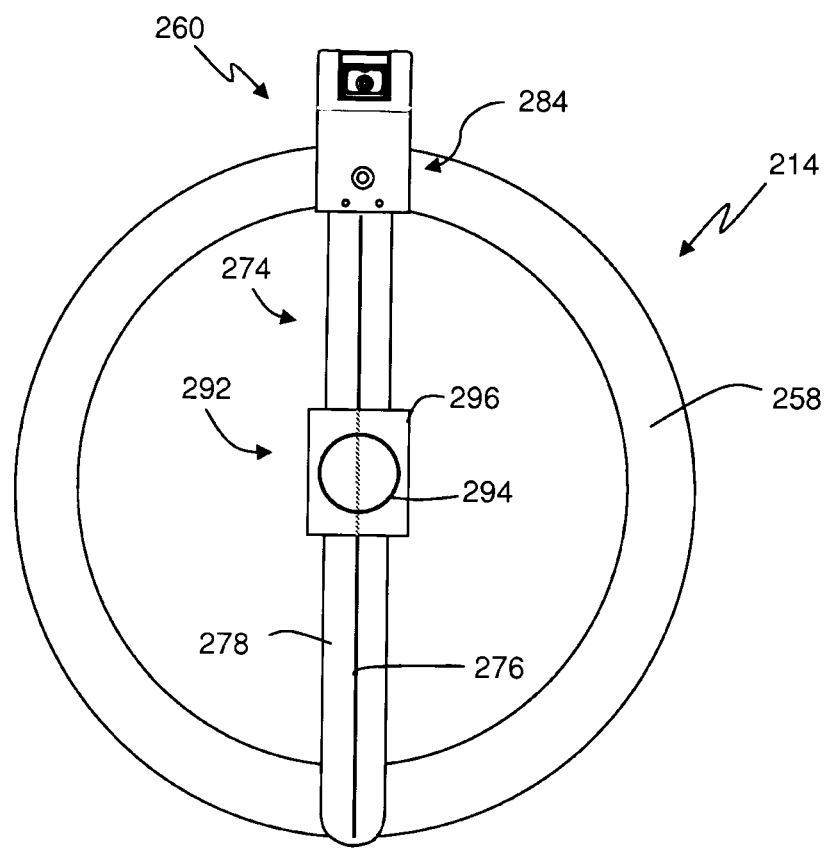
FIG. 45 is a front view of the target of FIG. 44 in use with the coupler of FIG. 38, according to one embodiment of the present invention.

In addition to the vertical reference line for which plumb line 274 may be utilized, other configurations are also contemplated. By way of example only, FIG. 44 depicts a target 292 which may be used with plumb line 274. Target 292 includes a generally circular radio-dense marker 294 situated in a radio-opaque target case 296. Target case 296 includes an aperture slot 298 configured to receive and slidably engage case 278 of plumb line 274. Once plumb line 274 is fixed in position, target 292 may be slid along plumb line 274 until a desired position along plumb line 274 is achieved, after which it may be fixed in place with Velcro® or other suitable attachment means. FIG. 45 depicts target 292 positioned along the plumb line 274 at the center of face 258. Circular radio-dense marker 294 has a diameter of approximately 1-inch. However, it will be understood that marker 294 may have any suitable size, ranging anywhere from just large enough to be seen, to just small enough to fit on face 258 of receiver 214. It should also be understood that while target marker 294 is shown and described as generally circular, target marker 294 may be provided having any general shape, including but not necessarily limited to, generally rectangular, triangular, ellipsoidal, and polygonal. In addition, plumb line 274 may also comprise various other configurations. With reference to FIG. 46, by way of one example, case 278 may be shaped and dimensioned to approximate that of receiver face 258, and radio-dense marker 276 may be provided according to any desirable layout, such as the four equal length bars positioned equidistantly around case 278 shown in FIG. 46.

While couplers 222 and 260 have been described as attaching the tilt sensor 14 in a pivotal relation, it should be appreciated that this is not always necessary. In some instances (such as when determining the cranial-caudal angle using the C-arm) the sensor output is adequate if only one axis of the sensor is perpendicular to gravity. Thus the tilt sensor 14 may be engaged to the coupler in a fixed orientation. Alternatively, the need to pivot the tilt sensor 14 may be overcome by equipping sensor package 17 with a second 2-axis accelerometer arranged perpendicular to the first. As the tilt sensor 14 is angled past the effective range of the first accelerometer the second accelerometer take over make assume the measurement function from the first accelerometer.

In an alternate embodiment of the present invention, it is contemplated that the orientation of C-arm 208 with respect to the patient 204 may be adjusted by moving the patient rather than the C-arm 208. To accomplish this, by way of example only, trajectory system 10, and specifically, tilt sensor 14 may be attached to the surgical table 206. With the C-arm 208 in the A/P position, the bed, and thus the patient on the bed, may be rotated laterally (through a transverse plane), shown in FIG. 47, to change the medial-lateral angle at which the x-ray beam 220 travels through the patient. As shown in FIG. 48, the bed may also be rotated in a cranial or caudal direction (through a sagittal plane) to change the cranial-caudal angle at which the x-ray beam 220 travels through the patient. The trajectory system 10, via feedback device 16, will display the cranial-caudal and medial-lateral angles of the bed with respect to gravity. Since the beam 220 is parallel to the direction of gravity in the A/P position, the cranial-caudal and medial-lateral angles of orientation of the x-ray beam with respect to the bed 206 (and patient 204) are also known. To later obtain images from precisely the same position, the bed may be readjusted until the feedback device 16 again shows the angular readouts corresponding to the desired position. Although not shown, it is within the scope of the invention to attach the tilt sensor 14 directly to the patient 204 rather than the bed 206. Again, with the C-arm 208 aligned in the A/P position, the bed may be rotated to change one or both of the medial-lateral angle and cranial-caudal angle of the patient's spine with respect to the x-ray beam 218. Again, later images may be obtained from precisely the same position by readjusting the bed until the feedback device 16 again shows the correct angular readouts for the position desired.

Simple and reproducible orienting of the C-arm 208 in a known position while decreasing the x-ray exposure for everyone represents one general advantage of using the trajectory system 10 to enhance imaging techniques during surgery. Other benefits may also be gained by using the system 10 with a C-arm, such as the previously mentioned benefit of determining the angular orientation or trajectory of an anatomical structure within the patient. Without limiting the scope of the present invention, specific examples will be described for determining the axis of a vertebral pedicle, or in other words, the angles A1 and A2 described above with regard to forming a pilot hole for pedicle screw implantation.

Figure 49:
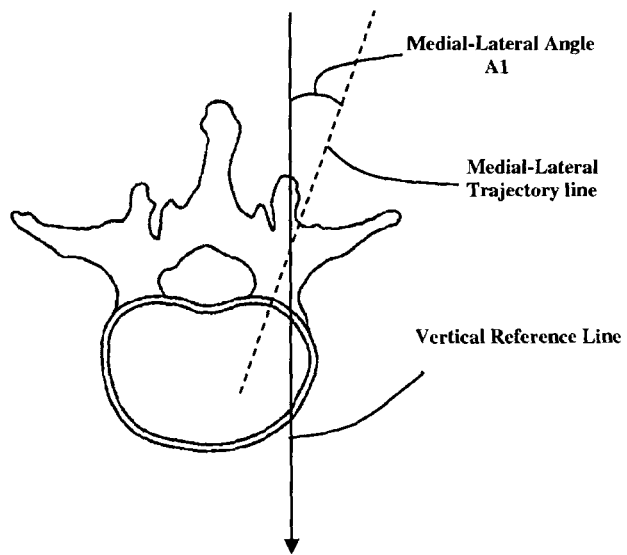
FIG. 49 is a top view of a vertebral body showing the medial-lateral angle A1 of the pedicle axis.
Figure 50:
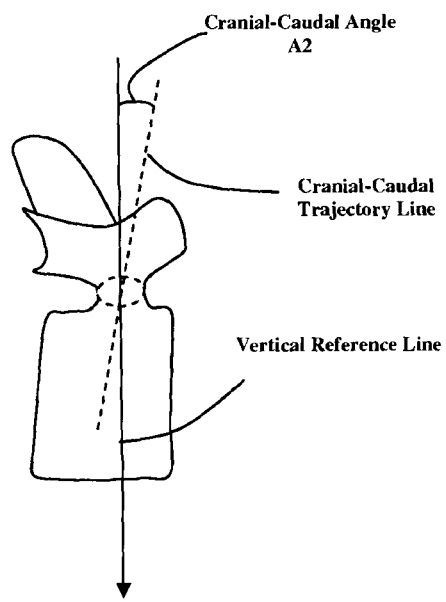
FIG. 50 is a side view of a vertebral body showing the cranial-caudal angle A2 of the pedicle axis.

In a first example, the trajectory system 10 equipped C-arm 208 may be used to help determine the axis of a pedicle as well as a good starting position for entering the pedicle in line with the determined axis. As mentioned, the implantation of pedicle screws without breaching, cracking, or otherwise compromising the pedicle wall is critical to the success of a procedure still presents a significant challenge to spinal practitioners. To mitigate this challenge according to one embodiment of the present invention, the orientation of the pedicle axis, defined by a medial-lateral angle A1 (illustrated in FIG. 49) and a cranial-caudal angle A2 (illustrated in FIG. 50), may be determined and the pedicle screw and/or related instruments may be advanced through the pedicle along the desired trajectory.

In this example the angle A1, or medial-lateral angle, of the pedicle is determined preoperatively in the same manner previously described with reference to FIG. 19. Specifically, a vertical reference line is drawn through the center of the vertebral body and a medial-lateral trajectory line is drawn from a central position in the pedicle (e.g. a position within the soft cancellous bone, as opposed to the harder cortical bone forming the outer perimeter of the pedicle) to an anterior point of the vertebral body. The angle formed between the medial-lateral trajectory line and the vertical reference line is measured and represents the angle A1 value. The angle A2, or the cranial-caudal angle, may preferably be determined intraoperatively with a C-arm fluoroscope 208 equipped with the trajectory system 10 of the present invention. Angle A2 is determined in essentially the same fashion as it was described previously. However, with the addition of the tilt sensor 14, need to measure the angle from the fluoroscopic imaging monitor is obviated. Instead, when the vertical reference line formed by plumb line 247 lines up with the pedicle, the pedicle angle A2 corresponds to the angle of the cranial-caudal trajectory angle of the C-arm tilt sensor 14, which is displayed on feedback device 16.

Figure 51:
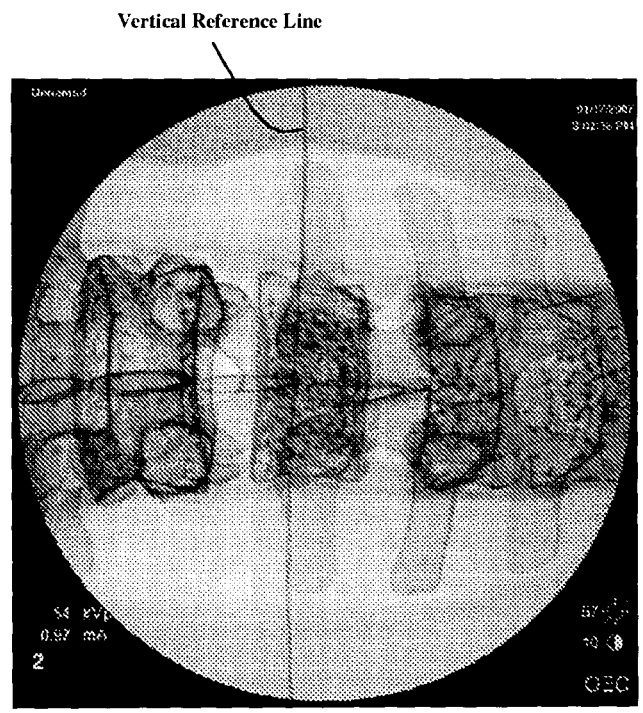
FIG. 51 is a true A/P image of the spine with a vertical reference line formed by the coupler of FIG. 38, according to one embodiment of the present invention.

To determine the cranial-caudal angle A2, the C-arm 208 is first positioned so that the base is perpendicular to the spine of the patient 204. This may be verified with an A/P fluoroscopy image as shown in FIG. 51. The base is perpendicular to the spine when the spinous process is equally spaced between the pedicles. Also, when the base of the C-arm 208 is perpendicular to the spine, the vertical reference line created by plumb line 274 is generally parallel to the vertebral endplates in the A/P fluoroscopy image.

Figure 52:
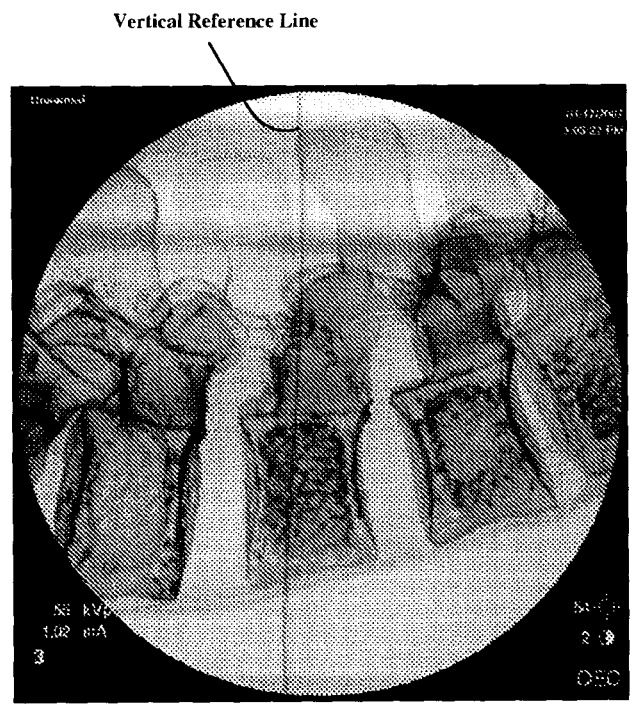
FIG. 52 is a true lateral image of the spine with a vertical reference line formed by the coupler of FIG. 38, according to one embodiment of the present invention.
Figure 53:
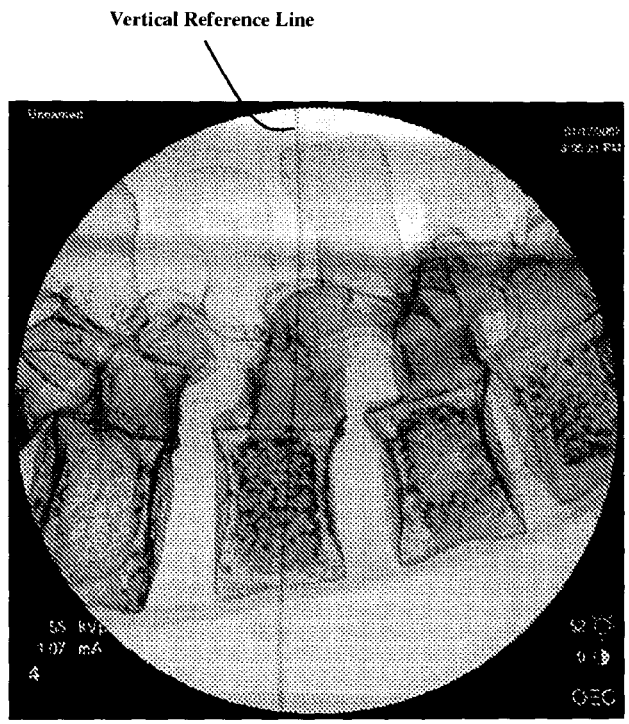
FIG. 53 is a trajectory lateral image of the spine where the C-arm has been rotated to align the vertical reference line with the pedicle axis, according to one embodiment of the present invention.

Once the alignment of the base is verified, the C-arm 208 is rotated to the lateral position and the tilt sensor 14 may be pivoted into its corresponding position (i.e. the horizontal position if the coupler is fixed to the receiver sidewall 256 or the vertical position if the coupler is fixed to the receiver face 258). Starting from the lateral position, illustrated in FIG. 52, the C-arm 208 may be rotated radially (through a sagittal plane) until the vertical reference line is parallel to the pedicle axis. In this position, which may be referred to as the trajectory lateral position illustrated in FIG. 53, A2 is equal to A2(*c*). When the practitioner is satisfied with the alignment of the vertical reference line to the pedicle axis, the correct A2 value measured from the tilt sensor 14 may be recorded from the feedback device 16. Again, this angle measurement corresponds to the cranial-caudal angle A2 of the pedicle axis and the method may be repeated for each pedicle that is to receive a pedicle screw.

Figure 54:
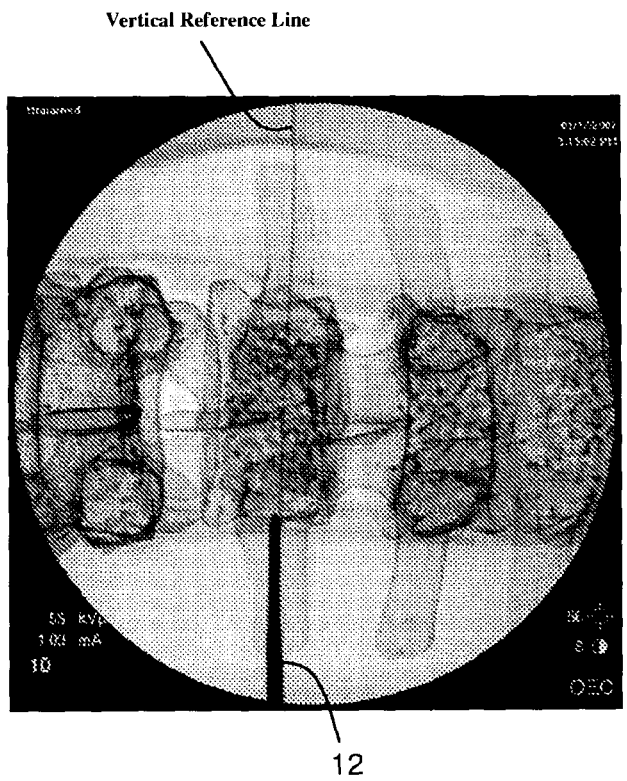
FIG. 54 is an A/P image of the spine used to determine the starting point for pilot hole formation through the pedicle, the A/P image being taken while maintaining the lateral trajectory of the C-arm as set as in FIG. 53, according to one embodiment of the present invention.

To select a starting point for pedicle penetration, the C-arm 208 may be placed in the trajectory lateral position for the pedicle of interest. This may be accomplished by again lining up the vertical reference line in a lateral fluoroscopy image with the pedicle axis or by simply rotating the C-arm until the tilt sensor 14 feedback readout 16 indicates that the previously determined trajectory lateral position has been attained (i.e. the angle measurement displayed by the tilt sensor 14 matches the angle measurement displayed when the trajectory lateral position was initially determined). From the trajectory lateral position, the C-arm 208 may be rotated back to the A/P position while maintaining the rotation imparted to achieve the trajectory lateral position. As pictured in FIG. 54, a pedicle penetration instrument, such as instrument 12 described above, may be advanced to the target site and positioned on the lateral margin of the pedicle, which is the preferred starting point according to this example. The surgical instrument 12 may then be oriented according to the medial-lateral and cranial-caudal angles previously determined (i.e. A1(*i*)=A1 and A2(*i*)=A2) and thereafter safely advanced through the pedicle. The depth of penetration of the surgical instrument 12 may be checked during advancement by rotating the C-arm back to a trajectory lateral view of FIG. 53. As pictured in FIG. 55, the surgical instrument 12 should appear parallel to the vertical reference line in the trajectory lateral view.

An alternate method for determining a preferred starting point for pedicle penetration utilizes the "owl's eye" view described below. Specifically, the C-arm is oriented to the "owls eye" view, or in other words both the medial-lateral and cranial-caudal angles of the C-arm 208 match the medial-lateral and cranial-caudal angles of the pedicle axis (A1(*c*) =A1 and A2(*c*)=A2). The tip of the pedicle access instrument 12 is placed on the skin so that the tip is located in the center of the pedicle of interest on the fluoroscope image; this marks the preferred incision site. The access instrument 12 is advanced to the pedicle and another fluoroscope image is taken to verify that the tip of the instrument is still aligned in the center of the pedicle.

To orient the C-arm 208 in the owl's eye position, the medial-lateral and cranial-caudal angles of the pedicle axis may each be determined as described with reference to FIGS. 21 and 51-53. Next, from the trajectory lateral position, the C-arm is rotated back to the A/P position while maintaining the cranial-caudal orientation achieved in the trajectory lateral position. Finally, while monitoring the feedback device 16, the C-arm 208 is orbitally rotated until the angle matches the medial-lateral angle derived from the preoperative planning (A2(*c*)=A2). At this point the fluoroscopic image, illustrated in FIG. 56, displays an "owl's eye" view of the pedicle, which appears generally as a circle.

Figure 55:
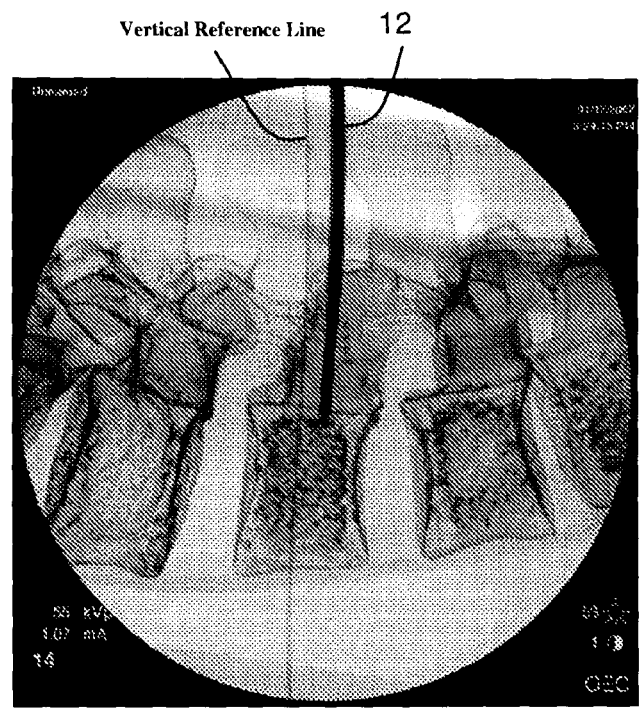
FIG. 55 is a trajectory lateral image for verifying the depth of penetration through a pedicle, according to one embodiment of the present invention.
Figure 56:
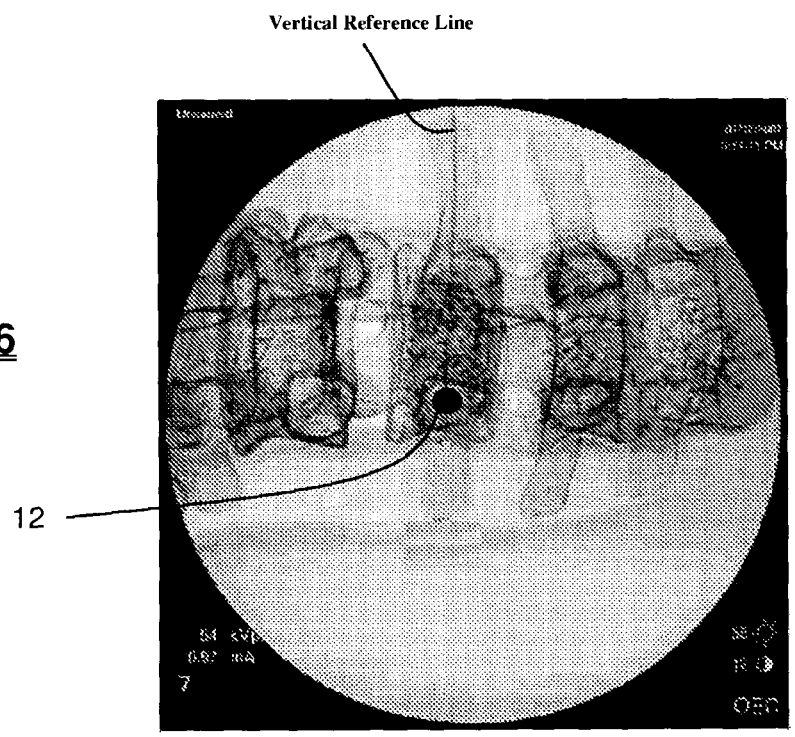
FIG. 56 is an "owls eye view" (i.e. looking straight along the pedicle axis) of the pedicle generated by orienting the C-arm with both the medial-lateral and cranial-caudal angles of the pedicle axis, according to one embodiment of the present invention.

The owl's eye view illustrated in FIG. 56 may be utilized for various reasons. By way of example, the owl's eye view may be used to determine the starting point for penetration of the pedicle as described. Also, in the owls eye image, a surgical instrument 12 properly aligned with the pedicle axis will appear as a black dot. Thus, once aligned, the surgical instrument may be advanced through the pedicle while ensuring that it continues to appear as only a dot on the fluoroscopy image. The depth of penetration may again be checked with a trajectory lateral image (FIG. 55). Additionally, if preoperative planning was not conducted to determine angle A1 of the pedicle axis, the C-arm can be manually (e.g. through trial and error) positioned in the owl's eye view. Once the C-arm is positioned in the owls eye position the tilt sensor 14 may be read to determine the angle A1.

Still another example of the gainful application of the surgical trajectory monitoring system 10 to enhance surgical safety and efficiency includes monitoring the orientation of surgical access instruments. Monitoring trajectory can aid in both the insertion and positioning of the access instruments themselves, as well as, aiding in the later insertion of instruments and/or implants through the surgical access instruments. One significant advantage is the ability to later visually align surgical instruments and/or implants along the same trajectory by visually comparing the alignment of the instrument to that of the access instrument Often times during a surgical procedure, the orientation of a surgical instrument or implant is of critical import to the success of the surgery. By way of example only, while placing bone screws through a pedicle (which is a small generally tubular structure connecting posterior elements of a vertebra to the vertebral body) it is critical to ensure the screw is contained within the pedicle and does not breach the outer pedicle wall. Since the pedicle is surrounded by delicate nervous tissue, a breach can have serious consequences for the patient, ranging from mild pain to paralysis. One way to mitigate the risk of a pedicle breach during screw placement (including preparation for screw placement, such as pilot hole formation and tapping) is to determine the angular orientation of the pedicle and thereafter advance the necessary instruments and screws along the determined trajectory. By orienting the surgical access components along the pedicle trajectory, the surgical instruments and pedicle screws may be simply and efficiently advanced along the same trajectory, and thus avoid a breach, by "eyeballing" alignment with the access components.

Figure 57:
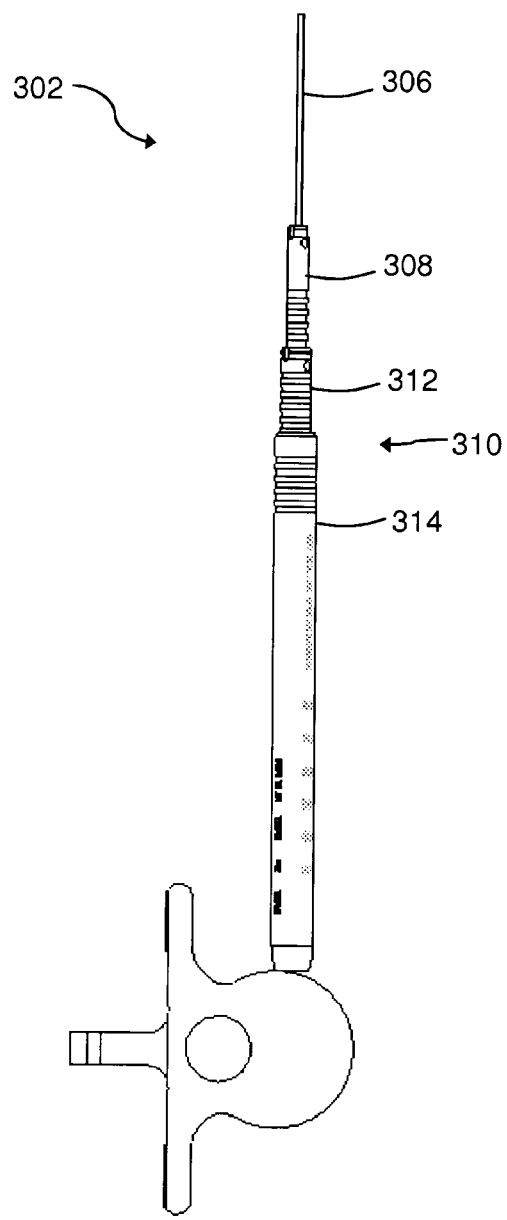
FIG. 57 is a side view illustrating the use of a tissue distraction assembly (comprising a plurality of dilating cannulae over a K-wire) to distract tissue between the skin of the patient and the surgical target site, according to one embodiment of the present invention.
Figure 58:
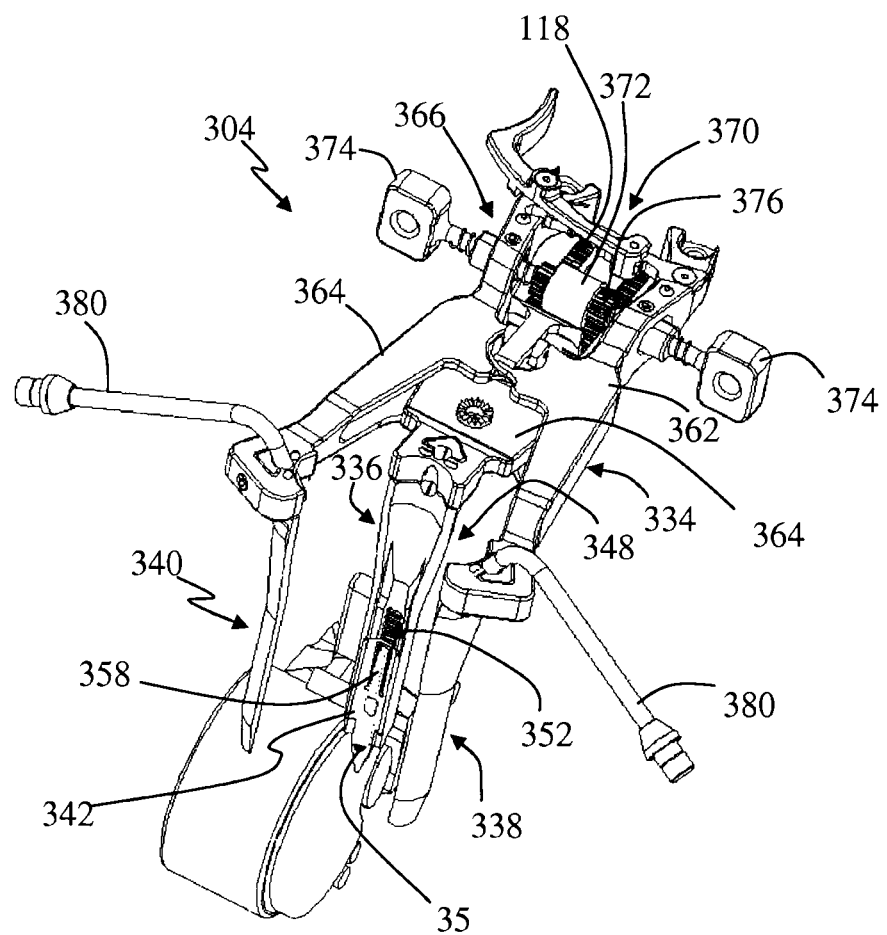
FIG. 58 is a perspective view of a tissue retraction assembly (in use) forming part of a surgical access system, according to one embodiment of the present invention.
Figure 59:
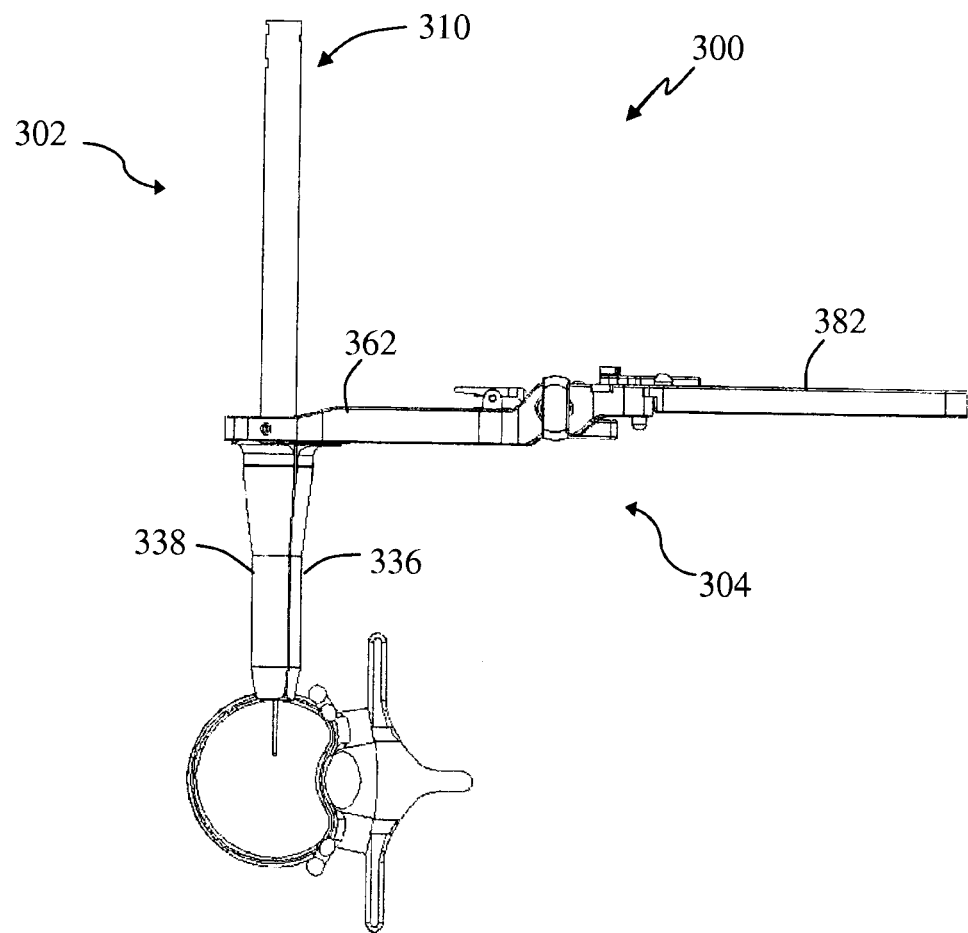
FIG. 59 is a side view of a retractor assembly according to the present invention, comprising a handle assembly having three (3) retractor blades extending therefrom disposed over a dilating assembly, according to one embodiment of the present invention.

An exemplary surgical access system 300 is described, by way of example only, with reference to FIGS. 57-59. Surgical access system 300 includes a tissue distraction assembly 302 (FIG. 57) and a tissue retraction assembly 304 (FIG. 58) generally of the type shown and described in commonly assigned U.S. Pat. No. 7,207,949, the entire contents of which is hereby incorporated in this disclosure as if set forth in its entirety herein.

As shown in FIG. 57, the tissue distraction assembly 302 includes a K-wire 306, an initial dilating cannula 308, and a sequential dilation system 310. In use, the K-wire 306 is disposed within the initial dilating cannula 308 and the assembly is advanced through the tissue towards the surgical target site (e.g. annulus). This is preferably accomplished while employing the nerve detection and/or direction features described below. As will be described in detail below, dilation may also be carried out along a desired angular trajectory path by using the surgical trajectory system 10 of the present invention. After the initial dilating assembly is advanced such that the distal end of the initial dilator 308 is positioned within the disc space, the sequential dilation system 310 consisting of one or more supplemental dilators 312, 314 may be employed for the purpose of further dilating the tissue down to the surgical target site. Each component of the sequential dilation system 310 (namely, the K-wire 306 and the supplemental dilators 312, 314) may, according to the present invention, be provided with one or more electrodes (preferably at their distal regions) equipped for use with a nerve surveillance system, such as, by way of example, the type associated with the neuromonitoring system 400 discussed below.

As shown in FIG. 58, the retraction assembly 304 includes a plurality of retractor blades extending from a handle assembly 334. By way of example only, the handle assembly 334 is provided with a first retractor blade 336, a second retractor blade 338, and a third retractor blade 340. Although shown and described below with regard to the three-bladed configuration, it is to be readily appreciated that the number of retractor blades may be increased or decreased without departing from the scope of the present invention. The retractor assembly 304 is shown in a fully retracted or "open" configuration, with the retractor blades 336, 338, 340 positioned a distance from one another so as to form an operative corridor 348 there between and extending to a surgical target site (e.g. an intervertebral disc). As will be described in detail below, the placement of the retraction assembly 304 may be carried out along a desired angular trajectory path by using the surgical trajectory system 10 of the present invention. Each component of the retraction system 304 (namely, the blades 336-340) may, according to the present invention, be provided with one or more electrodes (preferably at their distal regions) equipped for use with a nerve surveillance system, such as, by way of example, the type associated with the neuromonitoring system 400 discussed below.

To use the angle monitoring system 10 with the surgical access system 300, the desired trajectory of the surgical corridor may be determined. If for example, the surgeon intends to implant pedicle screws through the resulting operative corridor 348, it may be desirous to orient the surgical corridor 348 along the pedicle axis. Methods for determining the pedicle axis have been described previously and may be followed here again to obtain the desired angle values.

Once the pedicle trajectories have been determined the practitioner may begin advancing the surgical access system 300 according to the desired angular trajectory. The K-wire 306 is advanced into the pedicle. If a rigid K-wire is utilized the tilt sensor 14 may be attached to a proximal end of the K-wire 306 via universal clip 26, and the angle of insertion guided by the feedback device 16. After the K-wire 306 is docked in the vertebra, the clip 26 is removed (if it was used) and may be attached to the first dilator 308 for insertion, again following the desired trajectory via the feedback device 16. This is repeated until the last dilator 310 is in place over the surgical target site. Next, the tilt sensor 14 may be removed from the final dilator and attached to the retractor 304 and as previously described, the surgical retractor assembly 304 may be advanced to the target site over the outer dilator with the blades 336, 338, 340 in the "closed" position. The dilator is removed and the blades may be retracted to an "open" position providing a corridor 348 for the surgeon to work. If the angle of the retractor 304 was not determined during insertion it may be determined at this point by attaching the tilt sensor 14 in the manner described and then reading the measurements.

After the retractor assembly 304 is set in the proper angular alignment, a pilot hole may be formed in the pedicle. By way of example only a gear shift probe or awl may be advanced to the pedicle. Once the tip of the instrument rests on the pedicle the shaft of the instrument should be adjusted until it is aligned both medial-laterally and cranial-caudally with the axis of the first retractor blade 336. When aligned with the axis of the first blade, or in other words, with the longitudinal axis of the surgical corridor, the instrument tip may be driven into the pedicle along the pedicle axis, ensuring that the pedicle wall is not breached. This may be repeated for a tapping instrument and during screw insertion. After the first screw is inserted along the pedicle axis, the retractor system 304 may be adjusted until it is aligned with the axis of the next pedicle to receive a screw, and the steps are repeated again until the next screw is placed. Once every screw has been placed and connecting elements inserted and locked into the screws, the retractor system 304 may be removed. It will again be appreciated that although this method is described as orienting the retractor assembly along a pedicle axis and thereafter inserting instruments into the pedicle, there are any number of procedures which may be benefited by inserting an instrument along a specific trajectory and the method described applies equally thereto.

Figure 60:
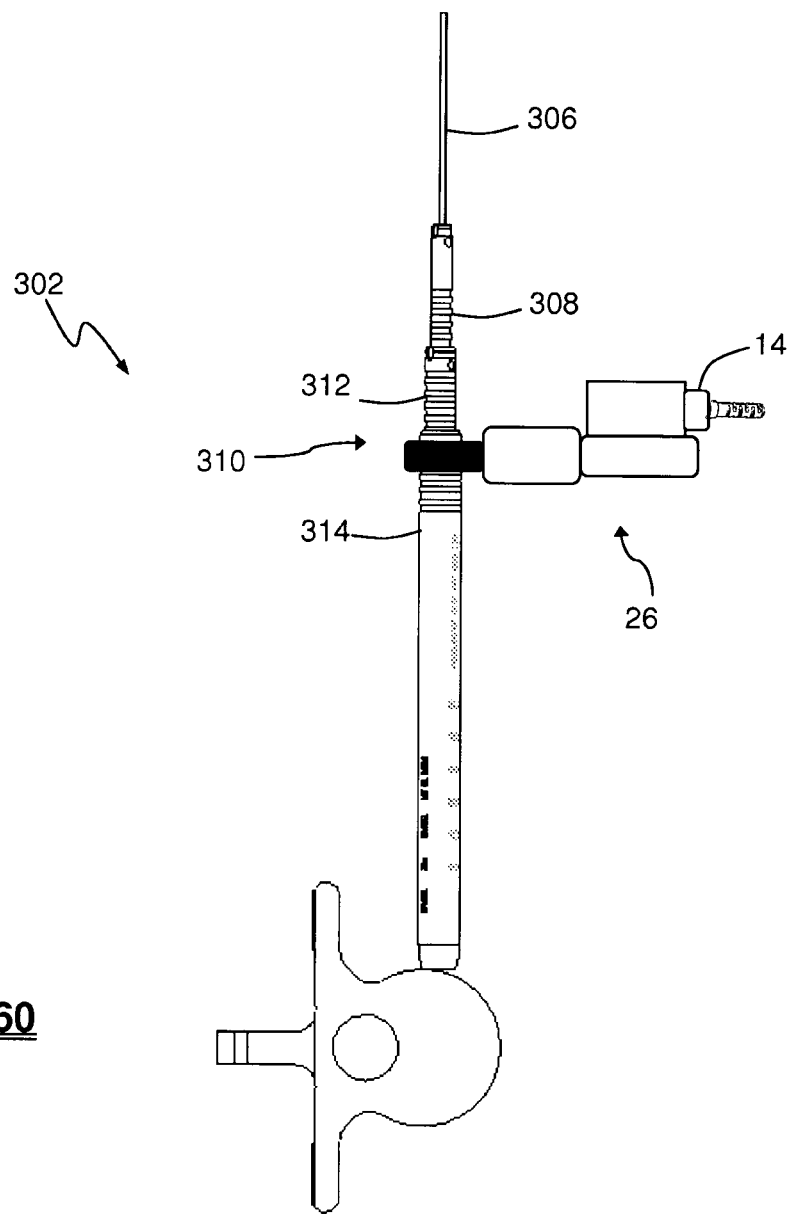
FIG. 60 is a side view illustrating the use of a tissue distraction assembly (comprising a plurality of dilating cannulae over a K-wire) to distract tissue between the skin of the patient and the surgical target site with a tilt sensor attached to the distraction assembly to monitor the angle of insertion, according to one embodiment of the present invention.

Coupling the tilt sensor 14 to the various components of the distraction assembly 302 and retraction assembly 304 may be accomplished in any of a variety of manners. With reference to FIG. 60, the universal clip 26 (and thus tilt sensor 14) may be attached to one of the sequential dilators 310. In the same fashion as described above in relation to the pedicle access probe, a portion of the surgical distraction component, preferably near the proximal end, is positioned within the hook of free end 54 of clip 26. Collar 34 may then be twisted to securely fasten the distraction component to the universal clip 26. When completely fastened, the tilt sensor 14 extends perpendicularly to the longitudinal axis of the distraction component. Since the component is angled in either of the sagittal or transverse planes, the user may be apprised of the angle relative to gravity via feedback device 16. It will be appreciated that while the tilt sensor 14 is shown in FIG. 60 attached only to the outer or largest dilator, the clip may be attached to the K-wire and then each dilator in turn if desired.

Figure 61:
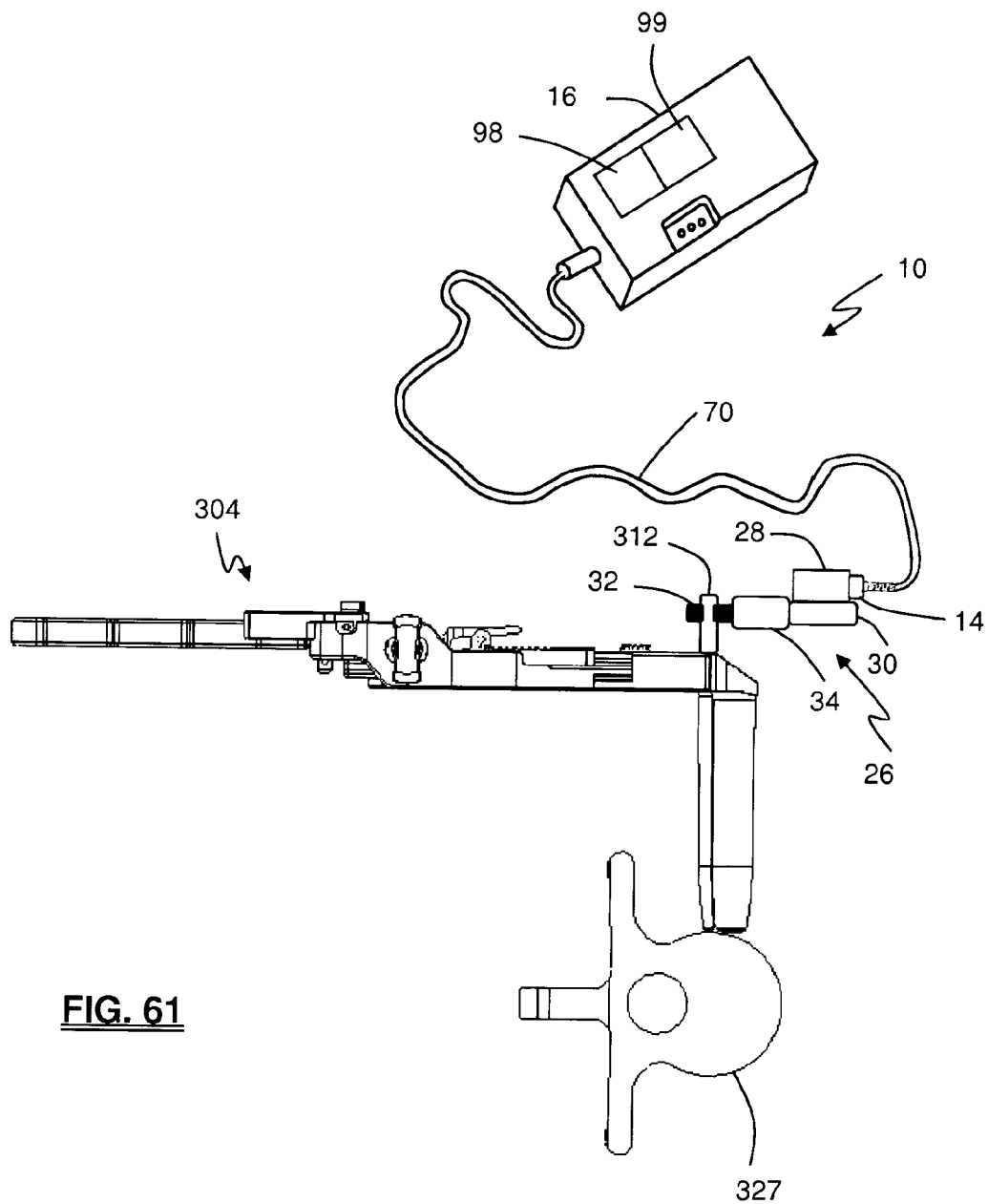
FIG. 61 is a side view of a surgical trajectory system, including a tilt sensor attached via a universal clip to a post connected to a first retractor blade, an LCD feedback device, and a tissue retractor, according to one embodiment of the present invention.
Figure 62:
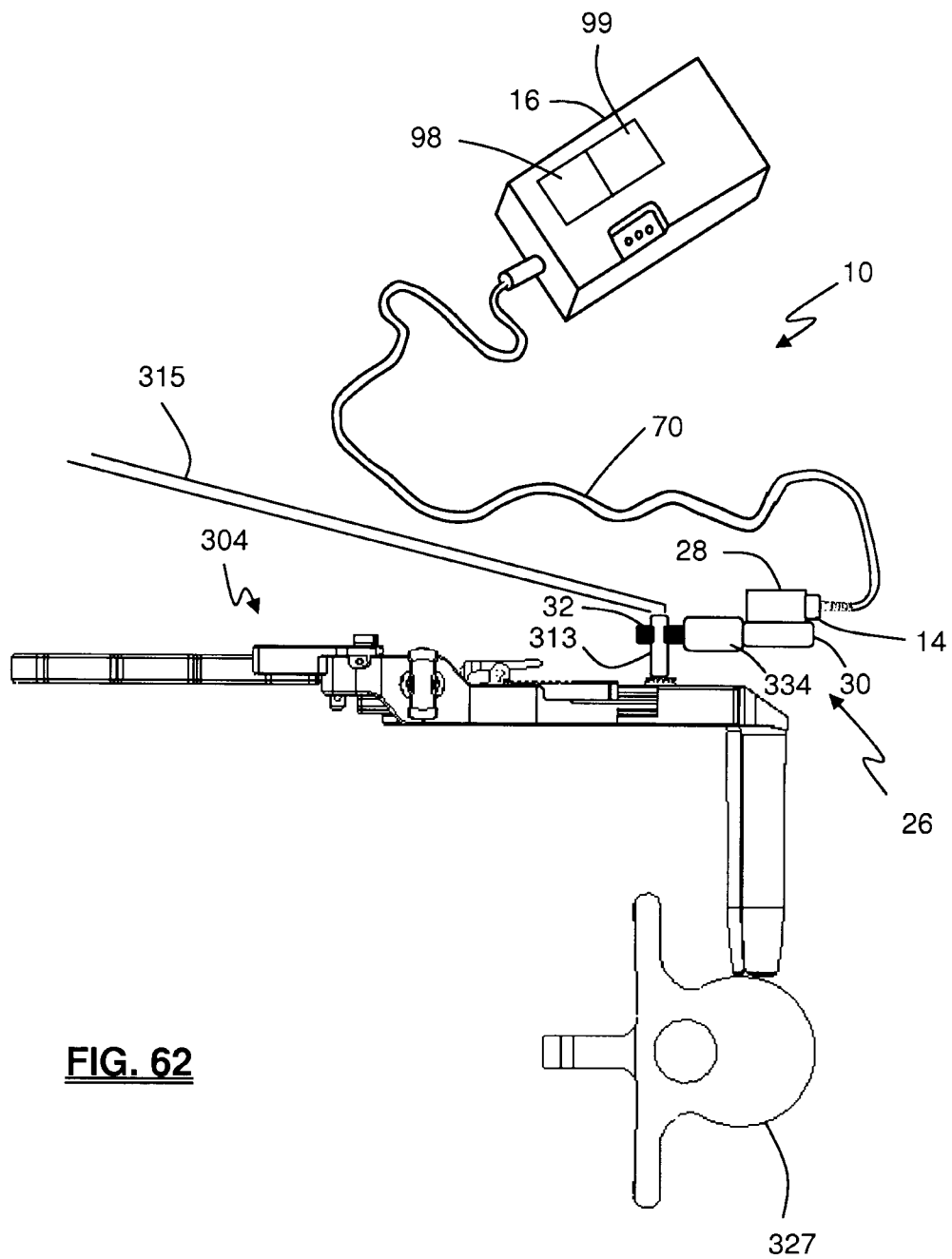
FIG. 62 is a side view of a surgical trajectory system, including a tilt sensor attached via a universal clip to a post comprising part of an articulating arm to which the retractor is attached, an LCD feedback device, and a tissue retractor, according to one embodiment of the present invention.
Figure 63:
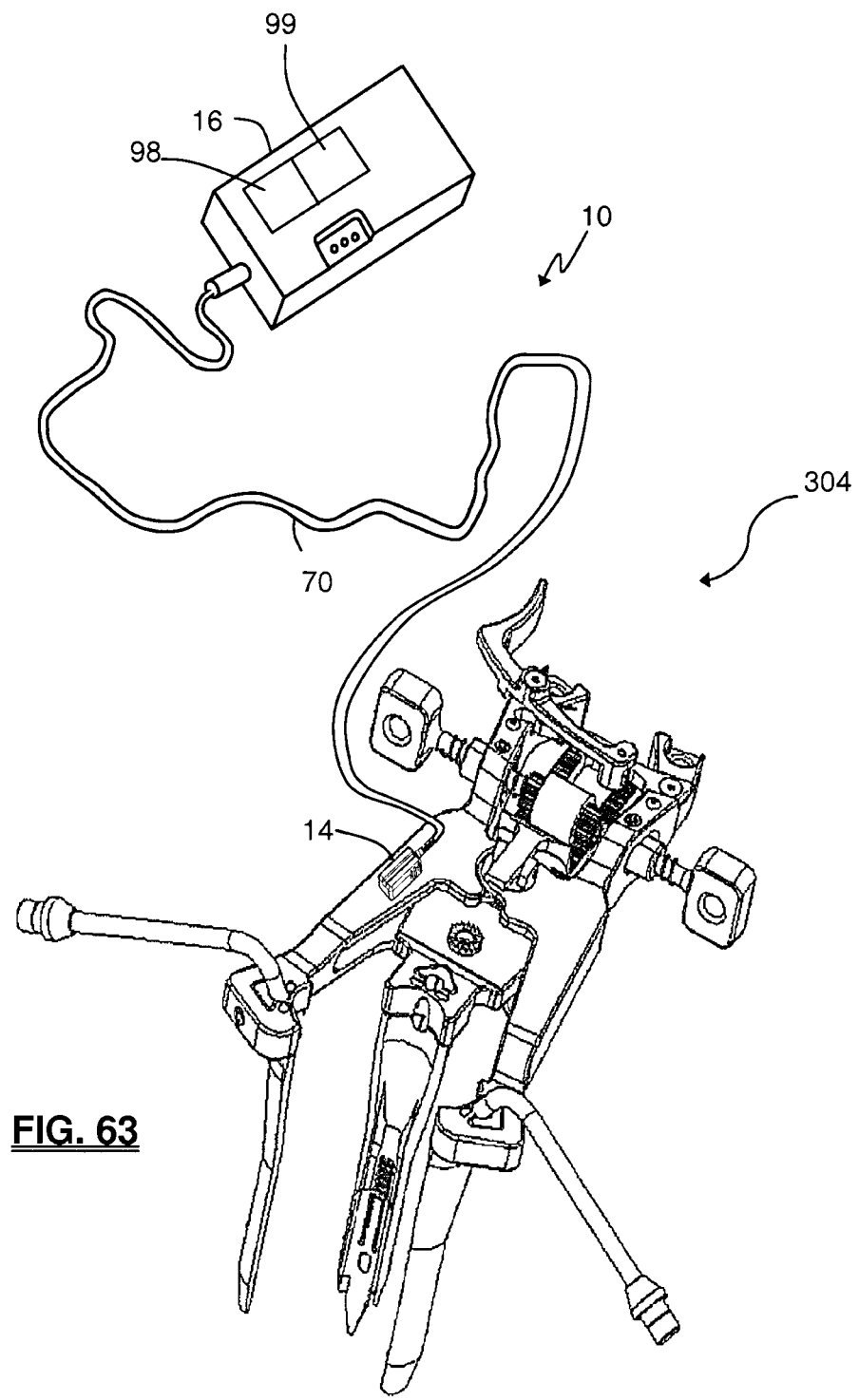
FIG. 63 is an exemplary view of a surgical trajectory system, including a tilt sensor attached positioned directly onto the surface of the tissue retraction of FIG. 60, according to one embodiment of the present invention.
Figure 65:
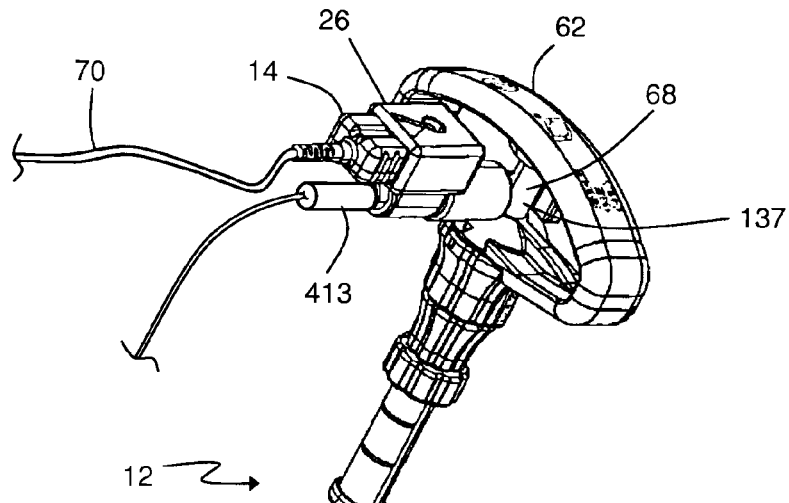
FIG. 65 is a perspective view showing the surgical instrument of FIG. 11 linked to both the surgical trajectory system of FIG. 1 and the neurophysiology monitoring system of FIG. 66, according to one embodiment of the present invention.

With reference to FIGS. 61-63, the universal clip 26 (and thus the tilt sensor 14) may be attached to the tissue retractor assembly 304. In FIG. 61, the universal clip 26 is attached to a post 312 extending vertically from the top of first retractor blade 336. This embodiment is advantageous in that the post 312 may be in electrical communication with an electrode 350 at or near the distal end of retractor blade 336. The universal clip 26 may be in electrical communication with a neuromonitoring system 400, described below, such that electrical stimulations from the neuromonitoring system 400 may thus be delivered through the universal clip 26, eliminating the need for connecting multiple devices to the retractor 304. In FIG. 65, the universal clip 26 is attached to a post 313 used to attach the surgical retractor assembly 304 to an articulating arm 315 which provides secure connection to the operating table and holds the retractor assembly in place.

Whether universal clip 26 is attached to post 312 (as in FIG. 61) or post 313 (as in FIG. 62) it will be appreciated that it extends perpendicular to the longitudinal axis of the surgical corridor 348 created between the retractor blades. It will be appreciated that, if and when the second and third retractor blades 338, 340 are rotated out during surgery, the longitudinal axis of the surgical corridor remains the same and follows the axis of the first blade 336 which does not rotate. It should also be appreciated that though the clip 26 is shown in FIGS. 61 and 62 extending over the retractor blades and the corridor 348 they create, this is done for the ease of viewing and preferably the surgical trajectory assembly 10 is oriented such that the clip 26 extends away from the surgical corridor when so as not to inhibit the surgeons ability to manipulate instruments and/or see the surgical wound.

FIG. 63 shows a tissue retractor connected directly to the handle assembly 334 of a tissue retractor 304 via any number of suitable manners, including but not limited to the use of a Velcro® patch, tape, strap, etc. . . . The tilt sensor 14 is preferably positioned on the handle assembly 334 such that it is perpendicular to the longitudinal axis of the spine, thus as it is shown in FIG. 63, the handle extensions would face out to the side of the patient, perpendicular to the longitudinal axis of the spine. If necessary, the tilt sensor may be detached and repositioned.

In addition to being physically coupled to the retractor 304, it will be appreciated that the tilt sensor 14 may be formed as an integral part of the retractor 304 and/or any individual component thereof without departing from the scope of the present invention. For example, the tilt sensor 14 may be formed as part of any of the retractor blades 336, 338, 340, any component of the handle assembly 334, and/or any component of the dilation assembly 302. In such an instance, the "tilt-sensor enabled component" may be have an electrical coupling and/or wireless communication technology to provide the tilt sensing functionality described herein and may be disposable or reusable as described herein.

The surgical trajectory system 10 described above may be used in combination with any number of neurophysiologic monitoring systems. These may include, but are not necessarily limited to, neurophysiologic monitoring system capable of conducting pedicle integrity assessments before, during, and after pilot hole formation, as well as to detect the proximity of nerves while advancing and withdrawing the surgical instrument (e.g probe 12, awl 80, dilation assembly 302, retraction assembly 304) from the pedicle target site. An exemplary neuromonitoring system 400 is shown by way of example in FIG. 64. Neuromonitoring system 400 has been described in detail elsewhere and will be described only briefly herein. By way of example only, the various functional modes of the neuromonitoring system 10 may include the Twitch Test, Free-run EMG, Basic Screw Test, Difference Screw Test, Dynamic Screw Test, MaXcess® Detection, and Nerve Retractor, all of which will be described briefly below. The Twitch Test mode is designed to assess the neuromuscular pathway via the so-called "train-of-four test" test to ensure the neuromuscular pathway is free from muscle relaxants prior to performing neurophysiology-based testing, such as bone integrity (e.g. pedicle) testing, nerve detection, and nerve retraction. This is described in greater detail within Int'l Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The Basic Screw Test, Difference Screw Test, and Dynamic Screw Test modes are designed to assess the integrity of bone (e.g. pedicle) during all aspects of pilot hole formation (e.g., via an awl), pilot hole preparation (e.g. via a tap), and screw introduction (during and after). These modes are described in greater detail in Int'l Patent App. No. PCT/US02/35047 entitled "System and Methods for Performing Percutaneous Pedicle Integrity Assessments," filed on Oct. 30, 2002, and PCT/US2004/025550, entitled "System and Methods for Performing Dynamic Pedicle Integrity Assessments," filed on Aug. 5, 2004 the entire contents of which are both hereby incorporated by reference as if set forth fully herein. The MaXcess® Detection mode is designed to detect the presence of nerves during the use of the various surgical access instruments of the neuromonitoring system 10, including the k-wire 62, dilator 64, cannula 66, retractor assembly 70. This mode is described in greater detail within Int'l Patent App. No PCT/US02/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within Int'l Patent App. No. PCT/US02/30617, entitled "System and Methods for Performing Surgical Procedures and Assessments," filed on Sep. 25, 2002, the entire contents of which are hereby incorporated by reference as if set forth fully herein. Although not described herein, various other functional modes may be performed by the system 10, such as for example only, MEP and SSEP functions which are described in detail within Int'l Patent App. No. PCT/US2006/003966, entitled "System and Methods for Performing Neurophysiologic Assessments During Spine Surgery," filed on Feb. 2, 2006, the entire contents of which are hereby incorporated by reference as if set forth fully herein.

Figure 64:
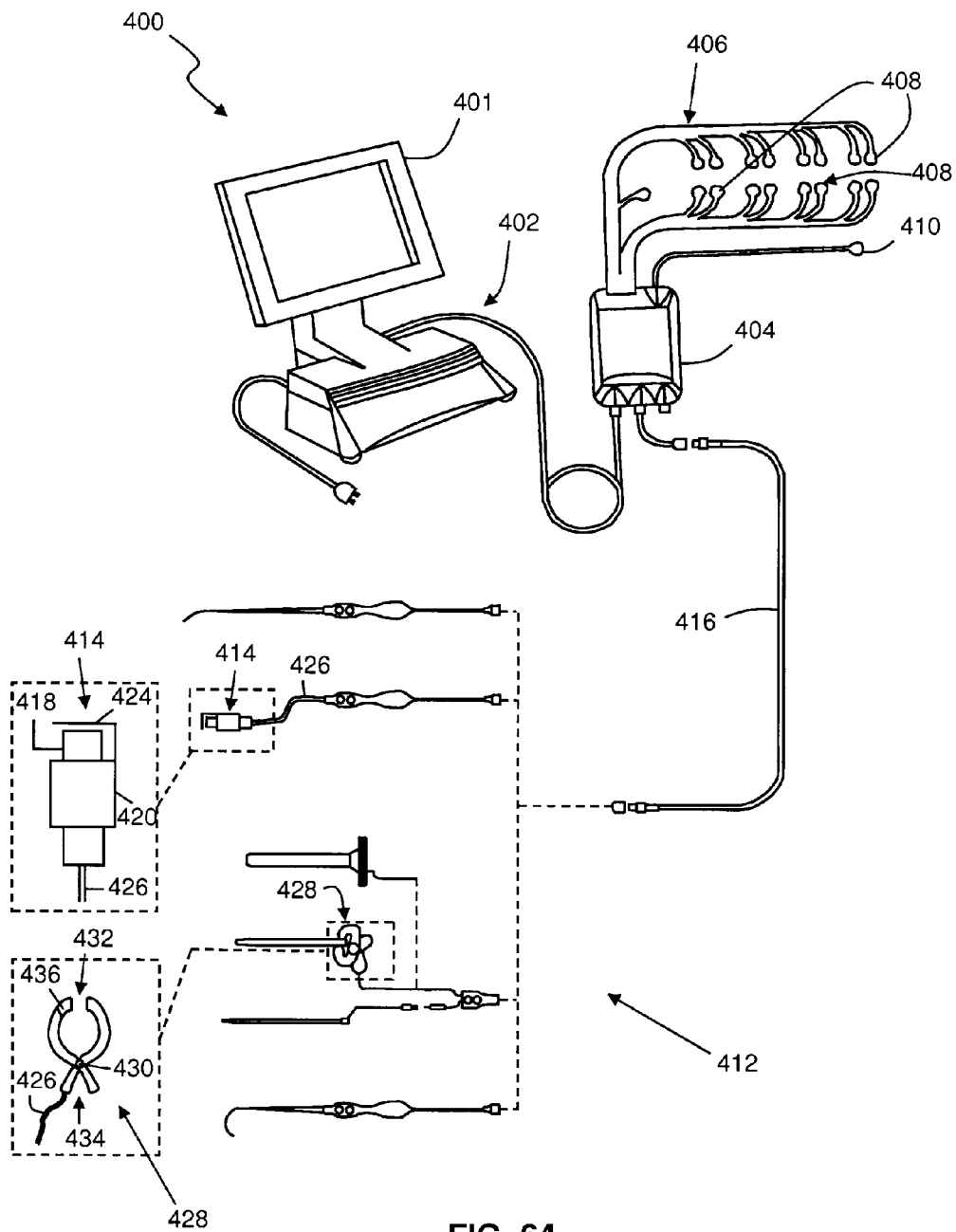
FIG. 64 is an exemplary view of a neurophysiology system capable connecting the pedicle access probe in order to conduct various nerve monitoring functions; according to one embodiment of the present invention.
Figure 66:
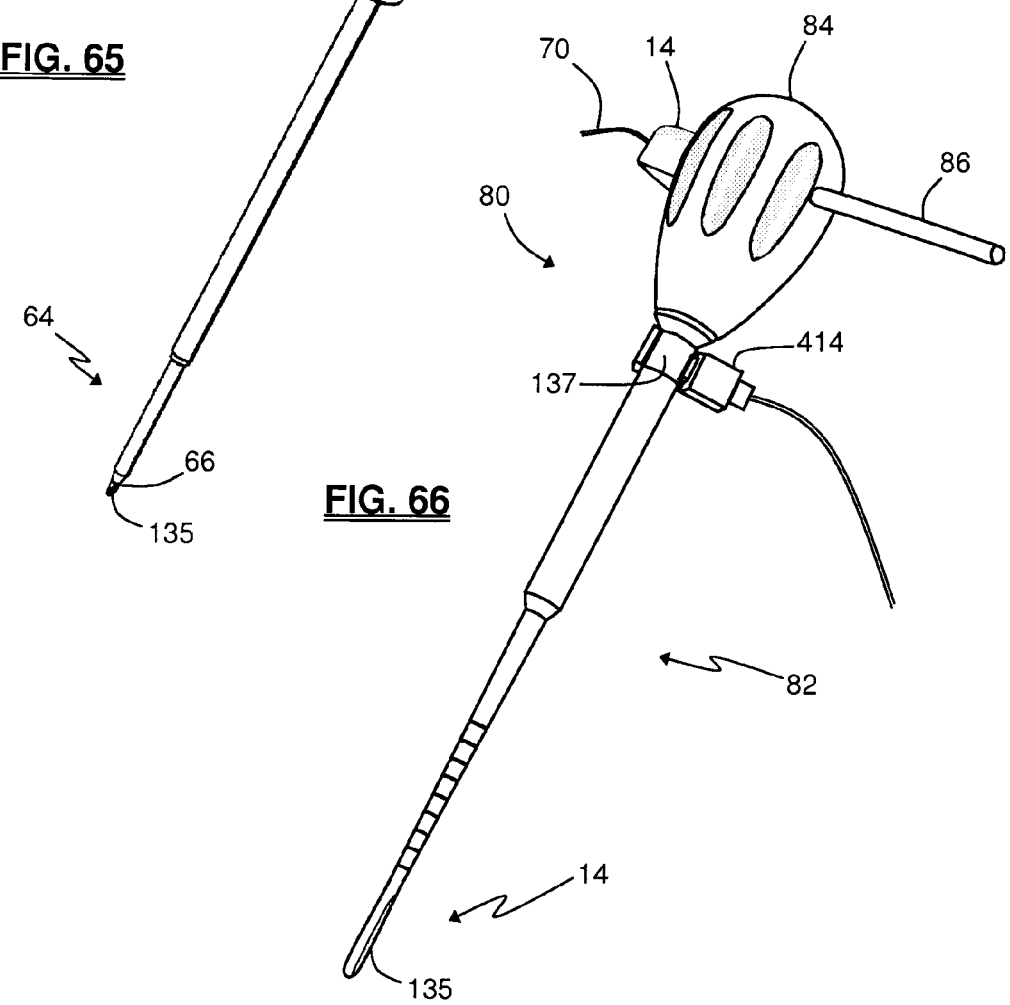
FIG. 66 is a perspective view showing the surgical instrument of FIG. 12 linked to both the surgical trajectory system of FIG. 1 and the neurophysiology monitoring system of FIG. 66, according to one embodiment of the present invention

With reference to FIG. 64, the neurophysiology system 400 includes a display 401, a control unit 402, a patient module 404, an EMG harness 406, including eight pairs of EMG electrodes 408 and a return electrode 410 coupled to the patient module 404, and a host of surgical accessories 412, including an electric coupling device 414 capable of being coupled to the patient module 404 via one or more accessory cables 416. As shown in FIGS. 65-66, to perform the neurophysiologic monitoring, the surgical instrument 12, 80 is configured to transmit a stimulation signal from the neurophysiology system 400 to the target body tissue (e.g. the pedicle). As previously mentioned, the probe members 60, 82 may be formed of material capable of conducting the electric signal. To prevent shunting of the stimulation signal, the probe members 60, 82 may be insulated. By way of example, a substantial portion of probe members 60, 82 may be provided with an insulative coating. Uninsulated portions near the distal end 90 form a stimulation region (or "electrode") 135. An additional uninsulated region is also provided near the proximal end of the probe member to serve as a coupling point 137 for linking the neurophysiology system to the instrument 80. In another embodiment, not shown, a retractable insulative sheath, as described in U.S. patent application Ser. No. 11/448,237, may be employed in place of, or in addition to the insulative coating. In still another alternative, probe members 60, 82 may be formed of a non-conductive material with one or more embedded conductive elements at or near the distal end capable of being communicatively linked with neurophysiology system 400.

The neurophysiology system 400 performs nerve monitoring during surgery by measuring the degree of communication between a stimulation signal and nerves or nerve roots situated near the stimulation site. To do this, the surgical instrument is connected to the neurophysiology monitoring system 400 and stimulation signals are activated and emitted from electrode 135. EMG electrodes 408 positioned over the appropriate muscles measure EMG responses corresponding to the stimulation signals. The relationship between the EMG responses and the stimulation signals are then analyzed by the system 400 and the results are conveyed to the practitioner on the display 401. More specifically, the system 400 determines a threshold current level at which an evoked muscle response is generated (i.e. the lowest stimulation current that elicits a predetermined muscle response). Generally the closer the electrode 135 is to a nerve the lower the stimulation threshold will be. Thus, as the probe member 60, 82, or surgical access members 302, 304 move closer to a nerve, the stimulation threshold will decrease, which may be communicated to the practitioner to alert him or her to the presence of a nerve. The pedicle integrity test, meanwhile, works on the underlying theory that given the insulating character of bone, a higher stimulation current is required to evoke an EMG response when the stimulation signal is applied to an intact pedicle, as opposed to a breached pedicle. Thus, if EMG responses are evoked by stimulation currents lower than a predetermined safe level, the surgeon may be alerted to a possible breach.

The surgical instrument 12, 80, 302, 304 may be connected to the neurophysiology system 400 by attaching a DIN cable 413 to the receptacle 50 of universal clip 26. When tilt sensor 14 is attached directly to the surgical instrument (rather than using universal clip 26), as with instrument 80 described above, an electric coupling device 414 may be provided with the neurophysiology system 400. The electric coupling device may be attached to the uninsulated coupling point 137 at the proximal end 64 of probe member 82. The electric coupling device 414 may comprise a number of possible embodiments which permit the system 400 to attach to the coupling point 137 and transmit a stimulation signal through the probe member 82.

One such embodiment of electric coupling device 414 utilizes a spring-loaded plunger to hold the coupling point 38 and transmit the stimulation signal. The plunger 418 is composed of a conductive material such as metal. A nonconductive housing 414 partially encases the plunger rod 418 about its center. Extending from the housing 420 is an end plate 424. An electrical cable 426 connects the electric coupling device 414 to neurophysiology system 400. A spring (not shown) is disposed within the housing 420 such that in a natural or "closed" state the plunger 418 is situated in close proximity to the endplate 424. Exerting a compressive force on the spring (such as by pulling the cable 426 while holding the housing 420) causes a gap between the end plate 424 and the plunger 418 to widen to an "open" position, thereby allowing insertion of the coupling point 137 between the end plate 424 and plunger 418. Releasing the cable 426 allows the spring to return to a "closed" position, causing the plunger 418 to move laterally back towards the endplate such that a force is exerted upon the coupling point 137 and thereby holds it in place between the endplate 424 and the plunger 418. Thereafter, the electrical stimulus may be passed from the neurophysiology system 400 through the cable 426 and plunger 418 to the probe member 82.

Alternatively, the electrical coupling device may be embodied in the form of a clip 428. The clip 428 is comprised of two prongs hingedly coupled at a coupling point 430 such that the clip 428 includes an attachment end 432 and a non-attachment end 434. A stimulation electrode 436 is disposed on the attachment end 432 and communicates with an electric cable 426 extending from the non-attachment end 434 to the neurophysiology system 400. In a "closed" position the prong ends at the attachment end 432 touch. Depressing the prongs at the non-attachment end 434 in a direction towards each other causes a gap to form between the prong ends at the attachment end 432. Positioning the "opened" attachment end 432 over the coupling point 137 and releasing the force on the non-attachment end 434 causes the attachment end 432 to pinch tight on the coupling point 137 and thereby allow the electrical stimulus to pass from neurophysiology system 400, through the stimulation electrode 236, to the probe member 82.

During pilot hole formation, while the trajectory of the surgical instrument is being monitored to prevent the instrument from breaching the pedicle walls, pedicle integrity assessments may be performed to alert the practitioner in the event a breach does occur. Stimulation signals are emitted from electrode 135, which should be at least partially positioned within the pedicle bone during hole formation. The stimulation threshold is determined and displayed to the surgeon via the neurophysiology monitoring system 400. Due to the insulating characteristics of bone, in the absence of a breach in the pedicle wall, the stimulation threshold current level should remain higher than a predetermined safe level. In the event the threshold level falls below the safe level, the surgeon is alerted to the potential breach. When the pilot hole is fully formed, a final integrity test should be completed.

In one embodiment, tilt sensor 14 is communicatively linked directly to control unit 402 of the neurophysiology monitoring system. The display 401 of neurophysiology system 400 replaces feedback device 16 of the trajectory monitoring system 10 and data from the tilt sensor 14 is shown jointly with the neurophysiologic data. As described above, audio indicia may also be communicated to the user regarding the trajectory angles.

The systems and methods described above may be utilized by personnel during surgical procedures to help maximize efficiency and increase safety. Each of the applications for, and methods of, using the surgical trajectory system 10 described above have advantages when used on their own and it is expressly noted that combining some or all of the different uses and methods of the trajectory system may be especially beneficial. By way of example only, a trajectory assisted method and procedure for pedicle fixation utilizing multiple aspects of the trajectory system 10 will now be described.

The trajectory assisted pedicle fixation procedure begins with the proper positioning of the patient 204. The patient is positioned on the surgical table 206 in the prone position and the affected spinal levels are adjusted until they are level with the floor. Once the patient is presumed to be properly positioned, one or more of a visual inspection, A/P fluorography, and a mechanical inspection with a level may be performed to verify the position.

After positioning of the patient 204 is complete the angles to be used for pilot hole formation may be determined. The first angles to be determined are the medial-lateral angles A1. As previously noted this step can be completed prior to the surgery and the medial-lateral angles for each pedicle to receive a screw are brought into the operating room for reference. To calculate the medial-lateral angle A1, the pedicle angle correction value should be determined (and loaded into CPU or the neuromonitoring system 400 if applicable), if necessary, by first determining the amount of rotation in the spine relative to the vertical reference in the MRI or CAT image. The angular difference between a line drawn connecting the posterior superior iliac spine (PSIS) and the line parallel to the bottom of MRI image box. Next, a line is drawn down the pedicle axis of each pedicle and a vertical reference line is drawn between them through the center of the vertebral body. A measuring device, such as a protractor may then be used to calculate the angular difference between the vertical reference line and the lines drawn through the axis of the pedicles. The values determined are the medial-lateral angles to use for pedicle cannulation during pilot hole formation. The step is repeated until the medial-lateral angle for each pedicle of interest is determined. Again if necessary, correct the angle values determined based on the pedicle angle correction value.

After determining the medial-lateral angles for each pedicle, the next step is to obtain the cranial-caudal angles A2 for each pedicle as well. The superior endplate is positioned parallel to the reticle plumb line 274. The angle of the pedicle axis is (or vertebral endplate) is measured relative to the C-arm gravity line. This is accomplished by first placing the C-arm 208 into the lateral orientation. The reticle line represents the gravity line and all cranial-caudal angles are measured relative to this reference line. The head or foot of the surgical table 206 may be raised or lowered to attain parallel alignment between the superior endplate of applicable vertebral body and this reference line, if desired.

The cranial and caudal angles of applicable pedicle axes or superior endplates are measured via one of two methods. First, a protractor 120 outfitted with a tilt sensor 14 may be lined up with the vertical reference line formed by the plumb line 274 and zeroed. Subsequently, the protractor 120 is rotated into alignment with the pedicle axis or desired trajectory. Subsequent angles are measured per vertebral level using the same method.

In the second method, the plumb/reticle line 274 and the associated tilt sensor 14 is utilized to measure the angles. The C-arm 208 is rotated in radial rotation until the plumb line 274 parallel to the pedicle axis or superior endplate of interest and the angle is noted. Then the plumb line 274 is rotated parallel to the superior endplate of the upper level vertebra and the angle is noted. The resulting cranial caudal angles are recorded and are used to facilitate later positioning of the C-arm into the A/P plane of the vertebra of interest.

The next main step of the trajectory assisted pedicle fixation procedure of the preset invention is to properly position the C-arm 208. Initially all the C-arm articulations are set to zero and the horizontal arm is set at midline. Next the C-arm radial rotation is set to the predetermined cranial-caudal angle A2 for the level of interest. The C-arm base is then translated cranially or caudally to align the plumb/reticle reference line 274 parallel to the superior endplate of the vertebral body of interest. Then the orbital rotation of the C-arm is altered slowly until the C-arm angle A1(c) matches the predetermined medial-lateral angle A1. Finally, the C-arm is translated using horizontal arm translation to center beam 218 over the right lower level pedicle.

Next the starting point for pedicle cannulation is determined. A tilt sensor 14 is attached to the pedicle access instrument 12. The tip of the instrument 12 is placed on the skin so that the tip is located in the center of the pedicle and the location is marked with a pen. Using a scalpel a longitudinal 1.5 cm incision centered over the pen mark is made.

The instrument 12 is advanced oriented in the same owl's eye trajectory, through the incision all the way to the bone. A C-arm 208 image is used to see if the tip of the needle is near the axis of the pedicle. If not the tip is adjusted until it is directly in the center of the lower level pedicle.

The surgical instrument 12 is attached to the neuromonitoring system 400 and via the one of a coupling device 414 and DIN cable 413. Once neuromonitoring capability is established the instrument is advanced to a depth of 1 cm and medial wall integrity is confirmed with a C-arm 208 shot at the 1 cm point. The instrument may be advanced while making any adjustments necessary to keep the trajectory in line with the pedicle axis. A final C-arm 208 shot may be taken at the final position for confirmation. After pedicle cannulation is performed on the right side of the lower level, the steps may be repeated again on the left side.

To move on to adjacent levels, owl's eye views may be obtained from previous levels by C-arm articulations and x-ray image sequences according to the following: first orient the C-arm by radial rotation to the upper level specific cranial-caudal angle; align the target level superior endplate with the reticle/plumb line 274 by C-arm base translation; next orient the C-arm by orbital rotation to specific medial-lateral angle; then translate the C-arm horizontal arm translation to center the pedicle of interest in the image; and finally, cannulate the pedicle. These steps are repeated until all pedicles have been cannulated. Implantation of the pedicle screws and supporting rods may now be implanted, preferably using a lateral fluoroscopy view.

While the invention is susceptible to various modifications and alternative forms, (such as the drill bit, needle points, and T-handle mentioned above) specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the scope and spirit of the invention as defined herein. By way of example, the method for determining the cranial-caudal A2 has been described herein as taking place intraoperatively using lateral fluoroscopy imaging. However, the cranial-caudal angle may also be determined preoperatively employing various imaging and/or computer processing applications. For example, a 3-D model of a patient's vertebra (or other applicable body part) may be obtained using a combination of medical imaging and computer processing. From the 3-D model the angle A2 may be calculated after which the determined value may be utilized by the surgical trajectory system and methods described above. It is further contemplated that computer processing of medical images may be used to extrapolate the pedicle axis angles A1 and A2 without the need for human intervention. Finally, it will be appreciated that the intraoperative monitoring discussed herein has generally focused on the use of a C-arm fluoroscopic imager, however, orienting the C-arm with a tilt sensor and providing a trajectory oriented reticle/plumb line using the methods and systems described herein may apply to any form of intraoperative monitoring.

What is claimed is:

1. A system for controlling the trajectory of a surgical instrument, comprising:
  a surgical instrument having a proximal portion, a distal portion, and a longitudinal axis extending between said proximal portion and said distal portion, said distal portion configured for advancement through body tissue to a target surgical site and said proximal portion configured to remain outside said body tissue when said distal portion is advanced to said target surgical site and to accommodate an orientation sensor removably coupled thereto such that said surgical instrument is orientable along a desired trajectory, said surgical instrument operable to at least one of create an access corridor, maintain said access corridor, and form a hole in bone;
  said orientation sensor operable to determine a first angular relationship in a first plane between said sensor and a reference direction and operable to determine a second angular relationship in a second plane between said orientation sensor and said reference direction, wherein said second plane is orthogonal to said first plane and said orientation sensor is removably coupled to said surgical instrument in a known orientation, wherein said orientation sensor is operable while said distal portion of said surgical instrument is positioned within said body tissue; and a feedback device communicatively coupled to said sensor and configured to communicate information to a user regarding at least one of said determined first and second angular relationships between said orientation sensor and said reference direction;

wherein said surgical instrument is further configured to angulate about said distal portion until said feedback device indicates that the angular orientation of said surgical instrument longitudinal axis in said first plane matches the desired instrument trajectory in said first plane and the angular orientation of said surgical instrument longitudinal axis in said second plane matches the desired instrument trajectory in said second plane.

2. The system of claim 1, wherein said orientation sensor comprises at least one accelerometer and said reference direction is gravity.

3. The system of claim 1, wherein said surgical instrument includes at least one of a pedicle hole formation instrument, a tissue dilation instrument, and a tissue retraction instrument.

4. The system of claim 3, wherein said pedicle hole formation instrument includes at least one of a pedicle access needle assembly, a pedicle access probe, a drill, and a tap, wherein said tissue dilation instrument includes at least one of a K-wire and a dilation cannula, and wherein said tissue retraction instrument includes a retractor.

5. The system of claim 1, wherein said sensor is temporarily coupled to said instrument by a connector having a first end for releasably engaging said instrument.

6. The system of claim 1, wherein said feedback device includes at least one of a liquid crystal display (LCD) screen, a light emitting diode (LED) light, an audio output device, and a computer and wherein said information includes at least one of alpha-numeric indicia, graphic indicia, color indicia, and audio signals regarding at least one of said first and second determined angular relationships between said sensor and said reference direction.

7. The system of claim 6, wherein said computer also comprises a neurophysiologic monitoring system and said sensor is communicatively coupled to said neurophysiologic system.

8. The system of claim 7, wherein said computer is configured to receive values for at least one of the first and second determined angular relationships between said sensor and said reference direction, wherein at least one of said first and second determined angular relationships between said sensor and said reference direction is determined at least one of pre-operatively and intra-operatively.

9. The system of claim 6, wherein at least one of the LCD screen and LED light is configured to display a color indicative of the trajectory of the instrument relative to at least one of the first and second determined angular relationships between said sensor and said reference direction.

10. The system of claim 9, wherein said color includes at least one of a green color indicative of an optimal variance between said trajectory of said instrument an at least one of the first and second determined angular relationships.

11. The system of claim 6, wherein said audio output device generates an audible signal indicative of the trajectory of the instrument relative to at least one of the first and second determined angular relationships between said sensor and said reference direction.

12. The system of claim 11, wherein said audible signal includes at least one of a first audible signal indicative of an optimal variance between said trajectory of said instrument and at least one of the first and second determined angular relationships between said sensor and said reference direction, a second audible signal indicative of an unacceptable variance between said trajectory of said instrument and at least one of the first and second determined angular relationships between said sensor and said reference direction, and a third audible single indicative of an acceptable yet not optimal variance between said trajectory of said instrument and at least one of the first and second determined angular relationships between said sensor and said reference direction.

13. The system of claim 1, wherein said feedback device is located within the surgical field.

14. The system of claim 13, wherein said feedback device is attached to at least one of said sensor, said instrument, and a user.

15. The system of claim 1, further comprising a second orientation sensor configured to determine an angular relationship within said first plane between said sensor and a reference direction and configured to determine an angular relationship within said second plane between said sensor and said reference direction, wherein said second sensor is mountable to a second surgical instrument.

16. The system of claim 15, wherein said second instrument is used to determine a desired trajectory to perform a surgical procedure and wherein said second instrument is one of an imaging system and a measuring device.

17. The system of claim 16, wherein said imaging system includes at least one of computer tomography imaging system magnetic resonance imaging system, an X-ray imaging system, and a fluoroscopic imaging system.

18. The system of claim 17, wherein a beam of said imaging system is positioned along the desired trajectory for the surgical procedure.

19. The system of claim 1, wherein said first plane is a sagittal plane.

20. The system of claim 1, wherein said second plane is a transverse plane.

21. A method for safely implanting a screw within the vertebral pedicle of a patient, comprising the steps of:
determining the angular orientation of said pedicle in each of a sagittal plane and a transverse plane;
advancing at least a portion of a surgical instrument through said patient to said pedicle, wherein said surgical instrument includes a distal end configured for advancement into said pedicle to form a pilot hole therein and a proximal end removeably equipped with an orientation sensor operable to determine the angular orientation of said instrument in each of said sagittal plane and said transverse plane;
angulating said surgical instrument about said distal end until a feedback device communicatively linked to said orientation sensor indicates that the angular orientation of said surgical instrument in said sagittal plane matches the angular orientation of said pedicle in said sagittal plane and the angular orientation of said surgical instrument in said transverse plane matches the angular orientation of said pedicle in said transverse plane;
advancing said distal end into said pedicle to form a pilot hole; and
implanting a screw in said pilot hole.

22. The method of claim 21, wherein said surgical instrument comprises at least one of a pedicle access probe, a drill, and a tap.

23. The method of claim 21, comprising the additional step of equipping said surgical instrument with said orientation sensor by attaching a connector housing said sensor to said proximal end.

24. The method of claim 23, wherein said feedback device comprises at least one LED on said connector and indicating that the angular orientation of said surgical instrument in said sagittal plane matches the angular orientation of said pedicle in said sagittal plane and the angular orientation of said surgical instrument in said transverse plane matches the angular orientation of said pedicle in said transverse plane comprises lighting said at least one LED in a first color.

25. The method of claim 24, comprising the additional step of lighting said at least one LED in a second color when at least one of said angular orientation of said surgical instrument in said sagittal plane does not match the angular orientation of said pedicle in said sagittal plane and the angular orientation of said surgical instrument in said transverse plane does not match the angular orientation of said pedicle in said transverse plane.

26. The method of claim 21, wherein said feedback device comprises a computer display and indicating that the angular orientation of said surgical instrument in said sagittal plane matches the angular orientation of said pedicle in said sagittal plane and the angular orientation of said surgical instrument in said transverse plane matches the angular orientation of said pedicle in said transverse plane comprises displaying at least one of alpha-numeric and graphic indicia related to said angular orientation of said surgical instrument.

27. The method of claim 21, comprising the additional step of equipping an imaging system with a second orientation sensor operable to determine the angular orientation of an imaging beam in each of said sagittal plane and said transverse plane and wherein said second orientation sensor is associated with at least one radiodense marker positioned in the path of said imaging beam.

28. The method of claim 21, wherein determining said angular orientation of said pedicle in said sagittal plane comprises the additional steps of:

adjusting the angular orientation of said imaging system such that said imaging beam is perpendicular to the direction of gravity and said radiodense marker is parallel to said direction of gravity;
capturing an image of said vertebral pedicle; and
measuring the angle of said pedicle with respect to a reference line created by said radiodense marker.

29. A method for controlling the angular orientation of a radiological imaging system, comprising the steps of:
removeably equipping said radiological imaging system with an accelerometer;
communicating at least one of a first angular relationship in a first plane with respect to the acting direction of gravity and a second angular relationship in a second plane with respect to the acting direction of gravity on a feedback device communicatively linked to said accelerometer; and
angulating said imaging system until said feedback device indicates that the angular orientation of said imaging system in said first plane matches the angular orientation of a pedicle in said first plane and the angular orientation of said imaging system in said second plane matches the angular orientation of said pedicle in said second plane.

30. The method of claim 29, wherein said imaging system comprises an x-ray fluoroscopic system.

31. The method of claim 29, wherein said first plane is a sagittal plane.

32. The method of claim 29, wherein said second plane is a transverse plane.

* * * * *